United States Patent
Buturovic et al.

(10) Patent No.: US 10,295,540 B1
(45) Date of Patent: May 21, 2019

(54) SYSTEMS AND METHODS FOR PHENOTYPIC CLASSIFICATION USING BIOLOGICAL SAMPLES OF DIFFERENT SAMPLE TYPES

(75) Inventors: Ljubomir J. Buturovic, East Palo Alto, CA (US); Rajeswari Pillai Tadakamalla, Sunnyvale, CA (US)

(73) Assignee: Cancer Genetics, Inc., Rutherford, NJ (US)

( * ) Notice: Subject to any disclaimer, the term of this patent is extended or adjusted under 35 U.S.C. 154(b) by 709 days.

(21) Appl. No.: 12/705,443

(22) Filed: Feb. 12, 2010

Related U.S. Application Data

(60) Provisional application No. 61/152,603, filed on Feb. 13, 2009.

(51) Int. Cl.
*G01N 33/48* (2006.01)
*G01N 33/574* (2006.01)
*G01N 33/84* (2006.01)
*G01N 33/483* (2006.01)
*G01N 33/50* (2006.01)
*A61N 5/10* (2006.01)

(52) U.S. Cl.
CPC ....... *G01N 33/574* (2013.01); *G01N 33/4833* (2013.01); *G01N 33/5035* (2013.01); *G01N 33/84* (2013.01); *A61N 5/1039* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,970,718 B2 * | 6/2011 | Guyon et al. | 706/20 |
| 2005/0209785 A1 * | 9/2005 | Wells et al. | 702/19 |
| 2006/0154267 A1 * | 7/2006 | Ma et al. | 435/6 |
| 2011/0312530 A1 * | 12/2011 | Aharonov | C12Q 1/6886 506/9 |

FOREIGN PATENT DOCUMENTS

WO    WO 2006/110212    10/2006

OTHER PUBLICATIONS

Brown et al. (Proceedings of the National Academy of Science, 2000, 97(1): 262-267) (Year: 2000).*
U.S. Appl. No. 12/378,187, Buturovic et al.
Chung et al., "Factors in tissue handling and processing that impact RNA obtained from formalin-fixed, paraffin-embedded tissue", J. Histochem. Cytochem. 56:1033-1042 (2008).
Dunn et al., "Genome-wide expression analysis of recently processed formalin-fixed paraffin embedded human prostate tissues", Prostate 69:214-218 (2009).
Erlander et al., "Molecular classification of carcinoma of unknown primary by gene expression profiling from formalin-fixed paraffin-embedded tissues", J. Clin. Oncol. 22(14S): Abstr. 9545 (2004).
Farragher et al., "RNA expression analysis from formalin fixed paraffin embedded tissues", Histochem. Cell Biol. 130:435-445 (2008).
Fedorowicz et al., "Microarray analysis of RNA extracted from formalin-fixed, paraffin-embedded and matched fresh-frozen ovarian adenocarcinomas", BMC Med. Genomics 2:23 (2009).
Frank et al., "Global gene expression profiling of formalin-fixed paraffin-embedded tumor samples: a comparison to snap-frozen material using oligonucleotide microarrays", Virchows Arch. 450:699-711 (2007).
Furey et al., "Support vector machine classification and validation of cancer tissue samples using microarray expression data" Bioinformatics 16:906-914 (2000).
Giordano et al., "Organ-specific molecular classification of primary lung, colon, and ovarian adenocarcinomas using gene expression profiles", Am. J. Pathol. 159:1231-1238 (2001).
Hewitt et al., "Tissue handling and specimen preparation in surgical pathology: issues concerning the recovery of nucleic acids from formalin-fixed, paraffin-embedded tissue", Arch. Pathol. Lab. Med. 132:1929-1935 (2008).
Horlings et al., "Gene expression profiling to identify the histogenic origin of metastatic adenocarcinomas of unknown primary", J. Clin. Oncol. 26:4435-4441 (2008).
Hui et al., "Robust global micro-RNA profiling with formalin-fixed paraffin-embedded breast cancer tissues", Lab. Invest. 89:597-606 (2009).
Ismael et al.. "Molecular profiling of a tumor of unknown origin", N. Eng. J. Med. 355:1071-1072 (2006).
Lassmann et al., "A novel approach for reliable microarray analysis of microdissected tumor cells from formalin-fixed and paraffin-embedded colorectal cancer resection specimens", J. Mol. Med. 87:211-224 (2009) e-pub Dec. 6, 2008.

(Continued)

*Primary Examiner* — Pablo S Whaley
(74) *Attorney, Agent, or Firm* — Morgan, Lewis & Bockius LLP

(57) ABSTRACT

Systems and methods are provided for identifying a set of highly-correlated genes for use in classifying both a first type of biological sample and a second type of biological sample as to a phenotypic characterization, where the first type of biological sample and the second type of biological sample are a sample type selected from the group consisting of a fresh biological sample, a frozen biological sample, a biological sample that has been preserved with a non-crosslinking preservative, and a fixed biological sample that has been fixed with a crosslinking agent, and where the first type of biological sample and the second type of biological sample are sample types that are not the same sample type. The invention also relates to computer systems and methods for use in training a classifier using the highly-correlated genes, and using the trained classifier to classify biological samples that are of the same sample type as the first type of biological sample or the second type of biological sample.

11 Claims, 12 Drawing Sheets

(56) References Cited

OTHER PUBLICATIONS

Ma et al., "Molecular classification of human cancers using a 92-gene real-time quantitative polymerase chain reaction assay", Arch. Pathol. Lab. Med. 130:465-473 (2006).

Medeiros et al., "Tissue handling for genome-wide expression analysis: a review of the issues, evidence, and opportunities", Arch. Pathol. Lab. Med. 131:1805-1816 (2007).

Penland et al., "RNA expression analysis of formalin-fixed paraffin-embedded tumors", Lab. Invest. 87:383-391 (2007).

Ravo et al., "Quantitative expression profiling of highly degraded RNA from formalin-fixed, paraffin-embedded breast tumor biopsies by oligonucleotide microarrays", Lab. Invest. 88:430-440 (2008).

Rimsza et al., "Major histocompatibility class II (MHC II) and germinal center associated gene expression correlate with overall survival in Ritiximab and CHOP-like treated diffuse large B cell lymphoma (DLBCL) patients using formalin fixed paraffin embedded (FFPE) tissues", Am. Soc. Hematol. 110(11):23a-24a, abstr. 50 (2007).

Rosenfeld et al., "MicroRNAs accurately identify cancer tissue origin", Nature Biotechnol. 26:462-469 (2008) e-pub Mar. 23, 2008.

Su et al., "Molecular classification of human carcinomas by use of gene expression signatures", Cancer Res. 61:7388-7393 (2001).

Szafranska et al., "Accurate molecular characterization of formalin-fixed, paraffin-embedded tissues by microRNA expression profiling", J. Mol. Diag. 10:415-423 (2008).

Tothill et al., "An expression-based site of origin diagnostic method designed for clinical application to cancer of unknown origin", Cancer Res. 65:4031-4040 (2005).

Van Laar et al., "Implementation of a novel microarray-based diagnostic test for cancer of unknown primary", Int. J. Cancer 125:1390-1397 (2009).

Xi et al., "Systematic analysis of microRNA expression of RNA extracted from fresh frozen and formalin-fixed paraffin-embedded samples", RNA 13:1668-1674 (2007) e-pub Aug. 13, 2007.

* cited by examiner

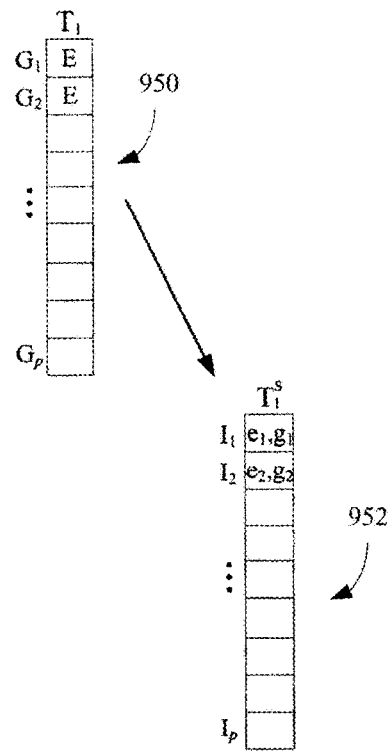
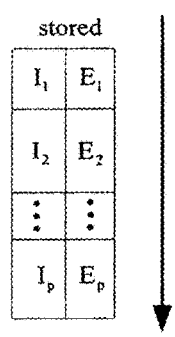
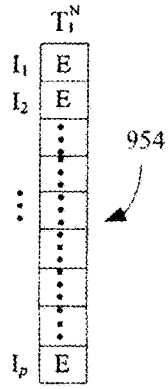
Fig. 9C
Fig. 9D

SYSTEMS AND METHODS FOR PHENOTYPIC CLASSIFICATION USING BIOLOGICAL SAMPLES OF DIFFERENT SAMPLE TYPES

This application claims benefit of U.S. Provisional Application No. 61/152,603 filed Feb. 13, 2009, which is incorporated by reference herein in its entirety.

1. FIELD OF THE INVENTION

The field of this invention relates to computer systems and methods for identifying a set of highly-correlated genes for use in classifying both a first type of biological sample and a second type of biological sample, where the first type of biological sample and the second type of biological sample are a sample type selected from the group consisting of a fresh biological sample, a frozen biological sample, a biological sample that has been preserved with a non-crosslinking preservative, and a fixed biological sample that has been fixed with a crosslinking agent, and where the first type of biological sample and the second type of biological sample are sample types that are not the same sample type. The field of this invention relates to computer systems and methods for use in training a classifier for determining a phenotypic characterization of both a first type of biological sample and a second type of biological sample from among a set of phenotypic characterizations using the highly-correlated genes.

2. BACKGROUND OF THE INVENTION

The development of clinical diagnostic tests using paraffin-embedded, formalin-fixed biological samples and microarray gene expression has been hampered by the need to acquire large training datasets of formalin-fixed paraffin-embedded (FFPE) biological samples for developing the optimal diagnostic models. To date, very few microarray hybridization experiments have been performed using FFPE biological samples, due to RNA damage caused by formalin fixation. Instead, the microarray-based diagnostics have been developed and applied to frozen biological samples, significantly restricting their adoption. Classification of frozen and FFPE specimens is disclosed in, e.g., Ismael et al., *New Engl. J. Med.* 355:1071-1072 (2006); Erlander et al., *J. Clin. Oncolog.* 22:14S (2004); Horlings et al., J. Clin. Oncolog. 26:4435-4441 (2008); and Ma et al., International Publication WO2006/10212, published Oct. 19, 2006.

Generally, attempts made to build classifiers for FFPE biological samples have used genes that were identified using only frozen biological samples. See, e.g., Rimsza et al., 2007 *ASH Annual Meeting Abstracts* 110:23a (2007); Giordano et al., Am. J. Pathology 159:1231-1238 (2001).

Other groups have sought to build classifiers in other platforms. For example, Ma et al. developed a classifier as to tissue of origin based on a PCR platform, but selected the genes based on microarray data on frozen biological samples, choosing only a certain number of top performing genes for use in a RT-PCR classifier. Ma et al., *Arch. Pathol. Lab. Med* 130:465-473 (2006). Also, Tothill et al. disclose a support vector machine trained on frozen biological samples, which classifier is used for classifying both frozen and FFPE biological samples. Tothill et al., Cancer Res. 65:4031-4040 (2005).

Other groups sought to build a classifier for both frozen and FFPE biological samples using microRNA. See, e.g., Xi et al., *RNA* 13:1668-1674 (2007); Rosenfeld et al., *Nature Biotechnology* 26:462-469.

In order to expand the scope of microarray expression diagnostics to fixed biological samples, there is a need for a method of building optimal diagnostic classifiers using a database of expression profiles of frozen biological samples, but which method provides a classifier which can be optimally applied to fixed biological samples. The methods disclosed in this application provide for identifying genes which are highly correlated between frozen and fixed biological samples, whose expression levels can be used for building a classifier for classifying both frozen and fixed biological samples. The expression levels of these highly correlated genes can be used for building a classifier for classifying both frozen and fixed biological samples. Methods for training classifiers using the expression levels of these highly correlated genes also are provided in this application, as well as methods for classifying a frozen or fixed biological sample as to a phenotypic characterization using these classifiers.

Discussion or citation of a reference herein should not be construed as an admission that such reference is prior art to the present invention.

3. SUMMARY OF THE INVENTION

The present invention addresses the shortcomings in the prior art.

In the present invention, systems and computer-implemented methods are provided for identifying a plurality of protein-coding genes whose transcript levels in nucleic acid preparations derived from biological samples are useful for classifying both a first type of biological sample and a second type of biological sample, wherein said first type of biological sample and said second type of biological sample are each a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not the same said sample type. The computer-implemented method comprises identifying a plurality of protein-coding genes, each of which has a transcript with an abundance level in a nucleic acid preparation derived from said first type of biological sample of a matched pair that is correlated with an abundance level of said transcript of said protein-coding gene in a nucleic acid preparation derived from the other member of the matched pair, the other member being said second type of biological sample that is analogous to said first type of biological sample, wherein said abundance levels are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100. Preferably, the abundance levels used to identify the protein coding genes are not standardized abundance levels. In preferred embodiments, the fixed biological sample that has been fixed with a crosslinking agent is a formalin-fixed paraffin-embedded (FFPE) biological sample. Also, in preferred embodiments, the first type of biological sample is a FFPE biological sample. An aspect of the computer-implemented method optionally comprises outputting to a user, a user interface device, a computer readable storage medium, a monitor, a local computer, or a computer that is part of a network; or displaying, the identities of the identified plurality of protein-coding genes.

Systems and computer-implemented methods also are provided for training a classifier useful for classifying as to a phenotypic characterization a biological sample. The computer-implemented method comprises training a classifier for classifying biological samples as to a phenotypic characterization using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples. In preferred embodiments, the fixed biological sample that has been fixed with a crosslinking agent is a FFPE biological sample. Also, in preferred embodiments, the first type of biological sample is a FFPE biological sample. In another aspect, the computer-implemented method optionally comprises outputting to a user, a user interface device, a computer readable storage medium, a monitor, a local computer, or a computer that is part of a network; or displaying, one or more parameters of the classifier. Preferably, the abundance levels from the training biological samples that are used in training a classifier are standardized abundance levels.

Systems and computer-implemented methods also are provided for classifying a test biological sample as to a phenotypic characterization using a classifier. The computer-implemented method comprises: (a) training a classifier for classifying biological samples as to a phenotypic characterization using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples; and (b) processing, using said classifier, abundance levels of respective transcripts of a group of genes in a nucleic acid preparation derived from said test biological sample, wherein said group of genes comprises said protein-coding genes of said set of genes, to classify said test biological sample as to said phenotypic characterization. In preferred embodiments, the fixed biological sample that has been fixed with a crosslinking agent is a FFPE biological sample. Also, in preferred embodiments, the first type of biological sample is a FFPE biological sample. In another aspect, the method optionally comprises outputting to a user, a user interface device, a computer readable storage medium, a monitor, a local computer, or a computer that is part of a network; or displaying, from the classifier an indication of the phenotypic characterization.

In another aspect, the computer-implemented method for classifying a test biological sample as to a phenotypic characterization using a classifier comprises: processing, using said classifier, abundance levels of respective transcripts of a group of genes in a nucleic acid preparation derived from said test biological sample, to classify said test biological sample as to said phenotypic characterization, wherein said classifier is trained according to a method comprising: training said classifier using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples; and wherein said group of genes comprises said protein-coding genes of said set of genes. In preferred embodiments, the fixed biological sample that has been fixed with a crosslinking agent is a FFPE biological sample. Also, in preferred embodiments, the first type of biological sample is a FFPE biological sample. In still another aspect, the method optionally comprises outputting to a user, a user interface device, a computer readable storage medium, a monitor, a local computer, or a computer that is part of a network; or displaying, from the classifier an indication of the phenotypic characterization.

Preferably the methods for classifying provide a result that is a probability that the phenotypic characterization is present in the biological sample or the subject (for example, a human) from which the biological sample is derived. Preferably the probability is expressed as a numeric value.

An aspect of the present invention provides a computer system for performing any of the methods disclosed in this application. The computer system comprises one or more processor units; and one or more memory units connected to the one or more processor units, the one or more memory units containing one or more modules which comprise one or more programs which cause the one or more processor units to execute steps comprising performing the steps of any of the methods disclosed in this application. In the foregoing embodiments, the one or more memory units can contain one or more modules which comprise one or more programs which cause the one or more processor units to optionally execute steps comprising outputting to a user, a user interface device, a monitor, a computer-readable storage medium, a computer-readable memory, or a local or remote computer system; or displaying, a result of the method, for example, as is applicable to the method being executed, the identities of the identified plurality of protein-coding genes, one or more parameters of the trained classifier, or an indication (preferably a probability) of a phenotypic characterization.

Another aspect of the present invention provides a computer-readable medium storing a computer program executable by a computer for performing any of the methods disclosed in this application. A computer program product is provided for use in conjunction with a computer having one or more memory units and one or more processor units, the computer program product comprising a computer readable storage medium having a computer program mechanism encoded thereon, wherein the computer program mechanism can be loaded into the one or more memory units of the computer and cause the one or more processor units of the computer to execute steps comprising performing any of the methods disclosed in this application. In the foregoing embodiments, the computer program mechanism can be loaded into the one or more memory units of said computer and cause the one or more processor units of the computer to optionally execute steps comprising outputting to a user, a user interface device, a monitor, a computer-readable storage medium, a computer-readable memory, or a local or remote computer system; or displaying, a result of the method, for example, as is applicable to the method being executed, the identities of the identified plurality of protein-coding genes, one or more parameters of the trained classifier, or an indication (preferably a probability) of a phenotypic characterization.

In preferred embodiments of the methods and the products described in this application, the fixed biological samples that have been fixed with a crosslinking agent are FFPE biological samples. In preferred embodiments, all the fixed biological samples used or referred to in a method described herein are fixed by the same process, for example, are all FFPE biological samples.

In preferred embodiments of the methods described in this application, one or more, two or more, or all of the steps of the methods are performed by a computer.

4. BRIEF DESCRIPTION OF THE DRAWINGS

Figure 4A:
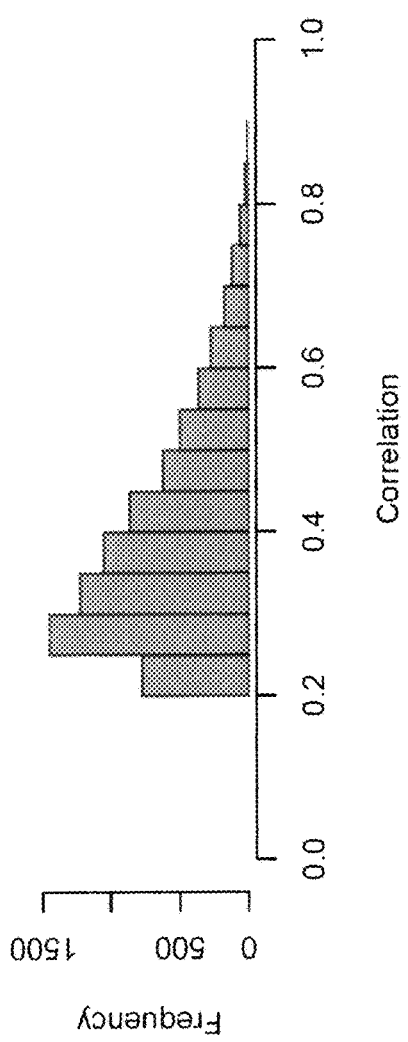
Figure 4B:
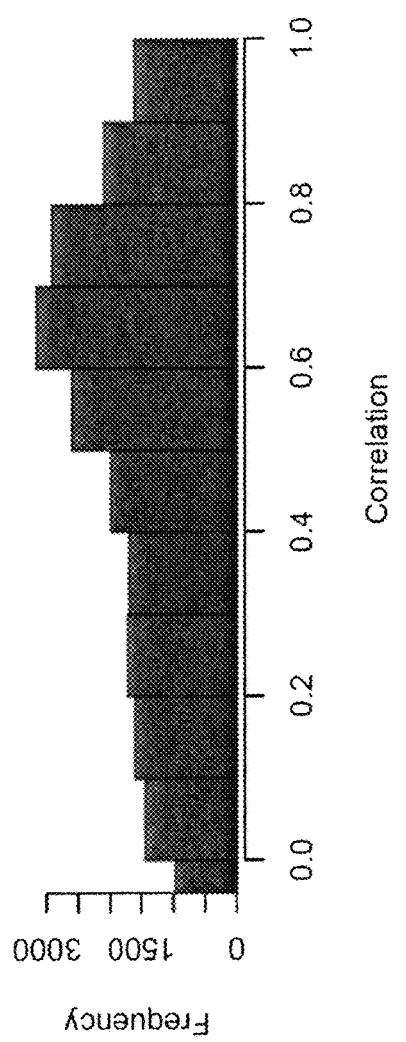

FIG. 4A shows a histogram of values of the Pearson correlation coefficient, in the range from 0.2 to 1.0, computed between abundance levels of transcripts in nucleic acid preparations derived from matched pairs of frozen and FFPE biological samples (which indicates the preservation of the respective RNA in the FFPE biological samples); FIG. 4B shows a histogram of values of the Pearson correlation coefficient, in the range from around 0.0 to 1.0, computed between abundance levels of transcripts in nucleic acid preparations derived from pairs of replicates of frozen biological samples (which indicates the reproducibility of RNA expression in replicates of frozen biological samples). Seventy-five hundred (7500) highly-correlated genes were identified in FIG. 4A.

Figure 5A:
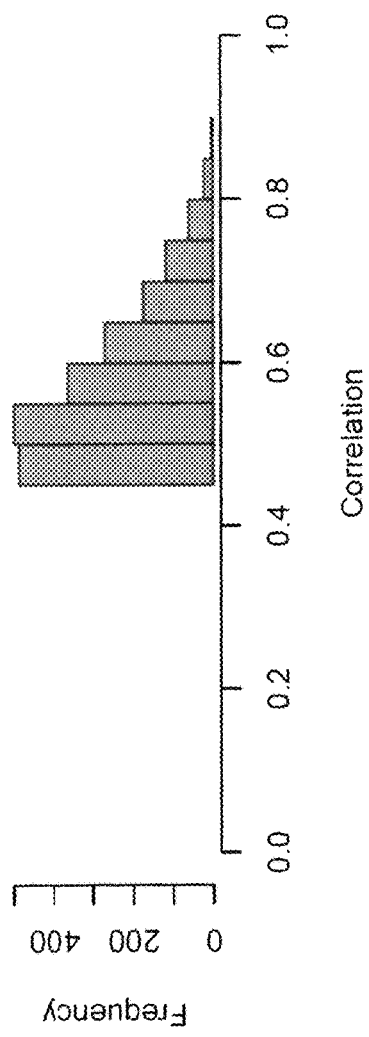
Figure 5B:
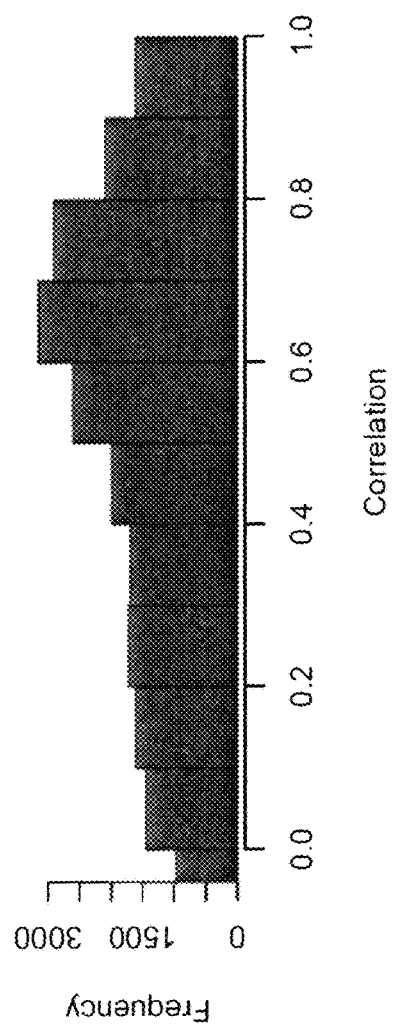

FIG. 5A shows a histogram of values of the Pearson correlation coefficient, in the range from around 0.45 to 1.0, computed between abundance levels of transcripts in nucleic acid preparations derived from matched pairs of frozen and FFPE biological samples (which indicates the preservation of the respective RNA in the FFPE biological samples); FIG. 5B shows a histogram of values of the Pearson correlation coefficient, in the range from around 0.0 to 1.0, computed between abundance levels of transcripts in nucleic acid preparations derived from pairs of replicates of frozen biological samples (which indicates the reproducibility of RNA expression in replicates of frozen biological samples). Two thousand (2000) highly-correlated genes were identified in FIG. 5A.

FIGS. 6A-6F show plots of truth similarity scores and classification error rates with application of candidate classifiers, each built using abundance levels of respective transcripts of differing numbers of highly-correlated genes.

Each data point of a truth score and corresponding error rate in FIGS. 6A-6F is an indicator of the performance of an individual candidate classifier. The candidate classifiers of FIGS. 6A-6C were built using abundance levels of respective transcripts of from 1000 highly-correlated genes up to 2500 highly-correlated genes, as indicated. The candidate classifiers of FIG. 6D were built using abundance levels of respective transcripts of from 1000 highly-correlated genes up to 2000 highly-correlated genes, as indicated. The candidate classifiers of FIG. 6E were built using abundance levels of respective transcripts of from 100 highly-correlated genes up to 1000 highly-correlated genes, as indicated. The candidate classifiers of FIG. 6F were built using abundance levels of respective transcripts of from 100 highly-correlated genes to 500 highly-correlated genes, as indicated.

Figure 7A:
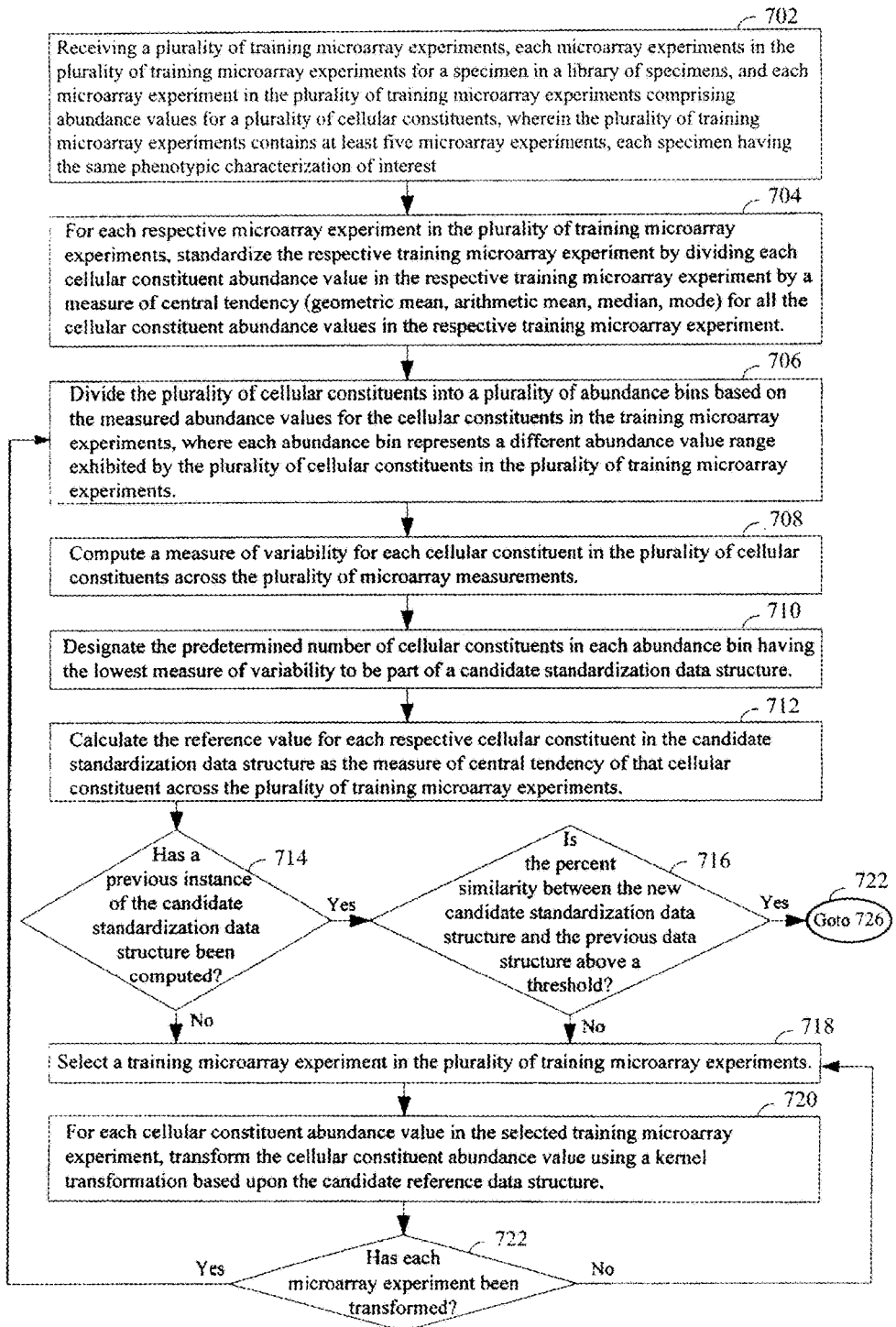
Figure 7B:
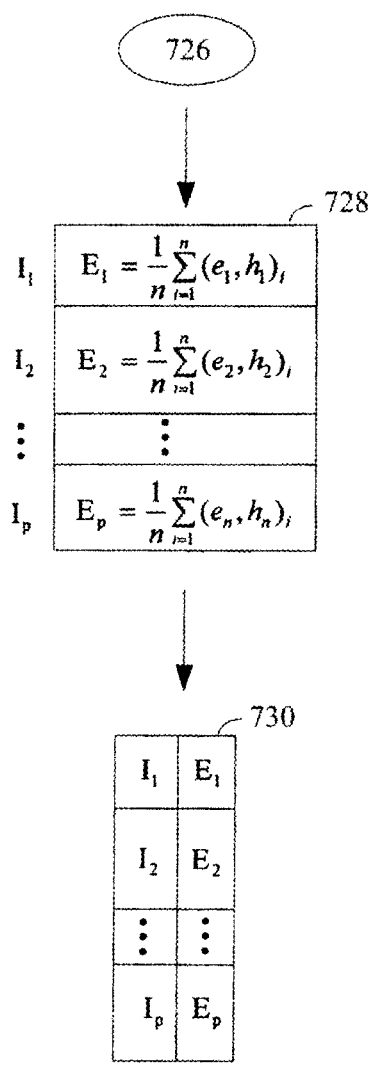

FIGS. 7A-7B illustrate an exemplary method for constructing a standardization data structure for use in standardizing expression profiles comprising abundance levels of transcripts using a kernel transformation.

Figure 8:
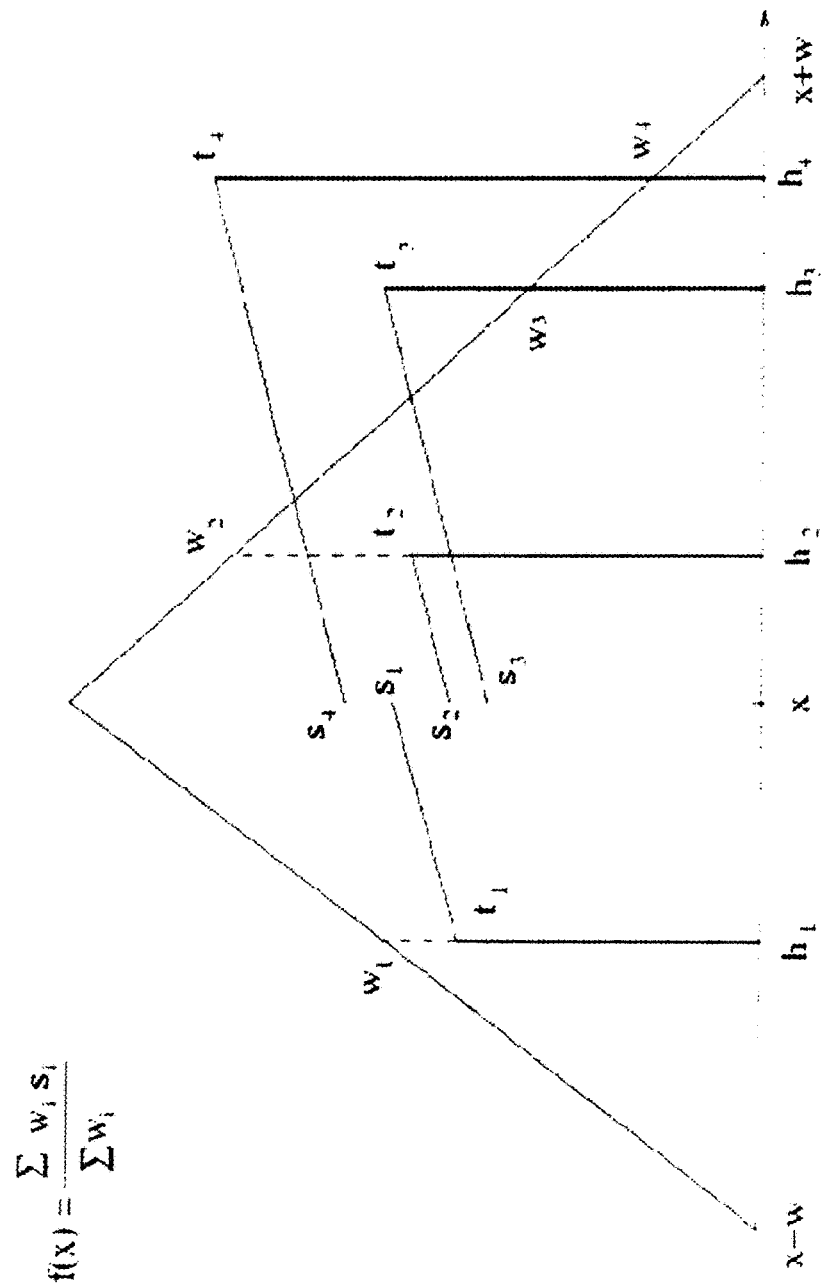

FIG. 8 illustrates a kernel transformation for a given transcript abundance level x, in the method for standardizing abundance levels of transcripts illustrated in FIGS. 7A-7B.

Figure 9A:
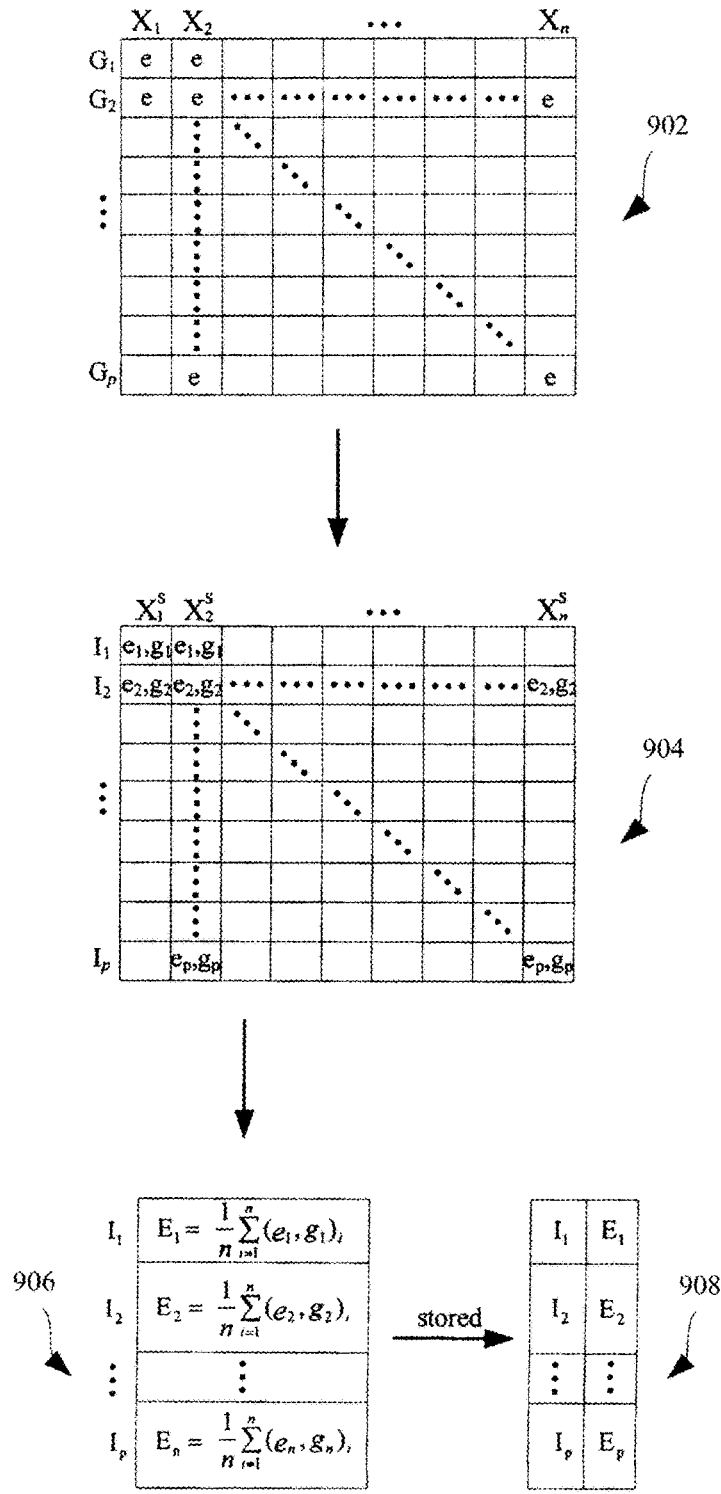
Figure 9B:
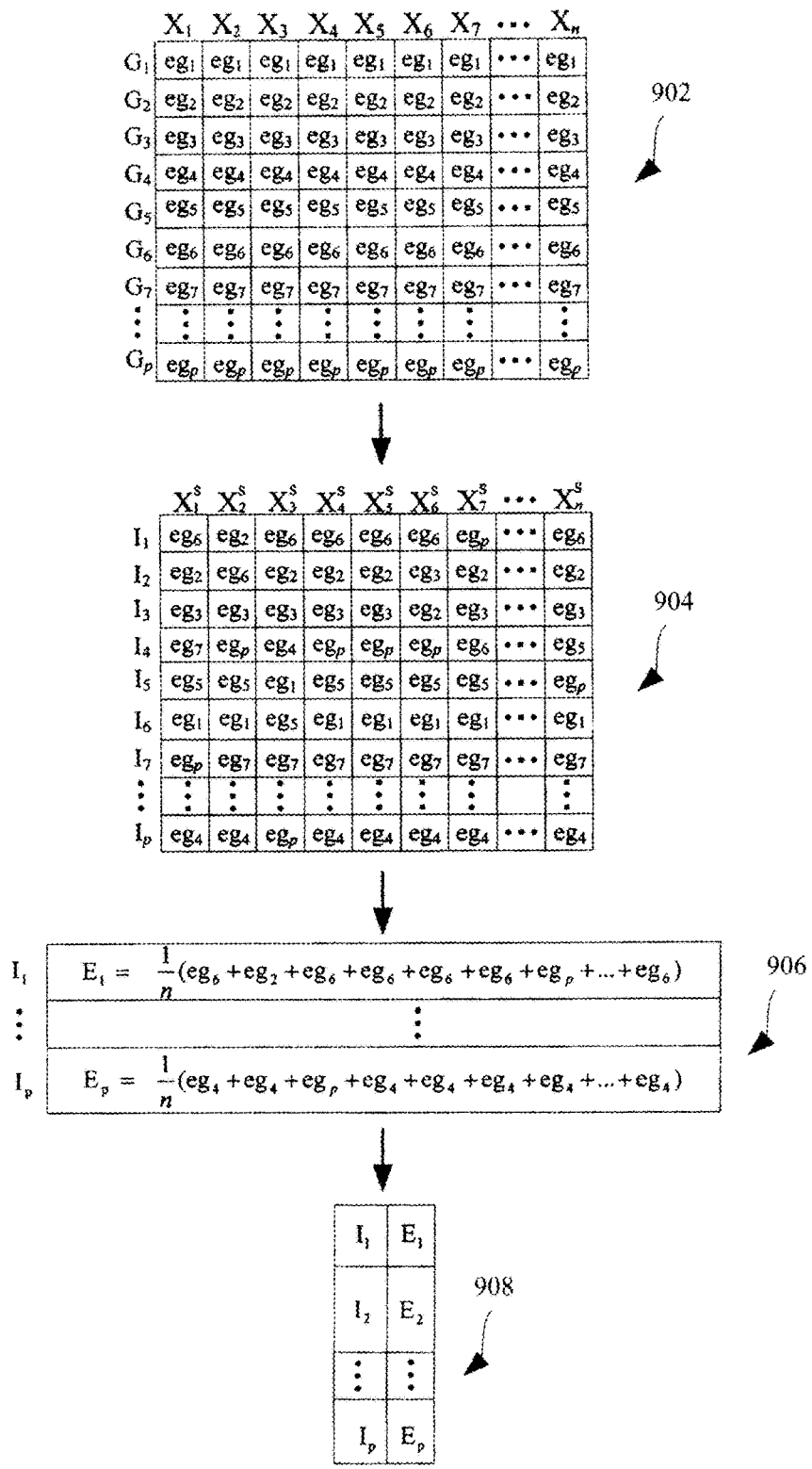

FIGS. 9A-9D illustrate an exemplary method for standardizing expression profiles comprising abundance levels of transcripts. FIG. 9A illustrates an algorithm for constructing a standardization data structure. FIG. 9B illustrates the use of the algorithm of FIG. 9A in constructing a standardization data structure. FIG. 9C illustrates the application of a standardization data structure, constructed in the manner illustrated in FIG. 9A, to a test microarray dataset. FIG. 9C represents the case where each measure of central tendency in a standardization data structure is for a set of transcript abundance levels. Each transcript abundance level in the set is the transcript abundance level of a transcript from a different training microarray dataset in a plurality of training microarray datasets that has the same ranking and the identifier for the corresponding measure of central tendency is the transcript abundance level ranking in the training microarray datasets. FIG. 9D illustrates a specific example of the application of a standardization data structure, constructed in the manner illustrated in FIG. 9A, to a test microarray dataset.

Like reference numerals refer to corresponding parts throughout the several views of the drawings.

5. DETAILED DESCRIPTION OF THE INVENTION

Conventional methods exist for classifying frozen or fresh biological samples as to a phenotypic characterization, such as tumor type, or the tissue of origin of a disease (such as cancer). But these conventional methods generally yield poor results when used to classify biological samples that have been fixed (for example, formalin-fixed or formalin-fixed paraffin-embedded (FFPE) biological samples) due to degradation or damage to RNA caused by fixation in, for example, formalin. Conventional microarray-based diagnostics have been developed for application to frozen specimens, which significantly restricts their adoption for application to fixed biological samples. Specifically, conventional methods using classifiers trained on gene expression levels derived from frozen biological samples generally perform poorly when classifying using gene expression levels from fixed biological samples that have been fixed with a cross-linking agent (for example, formalin-fixed or FFPE biological samples). Indeed, the development of clinical diagnostic tests using FFPE biological specimens and microarray gene expression has been hampered by the need to acquire large training datasets of FFPE biological samples for developing the optimal diagnostic models. The present invention overcomes these limitations of conventional methods by providing systems and methods applicable to classification of biological samples of different sample types, such as frozen and fixed biological specimens. In particular, the invention provides systems and methods for identifying a set of protein-coding genes whose relative expression levels are substantially and similarly unaffected by the preservation or fixation process applied to a biological sample of two different sample types, i.e., a first type of biological sample and to a second type of biological sample, where the first type of biological sample and the second type of biological sample are sample types that are not of the same sample type. That is, genes are identified which have transcripts that either (i) are substantially preserved in the first type of biological sample and the second type of biological sample (i.e., preserved by both the preservation or fixation process applied to the first type of biological sample and the preservation or fixation process applied to the second type of biological sample, or lack thereof in the case of a fresh biological sample, or (ii) are similarly affected by the preservation or fixation process applied to the first type of biological sample and the preservation or fixation process applied to the second type of biological sample (such as but not limited to transcripts whose abundance levels are similarly degraded).

The present invention relates to systems and computer-implemented methods for identifying a set of genes whose expression levels are highly correlated between two different types of biological samples—a first type of biological sample and a second type of biological sample, where the first type of biological sample and the second type of biological sample are sample types that are not the same sample type. Examples of sample types include fresh biological samples, frozen biological samples, biological samples that have been preserved with a non-crosslinking preservative (discussed in Section 5.1, below), and fixed biological samples that have been fixed with a crosslinking agent (discussed in Section 5.1, below). Therefore, for example, if the first type of biological sample is a fixed biological sample that has been fixed with a crosslinking agent (such as a FFPE biological sample), then the second type of biological sample is a sample type selected from the group consisting of: a fresh biological sample, a frozen biological sample, and a biological sample that has been preserved with a non-crosslinking preservative. As another example, if the first type of biological sample is a biological sample that has been preserved with a non-crosslinking preservative, then the second type of biological sample is a sample type selected from the group consisting of: a fresh biological sample, a frozen biological sample, and a fixed biological sample that has been fixed with a crosslinking agent. In a preferred embodiment, the first type of biological sample is a FFPE biological sample, and the second type of biological sample is a frozen biological sample. Abundance levels of transcripts of the identified highly-correlated genes in training biological samples that are of the same sample type(s) as the first type of biological sample and the second type of biological sample used to identify the highly-correlated genes can be used to train a classifier for use in classifying as to a phenotypic characterization any test biological sample which is of the same sample type as the first type of biological sample or the second type of biological sample which were used to identify the highly-correlated genes. Examples of a phenotypic characterization include but are not limited to tumor type, or the tissue of origin of a disease (such as of a cancer of unknown primary), the presence or absence of a disease or disorder, the identity of an infectious agent or strain of infectious agent responsible for the presence of an infection, the response to a treatment, the aggressiveness or stage of a disease, the tissue type, gender, and age (as discussed in Section 5.7, below).

Computer-implemented methods and systems are disclosed in this application for identifying a plurality of protein-coding genes, each of which has a respective transcript with an abundance level in a nucleic acid preparation derived from a first type of biological sample that is correlated with an abundance level of said respective transcript of said protein-coding gene in a nucleic acid preparation derived from an analogous said second type biological sample, where the first type of biological sample and the analogous second type of biological sample are sample types that are not of the same sample type. In preferred embodiments, the first type of biological sample is a FFPE biological sample and the analogous second type of biological sample is an analogous frozen biological sample. Methods of obtaining abundance levels of transcripts are discussed in Section 5.8, below. The abundance levels are said to be correlated when a measure of similarity between the abundance levels is above a predetermined threshold. These identified genes are referred to in this application as "highly-correlated" genes (as discussed in Section 5.2, below). Methods of computing a measure of similarity and determining a predetermined threshold are disclosed in Sections 5.10 and 5.2, respectively. The first type of biological sample and analogous second type of biological sample used for identifying the highly-correlated genes are a matched pair (as discussed in Section 5.2, below). The highly-correlated genes can be used to train classifiers for classifying, as to a phenotypic characterization, biological samples of the same type as that of the first type of biological sample or the analogous second type of biological sample which were used to identify the highly-correlated genes. Therefore, the invention has wide-ranging utility in the art.

The present invention also relates to systems and computer-implemented methods for training classifiers useful for classifying, as to a phenotypic characterization, both biological samples of a first sample type and biological samples of a second sample type, where the first type of biological sample and the second type of biological sample are sample types that are not of the same sample type. Examples of a phenotypic characterization include but are not limited to tumor type, or the tissue of origin of a disease (such as of a cancer of unknown primary), the presence or absence of a disease or disorder, the identity of an infectious agent or strain of infectious agent responsible for the presence of an infection, the response to a treatment, the aggressiveness or stage of a disease, the tissue type, gender, and age. The classifier is trained using respective abundance levels of transcripts of a set of genes in nucleic acid preparations derived from a plurality of training biological samples, the set of genes comprising, consisting essentially of, or consisting of, highly-correlated genes. The highly-correlated genes are protein-coding genes, each of which has a respective transcript that has an abundance level in a nucleic acid preparation derived from a first type of biological sample that is correlated with an abundance level of that transcript in a nucleic acid preparation derived from an analogous second type of biological sample, where the abundance levels are said to be correlated when a measure of similarity between the abundance levels is above a predetermined threshold. The first type of biological sample and analogous second type of biological sample that are used to identify the highly-correlated genes form a matched pair. The measure of similarity is computed over a set M of matched pairs, where the number of matched pairs in set M is at least 5, at least 10, at least 20, at least 30, at least 50, at least 80, or at least 100. In preferred embodiments, the first type of biological sample is a FFPE biological sample and the analogous second type of biological sample is an analogous frozen biological sample. The training biological samples preferably are: (i) biological samples of the same sample type as the first type of biological sample of the matched pairs that were used to identify the highly-correlated genes, (ii) biological samples of the same sample type as the analogous second type of biological sample of the matched pairs that were used to identify the highly-correlated genes, or (iii) a mixture of (i) and (ii). The classifier is trained to classify, as to a phenotypic characterization, preferably: (i) a test biological sample of the same sample type as the first type of biological sample of the matched pairs that were used to identify the highly-correlated genes, or (ii) a test biological sample of the same sample type as the analogous second type of biological sample of the matched pairs that were used to identify the highly-correlated genes. The degree of nucleic acid preservation in frozen biological samples, fresh biological samples, and biological samples that have been preserved with a non-crosslinking preservative, can be appreciably greater than the degree of nucleic acid preservation in fixed biological samples that have been fixed with a crosslinking agent. Therefore, in some embodiments where the first type of biological sample of the matched pairs used to identify the highly-correlated genes is a fixed biological sample that has been fixed with a crosslinking agent, a classifier trained using abundance levels from training biological samples of sample type of: a fresh biological sample, a frozen biological sample, or a biological sample that has been preserved with a non-crosslinking preservative, can be used to classify a test biological sample which is a fresh biological sample, a frozen biological sample, a biological sample that has been preserved with a non-crosslinking preservative, or a fixed biological sample that has been fixed with the same crosslinking agent. In other embodiments where the first type of biological sample of the matched pairs used to identify the highly-correlated genes is a fixed biological sample that has been fixed with a crosslinking agent, a classifier trained using abundance levels from training biological samples which are fixed biological samples that have been fixed with a crosslinking agent, can be used to classify a test biological sample which is a fresh biological sample, a frozen biological sample, a biological sample that has been preserved with a non-crosslinking preservative, or a fixed biological sample that has been fixed with the same crosslinking agent. In a specific embodiment, a classifier which is trained using expression levels of transcripts of the highly-correlated genes in frozen biological samples and/or FFPE biological samples is used to classify either frozen biological samples or FFPE biological samples. In some embodiments, the classifier can be trained using expression levels of transcripts of the highly-correlated genes in training biological samples, which training biological samples are a mixture of frozen biological samples and fixed biological samples (such as formalin-fixed or FFPE biological samples), which classifier can then be used to classify frozen and fixed biological samples (such as formalin-fixed or FFPE biological samples). In some embodiments, a classifier trained using expression levels of transcripts of the highly-correlated genes in frozen biological samples according to the methods disclosed in this application is used to classify fixed biological samples (such as formalin-fixed or FFPE biological samples). In other embodiments, a classifier trained using expression levels of transcripts of the highly-correlated genes in fixed biological samples (such as formalin-fixed or FFPE biological samples) according to the methods disclosed in this application is used to classify frozen biological samples. As yet another example, a classifier trained using expression levels of transcripts of the highly-correlated genes in biological samples that have been preserved with a non-crosslinking preservative (such as but not limited to RNAlater® (Ambion, Inc., Austin, Tex.)) according to the methods disclosed in this application is used to classify fixed biological samples that have been fixed with a crosslinking agent (such as but not limited to FFPE biological samples). Such classifiers include, but are not limited to, a neural network and a support vector machine, as discussed in Section 5.11, below. In specific embodiments, the set of genes whose expression levels are used for training the classifier contains at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes. In the foregoing embodiments, the highly-correlated genes can comprise at least 10%, at least 25%, at least 30%, at least 50%, at least 75%, at least 80%, at least 90%, at least 95%, at least 99%, or all of the set of genes whose expression levels can be used for training the classifier. In the foregoing or other embodiments, the classifier can be trained using expression levels of transcripts of the highly-correlated genes in at least 5, at least 7, at least 10, at least 15, at least 20, at least 25, at least 30, at least 40, at least 50, at least 100, at least 200, at least 500, at least 750, at least 1000, at least 1500, or at least 2000 training biological samples.

The invention also relates to systems and methods for classifying, using a classifier, a test biological sample as to a phenotypic characterization, including but not limited to tumor type, or the tissue of origin of a disease (such as of a cancer of unknown primary), the presence or absence of a disease or disorder, the identity of an infectious agent or strain of infectious agent responsible for the presence of an infection, the response to a treatment, the aggressiveness or stage of a disease, the tissue type, gender, and age. The classifier is trained using respective abundance levels of transcripts of a set of genes in nucleic acid preparations derived from a plurality of training biological samples, the set of genes comprising highly-correlated genes. In some embodiments, the method comprises the steps of training a classifier using respective abundance levels of transcripts of a set of genes in nucleic acid preparations derived from a plurality of training biological samples, and processing the respective abundance levels of transcripts of a group of genes in a nucleic acid preparation derived from a test biological sample using the trained classifier. The set of genes used for training the classifier comprises highly-correlated genes, where the highly-correlated genes are protein-coding genes whose respective transcript has an abundance level in a nucleic acid preparation derived from a first type of biological sample that is correlated with an abundance level of that transcript in a nucleic acid preparation derived from an analogous second type of biological sample, where the first type of biological sample and the second type of biological sample are not of the same sample type, and where the abundance levels are said to be correlated when a measure of similarity between the abundance levels is above a predetermined threshold. The first type of biological sample and analogous second type of biological sample that are used to identify the highly-correlated genes form a matched pair. The measure of similarity is computed over a set M of matched pairs, where the number of matched pairs in set M is at least 5, at least 10, at least 20, at least 30, at least 50, at least 80, or at least 100. Examples of sample types include fresh biological samples, frozen biological samples, biological samples that have been preserved with a non-crosslinking preservative, or fixed biological samples that have been fixed with a crosslinking agent. The training biological samples preferably are: (i) biological samples of the same sample type as the first type of biological sample that was used to identify the highly-correlated genes. (ii) biological samples of the same sample type as the analogous second type of biological sample that was used to identify the highly-correlated genes, or (iii) a mixture of (i) and (ii). The trained classifier preferably classifies as to a phenotypic characterization: (i) a test biological sample of the same sample type as the first type of biological sample that was used to identify the highly-correlated genes, or (ii) a test biological sample of the same sample type as the analogous second type of biological sample that was used to identify the highly-correlated genes. The training biological samples are derived from subjects having one or more of the phenotypic characterizations of interest (for which it is desired to classify test biological samples). In specific embodiments, the set of genes whose expression levels are used for training the classifier contains at least 50 genes, at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes. In the foregoing embodiments, the highly-correlated genes can comprise at least 10%, at least 25%, at least 30%, at least 50%, at least 75%, at least 80%, at least 90%, at least 95%, at least 99%, or all of the set of genes whose expression levels are used for training the classifier. The group of genes in a nucleic acid preparation derived from the test biological sample comprises the highly-correlated genes. In preferred embodiments, the first type of biological sample is a FFPE biological sample and the analogous second type of biological sample is an analogous frozen biological sample, and the classifiers can be used to classify frozen biological samples and/or FFPE biological samples. In some embodiments, a classifier trained using expression levels of transcripts of the highly-correlated genes in training biological samples according to the methods disclosed in this application, which training biological samples are a mixture of frozen biological samples and FFPE biological samples, which can then be used to classify frozen and FFPE biological samples. In other embodiments, a classifier trained using expression levels of transcripts of the highly-correlated genes in frozen biological samples according to the methods disclosed in this application is used to classify FFPE biological samples. In yet other embodiments, a classifier trained using expression levels of transcripts of the highly-correlated genes in FFPE biological samples according to the methods disclosed in this application is used to classify frozen biological samples. In other embodiments, a classifier trained using expression levels of transcripts of the highly-correlated genes in biological samples that have been preserved with a non-crosslinking preservative (such as but not limited to RNAlater® (Ambion, Inc., Austin, Tex.)) according to the methods disclosed in this application is used to classify fixed biological samples that have been fixed with a crosslinking agent (such as but not limited to formalin or glutaraldehyde). In yet other embodiments, a classifier trained using expression levels of transcripts of the respective highly-correlated genes in fixed biological samples that have been fixed with a crosslinking agent (such as but not limited to formalin or glutaraldehyde) according to the methods disclosed in this application is used to classify biological samples that have been preserved with a non-crosslinking preservative (such as but not limited to RNAlater® (Ambion, Inc., Austin, Tex.)). In the foregoing or other embodiments, the classifier can be trained using expression levels of transcripts of the highly-correlated genes in at least 5, at least 7, at least 10, at least 15, at least 20, at least 25, at least 30, at least 40, at least 50, at least 100, at least 200, at least 500, at least 750, at least 1000, at least 1500, or at least 2000 training biological samples.

Figure 1:
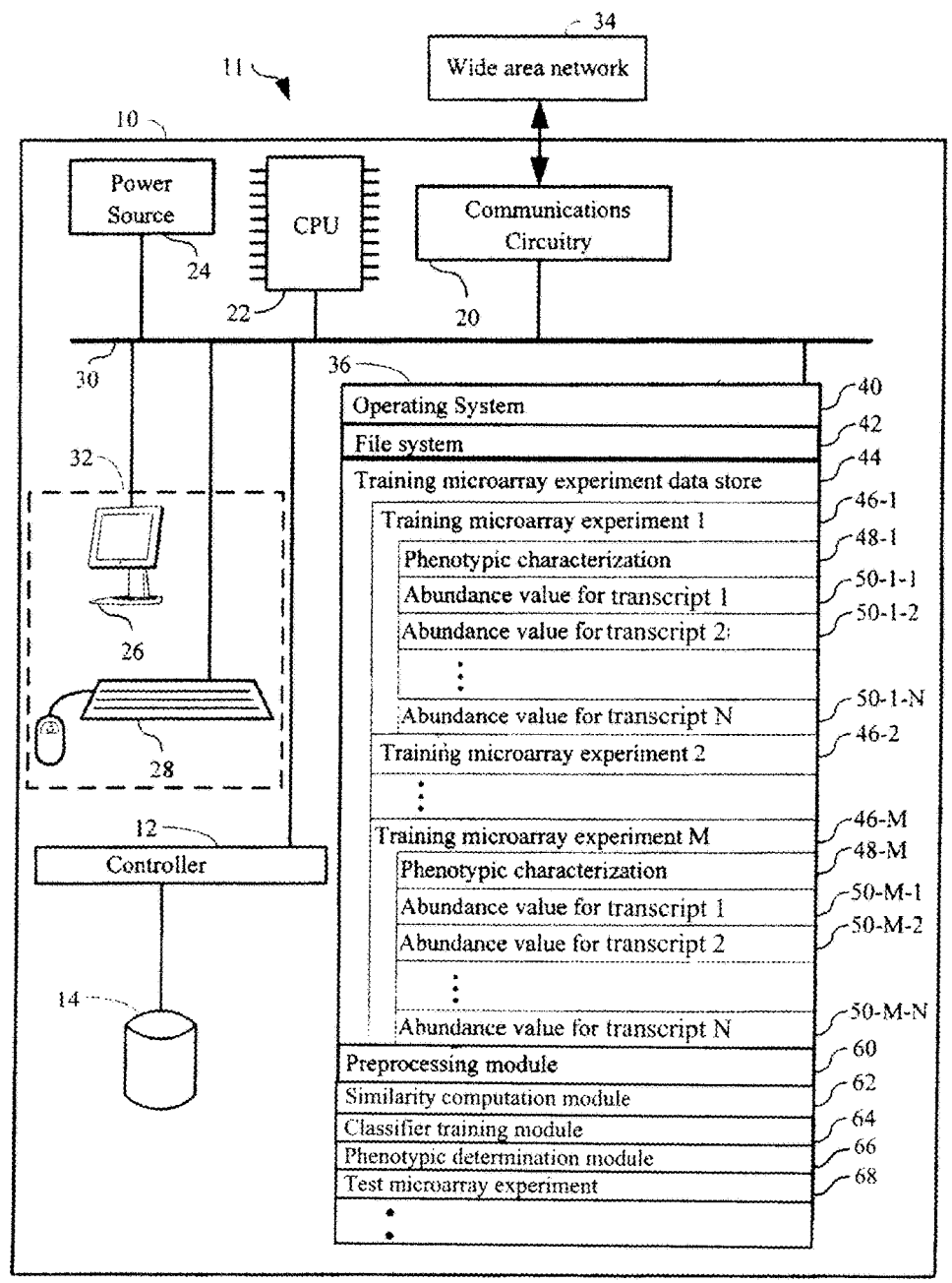
FIG. 1 shows an exemplary computer system in accordance with an embodiment of the present invention.

FIG. 1 details an exemplary system 11 for use in determining a phenotypic characterization of a sample from among a plurality of phenotypic characterizations in accordance with the methods of the present invention. The system preferably comprises a computer system 10 having:

- central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (for example, keyboard 28, a mouse) and a display 26 or other output device;
- a network interface card 20 (communications circuitry) for connecting to any wired or wireless communication network 34 (for example, a wide area network such as the Internet);
- a power source 24 to power the aforementioned elements; and
- an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

- a file system 42 for controlling access to the various files and data structures used by the present invention;
- training microarray experiment data store 44 that comprises data from training microarray experiments 46 that are used in determining a phenotypic characterization of a sample from among a plurality of phenotypic characterizations;
- an optional preprocessing module 60 that is optionally used to preprocess training microarray experiments 46;
- a similarity computation module 62 that is used, for example, to determine a measure of similarity between abundance levels of respective transcripts of genes in nucleic acid preparations derived from biological samples;
- a classifier training module 64 that is used for training a classifier for classifying biological samples as to a phenotypic characterization using abundance levels of respective transcripts of a set of genes in nucleic acid preparations derived from a plurality of training biological samples (such as data from training microarray experiments 46); and
- a phenotypic determination module 66 that is used to determine a phenotypic characterization of a sample from among a plurality of phenotypic characterizations.

While abundance levels of transcripts are described herein in relation to FIG. 1 and elsewhere as being derived from microarray experiments, it will be clear to one skilled in the art that microarray experiments can, but need not be, used to obtain such abundance data. Such abundance data can be obtained by any method known in the art, including but not limited to microarray experiments, RT-PCR, and SAGE (serial analysis of gene expression).

As illustrated in FIG. 1, computer 10 comprises a training microarray experiment data store 44. Training microarray experiment data store 44 can be any form of data storage system including, but not limited to, a flat file, a relational database (SQL), or an on-line analytical processing (OLAP) database (MDX and/or variants thereof). In some specific embodiments, training microarray experiment data store 44 is a hierarchical OLAP cube. In some specific embodiments, training microarray experiment data store 44 comprises a star schema that is not stored as a cube but has dimension tables that define hierarchy. Still further, in some embodiments, training microarray experiment data store 44 has hierarchy that is not explicitly broken out in the underlying database or database schema (for example, dimension tables that are not hierarchically arranged). In some embodiments, training microarray experiment data store 44 is a single database that includes training microarray experiments 46. In other embodiments, training microarray experiment data store 44 in fact comprises a plurality of databases that may or may not all be hosted by the same computer 10. In such embodiments, some components of training microarray experiment data store 44 are stored on computer systems that are not illustrated by FIG. 1 but that are addressable by wide area network 34.

In some embodiments, training microarray experiment data store 44 has data of training microarray experiments 46 for at least two phenotypic characterizations, at least three phenotypic characterizations, at least four phenotypic characterizations, at least five different phenotypic characterizations, at least fifteen phenotypic characterizations, at least fifty phenotypic characterizations. In some embodiments, training microarray experiment data store 44 has at least 2, at least 5, at least 8, at least 10, at least twenty-five, at least fifty, at least one hundred, or at least two hundred different training microarray experiments 46 for each such phenotypic characterization.

In some embodiments, training microarray experiment data store 44 and related software modules illustrated in FIG. 1 (for example modules 60, 62, 64 and 66) are on a single computer (for example, computer 10) and in other embodiments training microarray experiment data store 44 and related software modules illustrated in FIG. 1 are hosted by several computers (not shown). In fact, all possible arrangements of training microarray experiment data store 44 and the modules illustrated in FIG. 1 on one or more computers are within the scope of the present invention so long as these components are addressable with respect to each other across computer network 34 or by other electronic means. Thus, the present invention fully encompasses a broad array of computer systems.

As discussed above, system 11 is used to determine a phenotypic characterization of a sample, preferably from among a plurality of phenotypic characterizations in accordance with the methods of the present invention. In some embodiments, prior to determining the phenotypic characterization of the biological sample, abundance data for the biological sample is standardized; in a preferred aspect of these embodiments, the abundance data for the training biological samples used to train the classifier of system 11 are standardized by the same method as is used to standardize the abundance data for the biological sample for which a phenotypic characterization is determined.

As depicted in FIG. 1, in typical embodiments, data for each training microarray experiment 46 comprises a phenotypic characterization 48 of the training biological sample that was used to obtain the data of training microarray experiment 46. Phenotypic characterization 48 is the clinical truth of the training microarray experiment 46. Each training microarray experiment dataset further comprises abundance values 50 for respective transcripts of a plurality of genes in a nucleic acid preparation derived from the biological sample. The abundance values 50 can be direct measurements of amounts of mRNA transcripts, or can be measurements of nucleic acids derived from the respective mRNAs or nucleic acids indicative thereof, such as cDNAs or cRNAs of mRNAs transcribed from a gene, etc. Furthermore, the "abundance value" (or equivalently, "abundance level") is a quantification of an amount of any of the foregoing. The abundance values of transcripts that are used in the methods of the invention are preferably all of the same class of measurements. For example, they are all measured amounts of mRNA, all measured amounts of cDNA, or all measured amounts of cRNA.

As further depicted in FIG. 1, data from a test microarray experiment 68 is found within memory 36. The data from test microarray experiment 68 comprises the set of abundance values of transcripts in a nucleic acid preparation derived from the test biological sample for which phenotypic characterization is sought. The set of abundance values of transcripts is a set of 50 or more elements where each element is an abundance value. In some embodiments the set contains between 100 and 500 abundance values, between 100 and 1000 abundance values, between 100 and 2500 abundance values, between 100 and 5000 abundance values, or between 100 and 7500 abundance values. Therefore, unlike the training microarray experiments 46, there is no phenotypic truth associated with test microarray experiment 68 when the data from test microarray experiment 68 is received by phenotypic determination module 66.

Data from a training microarray experiment 46 and/or data from a test microarray experiment 68 comprise the abundance values from a microarray that is designed to quantify amounts of gene transcripts in a biological sample. Such microarrays are referred to in this application as expression microarrays. Examples of such microarrays include, but are not limited to, the Affymetrix GENECHIP Human Genome U133A 2.0 Array (Santa Clara, Calif.) which is a single array representing 14,500 human genes. In the case of training microarray experiments 46, such values are referred to as abundance values 50 as depicted in FIG. 1. In some embodiments, data from each training microarray experiment 46 and/or data from test microarray experiment 68 comprises the abundance values from any Affymetrix expression (quantitation) analysis array including, but not limited to, the ENCODE 2.0R array, the HuGeneFL Genome Array, the Human Cancer G110 Array, the Human Exon 1.0 ST Array, the Human Genome Focus Array, the Human Genome U133 Array Plate Set, the Human Genome U133 Plus 2.0 Array, the Human Genome U133 Set, the Human Genome U133A 2.0 Array, the Human Genome U95 Set, the Human Promoter 1.0R array, the Human Tiling 1.0R Array Set, the Human Tiling 2.0R Array Set, and the Human X3P Array.

In some embodiments, data from a training microarray experiment 46 and/or data from a test microarray experiment 68 comprises the abundance values from an exon microarray. Exon microarrays provide at least one probe per exon in genes traced by the microarray to allow for analysis of gene expression and alternative splicing. Examples of exon microarrays include, but are not limited to, the Affymetrix GENECHIP® Human Exon 1.0 ST array. The GENECHIP® Human Exon 1.0 ST array supports most exonic regions for both well-annotated human genes and abundant novel transcripts. A total of over one million exonic regions are registered in this microarray system. The probe sequences are designed based on two kinds of genomic sources, i.e. cDNA-based content which includes the human RefSeq mRNAs, GenBank and ESTs from dbEST, and the gene structure sequences which are predicted by GENSCAN, TWINSCAN, and Ensemble. The majority of the probe sets are each composed of four perfect match (PM) probes of length 25 bp, whereas the number of probes for about 10 percent of the exon probe sets is limited to less than four due to the length of probe selection region and sequence constraints. With this microarray platform, no mismatch (MM) probes are available to perform data normalization, for example, background correction of the monitored probe intensities. Instead of the MM probes, the existing systematic biases are removed based on the observed intensities of the background probe probes (BOP) which are designed by Affymetrix. The BOPs are composed of the genomic and antigenomic probes. The genomic BOPs were selected from a research prototype human exon array design based on NCBI build 31. The antigenomic background probe sequences are derived based on reference sequences that are not found in the human (NCBI build 34), mouse (NCBI build 32), or rat (HGSC build 3.1) genomes. Multiple probes per exon enable "exon-level" analysis provide a basis for distinguishing between different isoforms of a gene. This exon-level analysis on a whole-genome scale opens the door to detecting specific alterations in exon usage that may play a central role in disease mechanism and etiology.

In some embodiments, data from a training microarray experiment 46 and/or data from a test microarray experiment 68 comprises the abundance values measured using any of the techniques known in the art for microarrays, some of which are discussed in Section 5.8, below.

In some embodiments, data from a training microarray experiment 46 and/or data from a test microarray experiment 68 comprises a plurality of abundance measurements and wherein the plurality of abundance measurements consists of abundance measurements for hybridization to between 10 oligonucleotides and $5 \times 10^6$ oligonucleotides on the array. In some embodiments, data from a training microarray experiment 46 and/or test microarray experiment 68 comprise a plurality of abundance measurements, wherein the plurality of abundance measurements consists of abundance measurements for hybridization to between 100 oligonucleotides and $1 \times 10^8$ oligonucleotides, between 500 oligonucleotides and $1 \times 10^7$ oligonucleotides, between 1000 oligonucleotides and $1 \times 10^6$ oligonucleotides, or between 2000 oligonucleotides and $1 \times 10^5$ oligonucleotides. In some embodiments, a training microarray experiment 46 and/or a test microarray experiment 68 comprises a plurality of abundance measurements and wherein the plurality of abundance measurements consists of abundance measurements for hybridization to more than 100, more than 1000, more than 5000, more than 10,000, more than 15,000, more than 20,000, more than 25,000, or more than 30,000 oligonucleotides. In some embodiments, each training microarray experiment 46 and/or each test microarray experiment 68 comprises a plurality of abundance measurements and wherein the plurality of abundance measurements consists of abundance measurements for hybridization to less than $1\times10^7$, less than $1\times10^6$, less than $1\times10^5$, or less than $1\times10^4$ oligonucleotides.

In some embodiments, data from a training microarray experiment 46 and/or data from a test microarray experiment 68 comprises a plurality of abundance measurements and wherein the plurality of abundance measurements consists of abundance measurements for between 5 mRNAs and 50,000 mRNAs. In some embodiments, data from a training microarray experiment 46 and/or data from a test microarray experiment 68 comprises a plurality of abundance measurements and wherein the plurality of abundance measurements consists of abundance measurements for between 500 mRNAs and 100,000 mRNAs, between 2000 mRNAs and 80,000 mRNAs, or between 5000 mRNAs and 40,000 mRNAs. In some embodiments, each training microarray experiment 46 and/or each test microarray experiment 68 comprises a plurality of abundance measurements and wherein the plurality of abundance measurements consists of abundance measurements for more than 100 mRNAs, more than 500 mRNAs, more than 1000 mRNAs, more than 2000 mRNAs, more than 5000 mRNAs, more than 10,000 mRNAs, or more than 20,000 mRNAs. In some embodiments, each training microarray experiment 46 and/or each test microarray experiment 68 comprises a plurality of abundance measurements and wherein the plurality of abundance measurements consists of abundance measurements for less than 100,000 mRNAs, less than 50,000 mRNAs, less than 25,000 mRNAs, less than 10,000 mRNAs, less than 5000 mRNAs, or less than 1,000 mRNAs.

In some embodiments, the training microarray experiment data store 44 comprises data from a plurality of training microarray experiments, wherein the plurality of training microarray experiments consists of between 5 training microarray experiments and 100 training microarray experiments. In the same or different embodiments, the plurality of training microarray experiments consists of at least 5, at least 7, at least 10, at least 15, at least 20, at least 25, at least 30, at least 40, at least 50, at least 100, at least 200, at least 500, at least 750, at least 1000, or at least 1500 training microarray experiments. In some embodiments, the plurality of training microarray experiments consists of between 50 training microarray experiments and 100,000 training microarray experiments. In some embodiments, training microarray experiment data store 44 comprises data from a plurality of training microarray experiments, wherein the plurality of training microarray experiments consists of between 500 and 50,000 training microarray experiments. In some embodiments, training microarray experiment data store 44 comprises data from a plurality of training microarray experiments, wherein the plurality of training microarray experiments consists of between 100 training microarray experiments and 35,000 training microarray experiments. In some embodiments, training microarray experiment data store 44 comprises data from a plurality of training microarray experiments, wherein the plurality of training microarray experiments consists of between 50 training microarray experiments and 20,000 training microarray experiments.

In some embodiments, the data from test microarray experiment 68 and/or data from each training microarray experiment 46 is measured from a microarray comprising probes arranged with a density of 100 different probes per 1 $cm^2$ or higher. In some embodiments, the test microarray experiment 68 and/or each training microarray experiment 46 is measured from a microarray comprising probes arranged with a density of at least 2,500 different probes per 1 $cm^2$, at least 5,000 different probes per 1 $cm^2$, or at least 10,000 different probes per 1 $cm^2$. In some embodiments, the data from test microarray experiment 68 and/or data from each training microarray experiment 46 is measured from a microarray comprising at least 10,000 different probes, at least 20,000 different probes, at least 30,000 different probes, at least 40,000 different probes, at least 100,000 different probes, at least 200,000 different probes, at least 300,000 different probes, at least 400,000 different probes, or at least 500,000 different probes.

As used in this application, a microarray is an array of positionally-addressable binding (hybridization) sites on a support, wherein each of such binding sites consists of polynucleotide probes bound to a predetermined region on the support. In a preferred embodiment, the sites are for binding to many of the nucleotide sequences encoded by the genome of a cell or organism, preferably most or almost all of the transcripts of genes or to transcripts of more than half of the genes having an open reading frame in the genome. Microarrays can be made in a number of ways, of which several are described hereinbelow. However produced, preferably microarrays share certain characteristics. The arrays preferably are reproducible, allowing multiple copies of a given array to be produced and easily compared with each other. Preferably, the microarrays are made from materials that are stable under binding (for example, nucleic acid hybridization) conditions. Microarrays are preferably small, for example, between 1 $cm^2$ and 25 $cm^2$, preferably 1 to 3 $cm^2$. However, both larger and smaller arrays (for example, nanoarrays) are also contemplated and deemed included within the term "microarray," and may be preferable, for example, for simultaneously evaluating a very large number or very small number of different probes.

In some embodiments, the data from test microarray experiment 68 and/or data from each training microarray experiment 46 contains measured abundance values from a different biological sample. Such biological samples may be obtained from subjects in order to measure the abundance values for transcripts. Unless otherwise indicated in this application, any biological sample from an organ, tissue, or biological fluid, for example, liver tissue sample, pancreatic tissue sample, soft tissue, muscle tissue, bone tissue, bladder tissue, lung tissue, epithelial tissue, endothelial tissue, blood sample, urine, mucosal swab, etc., obtained from any subject may serve as a biological sample, as long as it contains protein-coding RNA transcripts and thus can serve as the source of a nucleic acid preparation from which abundance levels of RNA transcripts of protein-coding genes can be determined.

In some embodiments, the computer 10 is in electrical communication with the wide area network 34 (for example, the Internet) and the test microarray experiment 68 and/or each training microarray experiment 46 is received from a local or remote computer (not shown) over the wide area network.

Methods for identifying a set of highly-correlated genes are discussed in Section 5.2, below. A metric of similarity is computed between the abundance values of transcripts in nucleic acid preparations derived from a first type of biological sample and the abundance values of respective transcripts in nucleic acid preparations derived from an analogous second type of biological sample. Examples of sample types include but are not limited to fresh biological samples, frozen biological samples, biological samples that have been preserved with a non-crosslinking preservative, or fixed biological samples that have been fixed with a crosslinking agent (described in Section 5.1, below). The first type of biological sample and the analogous second type of biological sample are sample types that are not the same sample type. The first type of biological sample and the analogous second type of biological sample form a matched pair of biological samples. A plurality of highly-correlated genes is identified whose abundance values in the first type of biological sample correlates with their respective abundance values in the second type of biological sample. Whether such a correlation is present is determined by computing a measure of similarity of the abundance values over a population of matched pairs.

A method for use in training a classifier for use in determining a phenotypic characterization of a biological sample from among a set of phenotypic characterizations using the highly-correlated genes is discussed in Section 5.3, below.

Use of the classifier for classifying a test biological sample of unknown phenotypic characterization is discussed in Section 5.4, below.

5.1 Sample Types of Biological Samples

The methods disclosed herein are applicable to a first type of biological sample and a second type of biological sample, where the first type of biological sample and the second type of biological sample are of different sample types. Examples of sample types include but are not limited to fresh biological samples, frozen biological samples, biological samples that have been preserved with a non-crosslinking preservative, and fixed biological samples that have been fixed with a crosslinking agent.

Frozen biological samples can be produced by any method known in the art; preferably those that minimize nucleic acid degradation are used. Frozen biological samples are generally produced by a cryogenic preservation process, where cells or whole tissues are preserved by cooling to low sub-zero temperatures. By way of example but not limitation, the frozen biological samples may be frozen to 77° K. (around −196° C.), the temperature of liquid nitrogen, or 194° K (around −78° C.), the temperature of dry ice.

Non-crosslinking preservatives that can be used to obtain biological samples preserved with a non-crosslinking preservative include but are not limited to RNeasy® (QIAGEN Inc., Valencia, Calif.), RNAlater® (Ambion, Inc., Austin, Tex.), or in the preservative used in the PAXgene™ Blood RNA System (PreAnalytiX GmbH, Switzerland). Examples of other non-crosslinking preservatives are methanol, ethanol, acetone, phenoxyethanol, polyethylene glycol, mixtures of ethyl alcohol and polyethylene glycol, and other preservative solutions containing alcohols, ketones, acids, etc.

Crosslinking agents that can be used to obtain fixed biological samples fixed with a crosslinking agent include but are not limited to in aldehydes (such as but not limited to formalin or glutaraldehyde), oxidizing agents, or other suitable crosslinking agent known in the art. A crosslinking agent fixes a biological sample by creating covalent chemical bonds between proteins in the biological sample.

Aldehydes are commonly used as crosslinking agents. Formaldehyde is commonly available as formalin, a saturated aqueous solution of formaldehyde. It is thought that formaldehyde interacts primarily with the residues of the basic amino acid lysine. Glutaraldehyde is another aldehyde used as a crosslinking agent, which operates by a similar mechanism to formaldehyde. Mixtures of aldehydes, such as mixtures of formaldehyde and glutaraldehyde, also can be used as a crosslinking agent.

Oxidizing agents also can be used as crosslinking agents. An oxidizing fixative reacts with various side chains of proteins and other biomolecules in the biological sample and allow the formation of crosslinks. Examples of crosslinking agents include but are not limited to osmium tetroxide, potassium dichromate, chromic acid, and potassium permanganate.

Fixed biological sample optionally may be embedded, such as but not limited to plastic- or paraffin-embedded. For example, Battifora (U.S. Pat. Nos. 4,820,504 and 5,610,022) discloses tissue embedding, where tissue fragments, often of tumors, are embedded together in a single paraffin block. Furmanski et al. (U.S. Pat. No. 4,914,022) discloses a method of preparing multi-tumor tissue paraffin blocks, where tissue cores are embedded in a paraffin block.

5.2 Methods for Identifying Highly-Correlated Genes

Computer-implemented methods are provided for identifying a plurality of protein-coding genes whose transcript levels in nucleic acid preparations derived from biological samples are useful for classifying both a first type of biological sample and a second type of biological sample, where the first type of biological sample and the second type of biological sample are sample types independently selected from the group consisting of a fresh biological sample, a frozen biological sample, a biological sample that has been preserved with a non-crosslinking preservative, and a fixed biological sample that has been fixed with a crosslinking agent, where the first type of biological sample and the second type of biological sample are sample types that are not the same sample type. In one embodiment, the computer-implemented method comprises identifying a plurality of protein-coding genes, each of which has a respective transcript with an abundance level in a nucleic acid preparation derived from the first type of biological sample that is correlated with an abundance level of the respective transcript of the protein-coding gene in a nucleic acid preparation derived from an analogous second type of biological sample, where the abundance levels are deemed to be correlated if a measure of similarity between the abundance levels is above a predetermined threshold, where the measure of similarity is computed over a set M of matched pairs, and wherein the number of matched pairs in set M is at least 5.

In a preferred embodiment, the abundance levels used to identify the protein-coding genes are not standardized abundance levels.

Figure 2:
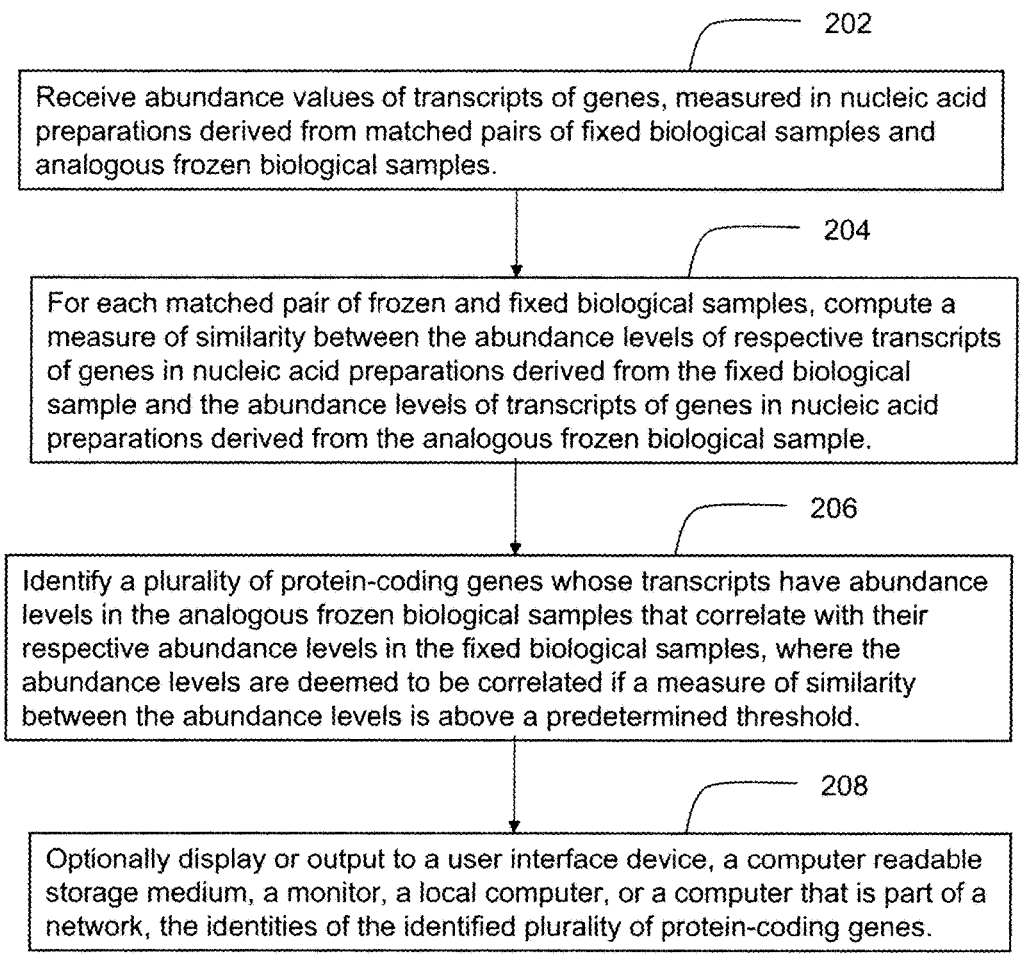
FIG. 2 illustrates an exemplary method for identifying a set of highly-correlated genes in accordance with an embodiment of the present invention.

Referring to FIG. 2, an exemplary method for identifying a set of highly-correlated genes is provided. Abundance levels of transcripts of highly-correlated genes may be used for determining the phenotypic characterization of a test biological sample. While abundance levels of transcripts are described herein in relation to FIG. 2 as being derived from microarray experiments, it will be clear to one skilled in the art that microarray experiments can, but need not be, used to obtain such abundance data. Such abundance data can be obtained by any method known in the art, including but not limited to microarray experiments, RT-PCR, and SAGE (serial analysis of gene expression).

Step 202. In step 202, data from microarray experiments 46-$i$, $i=1, \ldots, N$, of FIG. 1 are received. The data from microarray experiments comprise the abundance values of transcripts of genes in nucleic acid preparations derived from biological samples that are the first type of biological sample and from biological samples that are the second type of biological sample, with each microarray experiment corresponding to individual biological samples, where the first type of biological sample and the second type of biological sample are sample types that are not the same. Thus, for example, if the first type of biological sample is frozen, the second type of biological sample is not frozen. Biological sample types are discussed in Section 5.1.

If the first type of biological sample is the fixed biological sample fixed with a crosslinking agent, preferably all biological samples of said first type used in a method of the invention are fixed with the same crosslinking agent. If the second type of biological sample is the fixed biological sample fixed with a crosslinking agent, preferably all biological samples of said second type used in a method of the invention are fixed with the same crosslinking agent. Similarly, if the first type of biological sample is the biological sample that is preserved with a non-crosslinking preservative, preferably all biological samples of said first type used in a method of the invention are preserved with the same non-crosslinking agent. If the second type of biological sample is the biological sample that is preserved with a non-crosslinking preservative, preferably all biological samples of said second type used in a method of the invention are preserved with the same non-crosslinking agent. In general, it is preferred that all biological samples of said first type of biological sample that are used in a method are prepared in essentially the same manner, and all biological samples of said second type of biological sample that are used in a method are prepared in essentially the same manner.

In some embodiments, microarray experiments 46-*i* are received in the form of an electronic file or signal by computer 10 from a remote location over wide area network 34, where the wide area network is an example of computer network. The remote location may be in the same building as computer 10, in another building as computer 10, in the same city as computer 10, in a different city as computer 10. The remote location may be in the same or different state, country or continent as computer 10. In some embodiments the microarray experiments 46-*i* are encrypted. In some embodiments, the training biological samples are from humans.

Data from microarray experiments 46-*i* comprise abundance levels (also referred to as abundance values) of transcripts in nucleic acid preparations derived from a first type of biological sample and an analogous second type of biological sample. A biological sample that is a sample type that is said first type of biological sample and an analogous biological sample that is a sample type that is said second type of biological sample are referred to in this application as a "matched pair." By "analogous" is meant biological samples which are similar enough such that highly-correlated genes can be identified. Indeed, it is within the discretion of the investigator as to what constitutes a matched pair of frozen and fixed biological samples. Thus, the highly-correlated genes are genes, each of which has a transcript with an abundance level in a nucleic acid preparation derived from a first type of biological sample of a matched pair that is correlated with an abundance level of said transcript in a nucleic acid preparation derived from the other member of the matched pair, the other member being a second type of biological sample, with the first type of biological sample and the second type of biological sample being as defined hereinabove, and where whether such a correlation, between abundance levels of transcripts of genes in nucleic acid preparations derived from the first type of biological sample and from the second type of biological sample of the matched pair, is present is determined by computing a measure of similarity between such abundance values over a population of matched pairs (as discussed hereinbelow).

In specific embodiments, both members of a matched pair are derived from the biological tissue of a single subject, from the same biological tissue type from the same subject, or from the same tissue type of different subjects of the same species. In specific embodiments, a matched pair is a frozen biological sample and a FFPE biological sample both of which are derived from the biological tissue of a single subject, from the same biological tissue type from the same subject, or from the same tissue type of different subjects of the same species. If biological tissue is obtained from a subject, a matched pair can be obtained by treating an aliquot of biological tissue from the subject to one type of fixation or preservation process, while subjecting another aliquot of the same tissue to a different type of fixation or preservation process or to no fixation or preservation process (using it frozen). For example, a matched pair readily can be obtained if an aliquot of biological tissue from a subject is frozen or preserving with a non-crosslinking preservative (such as but not limited to RNeasy® (QIAGEN Inc., Valencia, Calif.) or RNAlater® (Ambion, Inc., Austin, Tex.)), while another aliquot of the same tissue from the same subject is fixed with a crosslinking agent (such as but not limited to formalin, glutaraldehyde, or an oxidizing agent). As another example, a matched pair readily can be obtained if an aliquot of biological tissue from the subject is frozen, while another aliquot of the same tissue is fixed (such as formalin-fixed or FFPE). In some embodiments, a matched pair is a frozen biological sample and a fixed biological sample both of which are derived from subjects of the same species. In some embodiments, the matched pair is obtained from biological tissue of the same tissue type, for example, from the same tumor extracted from a subject. Such tissue may be obtained, for example, from a biopsy of a tumor of a subject. In other embodiments, the matched pair is derived from tissue having the same phenotypic characterization, for example, the same tissue type or the same type of disease (for example, cancer or infectious disease), from different subjects of the same species. The subject or single species under study can be mammalian, for example, human. In some embodiments, the species or subject is mouse, rat, pig, horse, cow, monkey, or dog. The phenotypic characterization can be, for example, a tumor type, or the tissue of origin of a disease (such as of a cancer of unknown primary), the presence or absence of a disease or disorder, the identity of an infectious agent or strain of infectious agent responsible for the presence of an infection, the response to a treatment, the aggressiveness or stage of a disease, the tissue type, age, gender, or any phenotypic characterization described in this application or known in the art. For example, the matched pair may be derived from the same tissue type obtained from a number of subjects having the same phenotypic characterization. Matched pairs may be derived from a pooled sample of different tissue types obtained from a number of subjects having the same phenotypic characterization, wherein some of the pooled sample is treated to become the first type of biological sample and some is treated to become the second type of biological sample. In some embodiments the tissue type is liver, brain, heart, skeletal muscle, white adipose, blood, lung, kidney, bone marrow, breast, kidney, blood, bone marrow, cartilage, colon, embryo, gut, hair root, muscle, oocytes, pancreas, placenta, retina, skin, testicles, or a tumor or a tumor tissue type of interest. In some embodiments, a matched pair is derived from the same cell line. In some embodiments, a matched pair is of a single cell type. In some embodiments, the cell type is amniocytes, B-cells, blastocysts, bronchioalveolar cells, CD34+ cells, cervical cancer cells, chondrocytes, colon carcinoma cells, fibroblasts, hepatocytes, keratinocytes, Langerhans cells, leucocytes, leukemia cells, lymphoblast, lymphocytes, lymphoid cells, monocytes, neutrophils, oocytes, peripheral blood mononuclear cells (PBMC), peritoneal exudate cells, platelets, stem cells, T-cells, or umbilical vein endothelial cells. In some embodiments, the matched pairs are derived from biological samples from multiple tissue types.

For identifying highly-correlated genes, the correlation of the abundance level of a transcript in a nucleic acid preparation derived from a first type of biological sample with its respective abundance level in a nucleic acid preparation derived from an analogous second type of biological sample is computed over a population of matched pairs. In specific embodiments, the number of matched pairs of a first type of biological sample and an analogous second type of biological sample in the population of matched pairs is at least 5, at least 10, at least 20, at least 30, at least 50, at least 80, or at least 100 matched pairs. The number of matched pairs of a first type of biological sample and an analogous second type of biological sample in the population of matched pairs is at the discretion of the investigator.

In some embodiments, the training biological samples collectively have multiple phenotypic characterizations, for example, different types of cancer. Examples of types of cancer include but not limited to bladder, breast, cholangiocarcinoma/gallbladder, central nervous system, colorectal, endometrial, gastric, germ cell, head and neck squamous cell carcinomas (SCC), malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid. Additionally, a training biological sample may exhibit not only one phenotypic characterization, but more than one phenotypic characterization. In addition, training biological samples may be pooled together from biological samples from different subjects each having one or more phenotypic characterizations of interest.

In some embodiments, the abundance levels of transcripts in nucleic acid preparations derived from the biological samples are represented by an expression profile. An expression profile can be represented by the vector p, $p=[p_1, \ldots p_i, \ldots p_n]$ where $p_i$ is the abundance level of the i'th component, for example, the transcript level of gene i. In specific embodiments, n is more than 2, more than 10, more than 100, more than 200, more than 500, more than 1000, more than 2000, more than 2500, more than 7500, more than 10,000, more than 20,000, more than 25,000, or more than 35,000.

Step 204.

In step 204, the correlation between abundance levels of transcripts of genes in nucleic acid preparations derived from the first type of biological sample and from the analogous second type of biological sample is quantified by computation of a similarity metric between their abundance values over a population of matched pairs. In some embodiments, similarity computation module 62 is used to determine a measure of similarity between abundance levels of respective transcripts of genes in nucleic acid preparations derived from the first type of biological sample and from the analogous second type of biological sample of the matched pairs.

In some embodiments, for each transcript i, the correlation is quantified by computation of a similarity metric $sim(p_{i_1})$, where $p_{i_1}$ represents abundance levels of transcript i in nucleic acid preparations derived from the first type of biological sample of the matched pairs in the population of matched pairs (i.e., the i'th component of the expression profiles p from the first type of biological sample of the matched pairs), and $p_{i_2}$ represents abundance levels of transcript i in nucleic acid preparations derived from the analogous second type of biological sample of the matched pairs in the population of matched pairs (i.e., the i'th component of the expression profiles p from the analogous second type of biological sample of the matched pairs). In the foregoing embodiments, the first type of biological sample of the matched pairs in the population of matched pairs are preferably all of the same sample type, and the analogous second type of biological sample of the matched pairs in the population of matched pairs are preferably all of the same sample type (which differs from the sample type of the first type of biological sample of the matched pairs).

One way to compute the similarity metric $sim(p_{i_1}, p_{i_2})$ is to compute the Pearson correlation coefficient between the abundance levels corresponding to each respective transcript i over the population of matched pairs. However, there are many ways in which correlation between the variance in abundance values derived from the first type of biological sample and the analogous second type of biological sample can be quantified. Indeed, any statistical method in the art for determining the probability that two datasets are related may be used in accordance with the methods of the present invention in order to identify whether there is a correlation between the abundance values derived from the first type of biological sample and the analogous second type of biological sample. Other methods for determining the measure of similarity are discussed in Section 5.10, below.

In preferred embodiments, the correlation is computed over the non-standardized abundance levels of transcripts in nucleic acid preparations derived from the biological samples. In other embodiments, a standardization technique (such as discussed in Section 5.9, below) may be applied to the abundance values of transcripts in nucleic acid preparations derived from the biological samples prior to computation of the correlation.

Step 206.

In step 206, a plurality of protein-coding genes are identified having transcripts whose abundance levels in a nucleic acid preparation derived from the first type of biological sample of the matched pairs are highly-correlated with the respective abundance levels of the transcripts in a nucleic acid preparation derived from the analogous second type of biological sample of the matched pairs. The plurality of highly-correlated protein coding genes is identified from among the plurality of candidate protein-coding genes received in Step 202. In some embodiments, the plurality of highly-correlated protein-coding genes is at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes.

A gene is identified as a "highly-correlated" gene if a measure of similarity between the abundance level of the transcript of the gene in nucleic acid preparations derived from the first type of biological sample of the matched pairs and the abundance level of the transcript of the gene in nucleic acid preparations derived from the analogous second type of biological sample of the matched pairs in the population of matched pairs is above a predetermined threshold. The predetermined threshold provides an indication of the level of correlation that is representative of an expected level of variation of the abundance levels of the transcripts in nucleic acid preparations derived from the biological sample as a result of the same preservation process being applied to the biological samples.

In some embodiments, a value of the correlation of the abundance levels of transcripts among a number of pairs of replicate biological samples is used as a basis for determining the predetermined threshold. In some embodiments, the replicate biological samples are of the same sample type as the member of the matched pairs that is of the sample type that generally preserves nucleic acids better or that is more readily available than the other member of the matched pairs. For example, nucleic acid generally is better preserved in a frozen or fresh biological sample or a biological sample preserved with a non-crosslinking preservative, than in a fixed biological sample that has been fixed with a crosslinking agent (such as formalin, glutaraldehyde, or an oxidizing agent). Therefore, in embodiments where one member of the matched pairs in the population of matched pairs is a fixed biological sample that has been fixed with a crosslinking agent, the replicate biological samples are preferably replicates of the biological samples that have been preserved with a non-crosslinking preservative, replicates of the fresh biological samples, or replicates of the frozen biological samples, depending on what is the sample type of the analogous other biological sample of the matched pairs. In a specific embodiment where each of the matched pairs in the population of matched pairs is a FFPE biological sample and an analogous frozen biological sample, the replicate biological samples preferably are replicates of the frozen biological samples. In another embodiment, the replicate biological samples are of the same sample type as the member of the matched pairs for which training biological sample of the same sample type are more readily available. For example, in an embodiment where each of the matched pairs in the population of matched pairs is a FFPE biological sample and an analogous frozen biological sample, where frozen biological samples are more readily available than FFPE biological samples, the replicate biological samples are preferably replicates of the frozen biological samples.

The correlation of the abundance levels of transcripts among pairs of replicate biological samples is used as a reference point to determine the magnitude of correlation (i.e., value of the measure of similarity) which indicates adequate preservation of transcript expression in the first type of biological sample and the second type of biological sample. The use of pairs of replicate biological samples can simplify this process of setting the predetermined threshold by making it more straight-forward to determine the number of genes useful for training the classifiers and for classification of biological samples. In some embodiments, the replicate biological samples of each pair of replicate biological samples are both of biological samples obtained from the same tissue type from a different subject of the same species as the subjects that provided the analogous frozen biological samples of the matched pairs. In the foregoing embodiment, each pair of replicate biological samples is obtained by dividing a biological sample (from the different subject) into (two or more) aliquots. In some embodiments, the replicate biological samples can be obtained by dividing into aliquots biological samples from the same subjects that provided the biological samples of same sample type in the matched pairs. In a specific embodiment where each of the matched pairs in the population of matched pairs is a FFPE biological sample and a frozen biological sample, the replicates of frozen biological sample are obtained by dividing into aliquots frozen biological samples from the same subjects that provided the analogous frozen biological samples of the matched pairs. In another embodiment where each of the matched pairs in the population of matched pairs is a FFPE biological sample and a frozen biological sample, the replicates of frozen biological sample are obtained by dividing into aliquots frozen biological samples from different subjects of the same species as the subjects that provided the analogous frozen biological samples of the matched pairs. In a specific embodiment where each of the matched pairs in the population of matched pairs is a FFPE biological sample and a frozen biological sample, the replicates of frozen biological samples can be obtained by dividing a fresh biological sample into aliquots, with each aliquots being frozen to provide the replicate frozen biological sample.

The correlation of the abundance levels of transcripts over a number of pairs of replicate biological samples can be computed similarly to the similarity metric described in Step 204 in connection with the matched pairs of biological samples. That is, for each transcript i, the correlation among the pairs of replicates may be quantified by computation of a similarity metric $sim(p_{ir_1}, p_{ir_2})$, where $p_{ir_1}$ represents abundance levels of transcript i in nucleic acid preparations derived from a replicate biological sample of each pair of replicate biological samples, and $p_{ir_2}$ represents abundance levels of transcript i in nucleic acid preparations derived from the other replicate biological sample of each pair of replicate biological samples. Other methods of computing a measure of similarity known in the art, such as but not limited to those disclosed in Section 5.10, also can be used to compute the correlation. In specific embodiments, the number of pairs of replicate biological samples is at least 5, at least 10, at least 20, at least 30, at least 50, at least 80, or at least 100 pairs of replicate biological samples. Furthermore, the number of pairs of replicate biological samples is at the discretion of the investigator. In some embodiments, the cardinality c(R) of the replicates (i.e., the number of pairs of replicate biological samples) is comparable to the cardinality c(M) of matched pairs in the population of matched pairs (i.e., the number of matched pairs of the first type of biological sample and the analogous second type of biological sample). For example, in specific embodiments, the cardinality c(R) of the replicates is equal to the cardinality c(M) of matched pairs in the population of matched pairs. In some embodiments, the cardinality c(R) of the replicates is more than or less than the cardinality c(M) of matched pairs in the population of matched pairs.

In some embodiments, the predetermined threshold is a central tendency of a distribution of values of the measures of similarity computed over the abundance levels of transcripts of the genes in nucleic acid preparations derived from the pairs of replicate biological samples. In the foregoing embodiments, the central tendency can be, for example, a geometric mean, an arithmetic mean, median, or mode of the distribution of values of the measures of similarity computed over the abundance levels of transcripts of the genes in nucleic acid preparations derived from the pairs of replicate biological samples. Preferably, the central tendency is a median. For example, the distribution of values of the measure of similarity (such as but not limited to a correlation coefficient) computed for abundance levels of the transcripts of the genes in the matched pairs may be compared to a distribution of measures of similarity (such as correlation coefficients) computed for the abundance levels of transcripts of the genes in pairs of replicate biological samples. The pro-determined threshold is determined based on the values of the measure of similarity for the abundance levels of transcripts of the genes in the replicate biological samples. In some embodiments, the predetermined threshold is the geometric mean, an arithmetic mean, median or mode of the distribution of values of the measure of similarity of the abundance levels of transcripts of the genes in the replicate biological samples. In some embodiments, the highly-correlated genes are those genes whose transcripts have abundance levels with a value of correlation above the median value of the distribution of the measure of similarity of the abundance levels of transcripts of the genes in the replicate biological samples. In the foregoing embodiments, the values of the measure of similarity of the abundance levels of transcripts of the genes in the replicate biological samples may be used as a baseline for setting the pre-determined threshold for the genes.

In some embodiments, the predetermined threshold is higher or lower, by a certain percentage, than the central tendency of the distribution of values of the measures of similarity computed over the abundance levels of transcripts of the genes in nucleic acid preparations derived from the pairs of replicate biological samples. The central tendency can be, for example, a geometric mean, an arithmetic mean, median, or mode of a distribution of values of these measures of similarity. Preferably, the central tendency is a median. In specific embodiments, the predetermined threshold is a selected value higher than the value of the central tendency by at least 5%, at least 10%, at least 15%, at least 20%, at least 30%, at least 35%, or more, of the value of the central tendency. For example, if the central tendency is a median of correlation coefficient of value 0.5, then the predetermined threshold can be selected as 0.55 (10% higher), 0.57 (~15% higher), 0.6 (20% higher), 0.65 (30% higher), 0.67 (~35% higher), or more. In specific embodiments, the predetermined threshold is a selected value lower than the value of the central tendency by at least 5%, at least 10%, at least 15%, at least 20%, at least 30%, at least 35%, or more, of the value of the central tendency. For example, if the central tendency is a median of correlation coefficient of value 0.5, then the predetermined threshold can be selected as 0.45 (10% lower), 0.42 (~15% lower), 0.4 (20% lower), 0.35 (30% lower), 0.32 (~35% lower), or less. Preferably, the predetermined threshold is higher than the value of central tendency. In the foregoing embodiments, different sets of highly-correlated genes can be identified using the different values of the predetermined threshold.

In a specific embodiment where the measure of similarity is the standard Pearson correlation coefficient, by way of example, the abundance values derived from the first type of biological sample and the second type of biological sample of the matched pairs can be considered to be highly-correlated when the P value for such measurements is 0.05 or less, 0.005 or less, or 0.0005 or less. In some embodiments, the abundance values derived from the first type of biological sample and the second type of biological sample of the matched pairs are considered correlated if they share a correlation coefficient that is 0.5, or greater, 0.6, or greater, 0.7, or greater, or 0.8 or greater, where the correlation coefficient scale for the correlation coefficient ranges from −1.0 (perfect anti-correlation) to 1.0 (perfect correlation), where zero indicates no correlation.

In alternative embodiments, the error rate of the predictive performance of a classifier is used to determine the highly-correlated genes. In some embodiments, the highly-correlated genes are identified by ranking genes as to their performance as predictors of phenotypic characterization, and selecting a number of the top performing genes, building a classifier 15' using the selected top performing genes (such as according to the method discussed in Section 5.3), and testing the performance of the classifier using validation biological samples (i.e., samples of known phenotypic characterization). For example, the performance of a classifier may be evaluated by computing an error rate for classification of the validation samples, where the classifiers with the lowest error rate are the optimal classifiers. The genes whose transcript abundance levels produced the optimal classifiers are the highly-correlated genes. Thus, highly-correlated genes may be identified by the performance of a classifier. The validation biological samples may be used if the cardinality c(M) of the matched pairs is insufficient to provide acceptably narrow confidence intervals for the performance of the classifier, thus, the validation biological samples can compensate for any difficulties that may be associated with acquiring matched pairs of biological samples (such as but not limited to matched pairs of frozen and fixed biological samples). In alternative embodiments of the invention, the highly-correlated genes identified by the foregoing methods can be used in any of the methods for training a classifier that classifies a biological sample as to a phenotypic characterization as disclosed in this application.

Step 208.

In step 208, an identification of the "highly-correlated" genes is optionally outputted to a user, a user interface device, a computer readable storage medium, a monitor, a local computer, or a computer that is part of a network, or displayed to a user.

In a specific embodiment, a method is provided for identifying a plurality of protein-coding genes whose abundance levels in nucleic acid preparations are useful for classifying both a first type of biological sample and a second type of biological sample, where the first type of biological sample and the second type of biological sample are a sample type selected from the group consisting of a fresh biological sample, a frozen biological sample, a biological sample that has been preserved with a non-crosslinking preservative, and a fixed biological sample that has been fixed with a crosslinking agent, where the first type of biological sample and the second type of biological sample are sample types that are not the same sample type, said method comprising: identifying a plurality of protein-coding genes, each of which has a respective transcript with an abundance level in a nucleic acid preparation derived from a first of biological sample that is correlated with an abundance level of said respective transcript of said protein-coding gene in a nucleic acid preparation derived from an analogous said second type of biological sample, wherein said abundance levels are deemed to be correlated if a measure of similarity between said abundance levels is above a predetermined threshold, wherein the measure of similarity is a Pearson correlation coefficient, wherein the predetermined threshold is a median (or a specified percentage greater than the median) of a distribution of values of the Pearson correlation coefficient, and wherein the Pearson correlation coefficient is computed for each respective individual gene in a plurality of candidate protein-coding genes, over respective abundance levels of transcripts of said individual candidate protein-coding gene in nucleic acid preparations derived from pairs of replicate biological samples that are of the same tissue type (preferably, the same tissue type of malignancy in an embodiment where the members of each matched pair in the population of matched pairs are the same tissue type of malignancy) and the same species as the biological sample of the matched pairs which generally better preserves nucleic acids.

In a specific embodiment, a method is provided for identifying a plurality of protein-coding genes whose abundance levels in nucleic acid preparations are useful for classifying biological samples that have been frozen and biological samples that have been fixed (such as but not limited to formalin-fixed paraffin-embedded (FFPE) biological samples), said method comprising: (a) for each gene in the expression profiles in a set of expression profiles respectively from matched pairs of a fixed biological sample and analogous frozen biological sample, computing a value of a measure of similarity for each respective individual gene in a plurality of candidate protein-coding genes, over respective abundance levels of transcripts of individual candidate protein-coding genes in nucleic acid preparations derived from the matched pairs and estimating the distribution of the values of the measures of similarity; (b) for each gene in the expression profiles in a set of expression profiles from pairs of replicate frozen biological samples that are of the same tissue type (preferably, the same tissue type of malignancy) and the same species (preferably human) as the analogous frozen biological sample, computing a value of a measure of similarity for each respective individual gene in a plurality of candidate protein-coding genes, over respective abundance levels of transcripts of individual candidate protein-coding genes in nucleic acid preparations derived from the pairs of replicate frozen biological samples and estimating the distribution of the values of the measures of similarity; (c) comparing the distributions computed in steps (a) and (b); and (c) identifying a subset of protein-coding genes whose reproducibility, measured by a mean of the distribution of correlation coefficients for that gene, is similar between the matched pairs of the population of matched pairs and the pairs of replicate frozen biological samples. The number of the matched pairs and the pairs of replicates can be as described above.

5.3 Methods for Training a Classifier for Use with Both First and Second Types of Biological Samples Computer-implemented methods also are provided for training a classifier useful for classifying as to a phenotypic characterization both a first type of biological sample and a second type of biological sample, where the first type of biological sample and the second type of biological sample are sample types that are not the same sample type, using highly-correlated genes identified as described in Section 5.2, above. In one embodiment, the computer-implemented method comprises training a classifier for classifying biological samples as to phenotypic characterizations of interest using abundance levels of respective transcripts of a set of genes in nucleic acid preparations derived from a plurality of training biological samples, the training biological samples being from subjects having the phenotypic characterizations of interest selected from a set of at least two phenotypic characterizations of interest; the set of genes containing at least 111 genes, wherein at least 90% of the genes in the set of genes are highly-correlated protein-coding genes, and wherein the plurality of training biological samples having each phenotypic characterization of interest is at least 5, 10, 20, or 50 biological samples.

Figure 3:
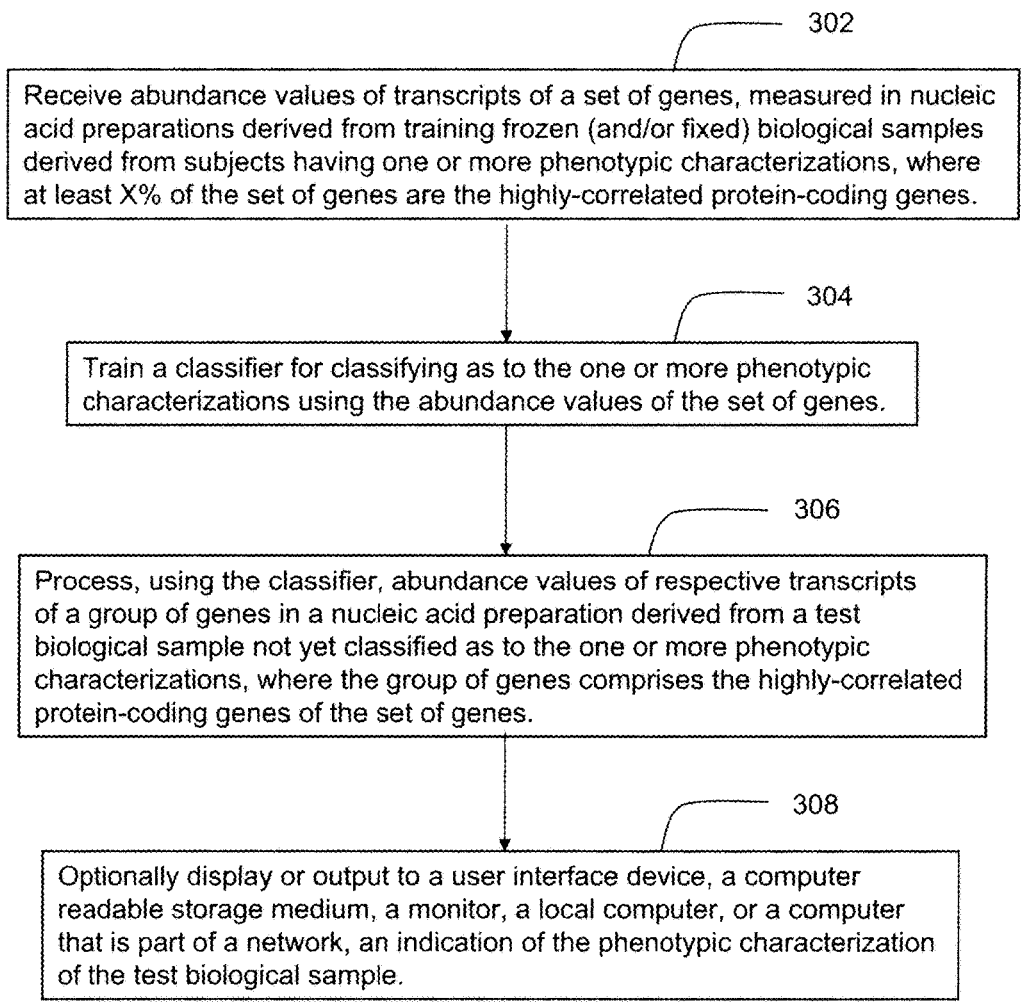
FIG. 3 illustrates an exemplary method for training a classifier for use in determining a phenotypic characterization of a biological sample from among a set of phenotypic characterizations using the highly-correlated genes, and for using the classifier for classifying a biological sample of unknown phenotypic characterization in accordance with an embodiment of the present invention.

Referring to FIG. 3, an exemplary method for use in training a classifier for use in determining a phenotypic characterization of a test biological sample from among a set of phenotypic characterizations using a training population is provided.

Step 302.

In step 302, data from training microarray experiments 46-$i$, i=1, . . . , N, are received (see FIG. 1). The data from training microarray experiments comprise the abundance levels of respective transcripts of a set of genes in nucleic acid preparations derived from a plurality of training biological samples from subjects having the phenotypic characterizations (which are of interest for classifying a test biological sample), which are at least two distinguishable phenotypic characterizations of interest. In some embodiments, the set of genes contains at least 11 genes. In different embodiments, the set of genes contains at least 50 genes, at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes. In the foregoing embodiments, the highly-correlated genes are at least 10%, at least 25%, at least 30, at least 50%, at least 75%, at least 80%, at least 90%, at least 95%, at least 99%, or all of the set of genes. In specific embodiments, at least 90% of the genes in the set of genes are highly-correlated genes. In specific embodiments, the plurality of protein-coding genes is at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes. The highly-correlated genes are protein-coding genes, each of which has a respective transcript with an abundance level in a nucleic acid preparation derived from a first type of biological sample that is correlated with an abundance level of the respective transcript of that protein-coding gene in a nucleic acid preparation derived from an analogous second type of biological sample, wherein the abundance levels are deemed to be correlated if a measure of similarity between the abundance levels is above a predetermined threshold (see Section 5.2, above).

In some embodiments, data from microarray experiments 46-$i$ are received in the form of an electronic file or signal by computer 10 from a remote location over wide area network 34, where the wide area network is an example of computer network. The remote location may be in the same building as computer 10, in another building as computer 10, in the same city as computer 10, in a different city as computer 10. The remote location may be in the same or different state, country or continent as computer 10. In some embodiments, the data from microarray experiments 46-$i$ are encrypted.

In some embodiments, the abundance levels of transcripts in nucleic acid preparations derived from the training biological samples are represented by an expression profile. An expression profile can be represented by the vector p, $$p=[p_1, \ldots, p_i, \ldots, p_n]$$

where $p_i$ is the abundance level of the i'th component, for example, the transcript level of gene i. In specific embodiments, n is more than 2, more than 10, more than 100, more than 200, more than 500, more than 1000, more than 2000, more than 2500, more than 7500, more than 10,000, more than 20,000, more than 25,000, or more than 35,000.

In a specific embodiment, the training biological samples are from humans.

In the foregoing or other embodiments, the training biological samples preferably are: (i) biological samples of the same sample type as the first type of biological sample of the matched pairs that were used to identify the highly-correlated genes, (ii) biological samples of the same sample type as the analogous second type of biological sample of the matched pairs that were used to identify the highly-correlated genes, or (iii) a mixture of (i) and (ii). However, in some embodiments where the first type of biological sample of the matched pairs used to identify the highly-correlated genes is a fixed biological sample that has been fixed with a crosslinking agent, the training biological samples can be of sample type of: a fresh biological sample, a frozen biological sample, or a biological sample that has been preserved with a non-crosslinking preservative. In other embodiments where the first type of biological sample of the matched pairs used to identify the highly-correlated genes is a fixed biological sample that has been fixed with a crosslinking agent, the training biological samples are fixed biological samples that have been fixed with a crosslinking agent.

Step 304.

In step 304, a classifier is trained using abundance levels of respective transcripts of the set of genes in nucleic acid preparations derived from a plurality of training biological samples from subjects having the phenotypic characterizations of interest selected from at least two distinguishable phenotypic characterizations of interest. In some embodiments, classifier training module 64 is used for training the classifier. Examples of classifiers include but are not limited to neural networks, classifiers that employ clustering, and support vector machines (classifiers are discussed in Section 5.11 below).

The classifier receives from Step 302, for each microarray experiment, the abundance levels of respective transcripts of the set of genes in nucleic acid preparations derived from the training biological sample (46-$i$), and the identity of the known phenotypic characterization with which the training biological sample is associated (where the phenotypic characterization is either (a) the presence of a phenotypic characterization of interest, or (b) the presence of a different phenotypic characterization, distinguishable from the phenotypic characterization of interest, or the absence of the phenotypic characterization of interest (48-$i$) (see FIG. 1). The classifier is trained for classifying a biological sample as to each of the one or more known phenotypic characterizations 48-$i$ of the training microarray experiments 46-$i$ using the abundance values of respective transcripts of the set of genes in the training microarray experiments 46-$i$ and the identity of the one or more known phenotypic characterizations (e.g., the presence of a phenotypic characterization of interest, or the presence of a different phenotypic characterization, distinguishable from the phenotypic characterization of interest, or the absence of the phenotypic characterization of interest) associated with each biological sample. In some embodiments, there are at least five training samples in a training population for a phenotypic characterization. In embodiments where data from training microarray experiments 46-$i$ comprise a plurality of microarray experiments from a plurality of training biological samples having different phenotypic characterizations, a classifier is trained for classifying a biological sample as to the phenotypic characterization of the respective training biological sample. In some embodiments, there are at least two, at least three, at least four, at least five, at least seven, at least ten, at least twenty, at least fifty, or at least 100 training samples in a training population for each phenotypic characterization of interest. In a specific embodiment, a first training population has a phenotypic characterization of interest, which phenotypic characterization is the same throughout the first training population, and a second training population has a phenotypic characterization to be distinguished from the phenotypic characterization of interest, wherein each sample in the second training population has the same phenotypic characterization. In some embodiments, the classifier is trained for at least 3, at least 4, at least 5, at least 6, at least 7, at least 8, at least 9, at least 10, at least 20, at least 30, or between 3 and 50 different phenotypic characterizations.

In some embodiments, the classifier is trained using abundance levels of respective transcripts of a set of genes, where the set of genes contains at least 111 genes. In different embodiments, the classifier is trained using abundance levels of respective transcripts of at least 50 genes, at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes. In the foregoing embodiments, the highly-correlated genes can comprise at least 10%, at least 25%, at least 30%, at least 50%, at least 75%, at least 80%, at least 90%, at least 95%, at least 99%, or all of the set of genes whose expression levels can be used for training the classifier. In some embodiments, at least 90% of the genes in the set of genes are highly-correlated genes.

In a preferred embodiment, the abundance levels of all or a subset of the identified highly correlated protein coding genes can be used in training the classifier. In an embodiment where a subset of the highly correlated protein coding genes are used, genes of the subset are selected that have abundance levels that distinguish between two or more training groups: a first training group of subjects with the phenotypic characterization of interest, e.g., a first type of disease or cancer of primary origin, etc.; and a second training group of subjects that is characterized by the phenotype that is to be distinguished from the phenotypic characterization of interest, e.g., a different type of disease or the absence of the disease, or a cancer of different primary origin, etc.; and optionally additional training groups, each with a phenotypic characterization to be distinguished from that of the other training groups. In a specific embodiment, a first training group of subjects may be of patients with non-small cell lung carcinoma, and a second training group of subjects may be of patients with small cell lung carcinoma. As another embodiment, a first training group of subjects may be of patients characterized as having lung cancer, and a second training group of subjects may be of patients characterized as not having lung cancer. As yet another embodiment, a first training group of subjects may be of patients characterized as having a cancer where the origin of the primary cancer is a particular tissue (e.g., breast), and a second training group of subjects may be of patients characterized as having a cancer in which the origin of the primary cancer is a different tissue (e.g., bladder); additional training groups may be of subjects with primary cancers of different tissue origins, e.g., colorectal, gastric, germ cell, kidney, melanoma, ovarian, prostate, hepatocellular, etc., respectively). Methods for selecting genes whose expression levels distinguish between groups are known in the art, and include but are not limited to, Pearson correlation ranking (see e.g., S. Michelson and T. Schofield, 1996, The Biostatistics Cookbook, Kluwer Academic Publishers, Dordrecht, at pp. 122-124), mutual information ranking (described in J. Pierce, 1980, *An Introduction To Information Theory: Symbols, Signals, and Noise*, Dover Publications), SVM-RFE (described in Barnhill, et al., U.S. Pat. No. 7,542,959). In a preferred embodiment, Pearson correlation ranking is used. However, it should be noted that using a subset of the identified highly correlated protein coding genes that are discriminatory (distinguish) between the phenotypic characterizations being distinguished, is optional, because, alternatively, all of the identified highly correlated genes can be used in training the classifier. In a preferred embodiment, different subsets of the highly correlated genes are selected, each of which is evaluated to see which subset has expression levels that classify best relative to a validation group of samples that have the phenotypic characterization of interest and one or more validation groups of samples, each having a phenotypic characterization that is to be distinguished from. The subset that is shown to classify best is used then in classifying biological samples as to that phenotypic characterization.

In some embodiments, the training biological samples contain multiple phenotypic characterizations of interest, for example, different types of cancer, including but not limited to bladder, breast, cholangiocarcinoma/gallbladder, central nervous system, colorectal, endometrial, gastric, germ cell, head and neck squamous cell carcinomas (SCC), malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid. That is, a training biological sample may exhibit not only one phenotypic characterization of interest, but more than one phenotypic characterizations of interest. In addition, training biological samples may be pooled together from biological samples from different subjects each having one or more phenotypic characterizations of interest. In a specific embodiment, the training biological samples can be used to train classifiers at to multiple phenotypic characterizations of interest, where the multiple phenotypic characterizations are different tissues of origin of a cancer of unknown primary.

In some embodiments, the classifier is trained to classify a biological sample as to whether a phenotypic characterization is present or absent, for example, as to the type of cancer. In some embodiments, the classifier is trained to classify a test biological sample as to the identity of an infectious agent infecting the test biological sample or the subject from which the test biological sample is derived. In other embodiments, a classifier can be trained to classify a test biological sample as to whether it is a specific tissue type or not. For example, a classifier can be trained to classify a test biological sample as to whether the tissue of origin of a cancer of unknown primary is of a tissue type A or of a different tissue type B. In another example, a classifier can be trained to classify a training biological sample as to whether it meets a threshold for being classified as being a tissue type A (as the tissue of origin of the cancer of unknown primary).

In some embodiments, a biological sample is classified as to multiple phenotypic characterizations of interest, where each of the multiple phenotypic characterizations belongs to the same phenotypic category. In some embodiments, the phenotypic category is a tissue of origin of a cancer of unknown primary, and the multiple phenotypic characterizations are different tissues of origin of the cancer of unknown primary, including but not limited to bladder, breast, cholangiocarcinoma/gallbladder, central nervous system, colorectal, endometrial, gastric, germ cell, head and neck squamous cell carcinomas (SCC), malignant mesothelioma, and neuroendocrine cancer, kidney, hepatocellular, non-small cell lung, non-Hodgkin's lymphoma, melanoma, ovarian, pancreatic, prostate, soft tissue sarcoma, and thyroid.

In some embodiments, the phenotypic category is the presence of an infectious agent, i.e., the identity of an infectious agent responsible for the presence of an infection. In some embodiments, the infectious agent is a virus. In an embodiment where the infectious agent is a virus, the multiple phenotypic characterizations can be the differing strains of the virus (i.e., the infectious agent) which are infecting the biological sample or the subject from which the test biological sample is derived. For example, in an embodiment where the phenotypic category is the virus that causes influenza, the multiple phenotypic characterizations can be the differing strains of the influenza virus.

In different embodiments, the phenotypic characterization is a tumor type, tissue of origin of a cancer of unknown primary, response to a treatment, aggressiveness or stage of a disease, identity of infectious agent infecting a test biological sample or the subject from which the test biological sample is derived, tissue type, strain of infectious agent infecting a test biological sample or the subject from which it is derived, age of the subject, gender of the subject, etc. In some embodiments, the phenotypic characterization is a tissue of origin of a cancer of unknown primary.

In some embodiments, the performance of candidate classifiers can be tested as a predictor of phenotypic characterization, by building two or more candidate classifiers using different selections of genes, such as using different sets of highly-correlated genes identified using different values of the predetermined threshold (as described in Section 5.3 above) or using different numbers of the top performing highly-correlated genes identified, and testing the performance of the candidate classifiers by applying them to a set of validation biological samples (i.e., samples of known phenotypic characterization) using the method described in Section 5.4, below. The validation biological samples may be additional fixed biological samples (such as FFPE biological samples) which were not among the matched pairs in the population of matched pairs of biological samples used to identify the highly-correlated genes. The performance of the candidate classifier may be evaluated by computing an error rate for classification of the validation biological samples. In some embodiments, the candidate classifier with the lowest error rate is identified as the optimal classifier. In an embodiment where candidate classifiers present similarly low error rates, the candidate classifier with the larger number of genes is selected as the optimal classifier. The cardinality $c(F)$ of the training biological samples (i.e., the number of training biological samples) is preferably much larger than the cardinality $c(V)$ of validation biological samples and the cardinality $c(M)$ of matched pairs in the population of matched pairs (i.e., the number of matched pairs of the first type of biological sample and the analogous second type of biological sample). In an embodiment where the training biological samples are frozen biological samples, this makes it possible, for example, to utilize a large existing body of expression profiles derived from frozen biological samples which may already available. Validation biological samples (V) may be used if the cardinality $c(M)$ of the matched pairs is insufficient to provide acceptably narrow confidence intervals for the performance of the classifier, thus, the validation biological samples can compensate for any difficulties that may be associated with acquiring matched pairs of a first type of biological sample and a second type of biological sample, such as but not limited to frozen and fixed biological samples.

Optionally, one or more parameters of the classifier are outputted to a user, a user interface device, a monitor, a computer readable storage medium, or a local or remote computer system. In some embodiments, the parameters are values of coefficients of the variables which define the classifier. In some embodiment, the output of parameters of the classifier is a plot of values or associations, or a matrix of values. Examples of such parameters include, but are not limited to, values of the weights of the classifier in the output units of a neural network; the values of distance measures or a matrix of values of distance measures or values associated with a distance function or a plot representing the distance measures from clustering; or values, plots or matrices or characterizing the hyper-plane found by a support vector machine.

5.4 Methods for Classifying a Biological Sample as to Phenotypic Characterization Computer-implemented methods also are provided for classifying a test biological sample as to a phenotypic characterization using a classifier trained as described in Section 5.3, above.

In one aspect, the computer-implemented method comprises training a classifier for classifying biological samples as to a phenotypic characterization using abundance levels of respective transcripts of a set of genes in nucleic acid preparations derived from a plurality of training biological samples, the training biological samples being from subjects having the phenotypic characterization; the set of genes containing at least 111 genes, wherein at least 90% of the genes in the set of genes are highly-correlated protein-coding genes, and wherein the plurality of training biological samples is at least 5 biological samples; and processing, using the classifier, abundance levels of respective transcripts of a group of genes in a nucleic acid preparation derived from the test biological sample, wherein the group of genes comprises the protein-coding genes of the set of genes, to classify the test biological sample as to the phenotypic characterization.

In another aspect, the methods comprise processing, using the classifier, abundance levels of respective transcripts of a group of genes in a nucleic acid preparation derived from the test biological sample, to classify the test biological sample as to the phenotypic characterization, wherein the classifier is trained according to a method comprising: training the classifier using abundance levels of respective transcripts of a set of genes in nucleic acid preparations derived from a plurality of training biological samples, the training biological samples being from subjects having the phenotypic characterization; the set of genes containing at least 111 genes, wherein at least 90% of the genes in the set of genes are highly-correlated protein-coding genes, and wherein the plurality of training biological samples is at least 5 biological samples; and wherein the group of genes comprises the highly-correlated protein-coding genes of the set of genes.

In some embodiments, different classifiers are built using sets of genes comprising differing numbers of highly-correlated protein-coding genes. For examples, different classifiers can be built using different sets of highly-correlated genes which are identified using differing values of the predetermined threshold (as described in Section 5.2 above). In another example, different classifiers can be built using different numbers of the top performing highly-correlated genes, such as using at least the top performing 10%, at least the top performing 25%, at least the top performing 30%, at least the top performing 50%, at least the top performing 75% of the highly-correlated genes, or more.

Referring to FIG. 3, an exemplary method for use in classifying a biological sample as to a phenotypic characterization using a classifier is provided.

Step 306.

In step 306, a trained classifier is applied to the abundance levels of respective transcripts of a group of genes in a nucleic acid preparation derived from a test biological sample, where the group of genes comprises the highly-correlated genes of the set of genes (used for training the classifier). The test biological sample is of unknown phenotypic characterization with respect to the phenotypic characterization for which it is being classified. The test biological sample can be a fresh biological sample, a frozen biological sample, a biological sample that has been preserved with a non-crosslinking preservative, or a fixed biological sample that has been fixed with a crosslinking agent, depending on the sample types of the matched pairs which were used to identify the highly-correlated genes. That is, the test biological sample can be: (i) the same sample type as the first type of biological sample of the matched pairs that were used to identify the highly-correlated genes, or (ii) the same sample type as the analogous second type of biological sample of the matched pairs that were used to identify the highly-correlated genes. For example, the test biological sample can be a frozen biological sample, a fixed biological sample, or a mixture of frozen and fixed biological samples if the matched pairs that were used to identify the highly-correlated genes were fixed biological samples and analogous frozen biological samples. In a preferred embodiment, the test biological sample which is fixed biological sample is a FFPE biological sample. In another example, the test biological sample can be a biological sample that has been preserved with a non-crosslinking preservative or a fixed biological sample, if the matched pairs that were used to identify the highly-correlated genes were fixed biological samples and analogous biological samples that have been preserved with a non-crosslinking preservative. The result of the processing of Step 306 is that the unclassified biological sample is classified as to phenotypic characterization, thereby providing a classified biological sample.

In step 306, data from a test microarray experiment 68 is received. In some embodiments, the test microarray experiment 68 comprises a set of abundance values for a plurality of abundance values of transcripts in nucleic acid preparations derived from biological samples for a group of genes measured from a test biological sample. The group of genes comprises the highly-correlated genes of the set of genes used to train the classifier. In some embodiments, data from test microarray experiment 68 comprises a plurality of microarray experiments from a plurality of test biological samples, where each microarray experiment comprises abundance values of transcripts in nucleic acid preparations derived from a test biological sample. The data from test microarray experiment 68 may comprise abundance values from a first type of biological sample or from a second type of biological sample. The highly-correlated genes may be identified using the methods discussed in Section 5.2 above, for example, as in Steps 202-206. In some embodiments, the data from test microarray experiment 68 is received in the form of an electronic file or signal by computer 10 from a remote location over wide area network 34, where the wide area network is an example of computer network. The remote location may be in the same building as computer 10, in another building as computer 10, in the same city as computer 10, in a different city as computer 10. The remote location may be in the same or different state, country or continent as computer 10. In some embodiments the data from test microarray experiment 68 is encrypted.

In the foregoing or other embodiments, the training biological samples preferably are: (i) biological samples of the same sample type as the first type of biological sample of the matched pairs that were used to identify the highly-correlated genes, (ii) biological samples of the same sample type as the analogous second type of biological sample of the matched pairs that were used to identify the highly-correlated genes, or (iii) a mixture of (i) and (ii). Also, in the foregoing or other embodiments, the classifier is trained to classify, as to a phenotypic characterization, preferably: (i) a test biological sample of the same sample type as the first type of biological sample of the matched pairs that were used to identify the highly-correlated genes, or (ii) a test biological sample of the same sample type as the analogous second type of biological sample of the matched pairs that were used to identify the highly-correlated genes. However, in embodiments where the first type of biological sample of each of the matched pairs used to identify the highly-correlated genes is a fixed biological sample that has been fixed with a crosslinking agent, a classifier trained using abundance levels from training biological samples of a sample type selected from the group consisting of: a fresh biological sample, a frozen biological sample, and a biological sample that has been preserved with a non-crosslinking preservative, can be used to classify a test biological sample which is a fresh biological sample, a frozen biological sample, a biological sample that has been preserved with a non-crosslinking preservative, or a fixed biological sample that has been fixed with the same crosslinking agent. In other embodiments where the first type of biological sample of each of the matched pairs used to identify the highly-correlated genes is a fixed biological sample that has been fixed with a crosslinking agent, a classifier trained using abundance levels from training biological samples which are fixed biological samples that have been fixed with a crosslinking agent, can be used to classify a test biological sample which is a fresh biological sample, a frozen biological sample, a biological sample that has been preserved with a non-crosslinking preservative, or a fixed biological sample that has been fixed with the same crosslinking agent.

In preferred embodiments, the abundance levels of transcripts in nucleic acid preparations derived from the test biological samples are represented by an expression profile. An expression profile can be represented by the vector p, $$p=[p_1, \ldots p_i, \ldots p_n]$$

where $p_i$ is the abundance level of the i'th component, for example, the transcript level of gene i. In specific embodiments, n is more than 2, more than 10, more than 100, more than 200, more than 500, more than 1000, more than 2000, more than 2500, more than 7500, more than 10,000, more than 20,000, more than 25,000, or more than 35,000.

In preferred embodiments, the test biological sample is from a human.

In preferred embodiments, the classifier provides the probability that a particular phenotypic characterization is present, preferably expressed as a numeric value. Preferably the classifier provides probabilities for multiple phenotypic characterizations, preferably all belonging to a single category (for example, where the multiple phenotypic characterizations are different tissues of origin of a cancer of unknown primary). Preferably, where the multiple phenotypic characterizations are different tissues of origin of a cancer of unknown primary, the classifier provides a probability for each tumor type, where the numerical values of probabilities for the tumor types collectively sum to 100 (for example, if expressed as a percentage).

In some embodiments, the test biological sample is classified as to whether a phenotypic characterization is present or absent, for example, as to whether a subject has a type of cancer, or a type of viral infection. In other embodiments, a test biological sample is classified as to whether a specific tissue type is present or absent. For example, a test biological sample can be classified as to whether the tissue of origin of a cancer of unknown primary is of a tissue type A or of a different tissue type B (or any number of other tissue types). In another example, a test biological sample can be classified as to whether it meets a threshold for being classified as being a tissue type A (as the tissue of origin of the cancer of unknown primary).

In some embodiment, a biological sample is classified as to multiple phenotypic characterizations (for example, by providing the respective probability that each phenotypic characterization of the multiple phenotypic characterizations is present), a biological sample is classified as to multiple phenotypic characterizations, where each of the multiple phenotypic characterizations belongs to the same phenotypic category. An example of a phenotypic category is a tissue of origin of a cancer, and the multiple phenotypic characterizations is the tissue type including but not limited to liver, brain, heart, skeletal muscle, white adipose, blood, lung, kidney, bone marrow, breast, kidney, blood, bone marrow, cartilage, colon, embryo, gut, hair root, muscle, oocytes, pancreas, placenta, retina, skin, testicles, thyroid, ovary, bladder, and prostate.

In some embodiments, the phenotypic category is a tissue of origin of a cancer of unknown primary, and the multiple phenotypic characterizations are different tissues of origin of the cancer of unknown primary, including but not limited to bladder, breast, cholangiocarcinoma/gallbladder, central nervous system, colorectal, endometrial, gastric, germ cell, head and neck squamous cell carcinomas (SCC), malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid. Preferably, the classifier provides respective probabilities of more than 1, more than 2, more than 3, more than 5, more than 8, more than 10, more than 15, or more than 20 different tissues of origin of a cancer of unknown primary.

In some embodiments, the phenotypic category is the type of an infectious agent present, i.e., the identity of an infectious agent responsible for the presence of an infection. In an embodiment where the infectious agent is a virus, the multiple phenotypic characterizations can be different types of virus (for example, influenza virus, herpes virus, human immunodeficiency virus, etc.) or the strains of infectious agent which are infecting a biological sample (such as the differing strains of the virus) or the subject from which the biological sample is derived. For example, the phenotypic category may be the virus that causes influenza, the multiple phenotypic characterizations can be the differing strains of the influenza virus.

Step 308.

An indication of the phenotypic characterization of the classified biological sample is optionally outputted to a user, a user interface device, a monitor, a computer readable storage medium, or a local or remote computer system.

In the different embodiments discussed in this application, a remote computer can be any computer other than the computer that runs one or more steps of any of the methods described in this application. In some embodiments, a local computer is a computer that runs one or more steps of any of the methods described in this application. A remote computer can be in electronic communication with a local computer by any wired or wireless means known in the art including, but not limited to, 802.11 compliant wireless signals, the Internet, Ethernet, wide area network, and the like. In some embodiments, a remote source (for example, a source of the data from the microarray experiments) is a remote computer. In some embodiments, a remote source is remote electronic storage media that is electronically accessible by a computer network or other electronic means.

5.5 Biological Samples

A biological sample can be any clinically relevant tissue sample, such as a tumor biopsy or fine needle aspirate. A biological sample can be derived, for example, from cell or tissue cultures ex vivo. Alternatively, a biological sample can be derived from a living organism or from a population of single cell organisms. The sample may be taken from any living organism, non-limiting examples of which are a human or a non-human animal (in a veterinary context) such as ruminants, horses, swine or sheep, or domestic companion animals such as felines and canines. Biological samples include tissue samples (such as tissue sections and needle biopsies of tissue), cell samples (for example, cytological smears such as Pap or blood smears or samples of cells obtained by microdissection), samples of whole organisms (such as samples of yeast or bacteria), or cell fractions, fragments or organelles (such as obtained by lysing cells and separating their components by centrifugation or otherwise), as long as nucleic acid preparations can be derived therefrom that can be used to measure abundance levels of transcripts of protein-coding genes. Other examples of biological samples may include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing nucleic acids or cells.

5.6 Treatment of Biological Samples

As is well known in the art, a biological sample may be subjected to a preservation process with the aim of preserving the biological sample for later study or analysis. Preserved samples may be stored for later use. Such preservation methods include but are not limited to preservation with a non-crosslinking preservative, fixation with a crosslinking agent (such as but not limited to formalin-fixation or formalin-fixation with paraffin-embedding), and flash freezing.

Nucleic acid preparations can be extracted from fresh biological samples, frozen biological samples, biological samples that have been preserved with a non-crosslinking preservative, or fixed biological samples that have been fixed with a crosslinking agent, using any method known in the art. The abundance levels of transcripts of the genes of interest are measured in nucleic acid preparations derived from the preserved biological samples. A preserved biological sample may be subjected to one or more treatments in preparation for nucleic acid extraction. Any treatment in the art for preparing preserved biological samples in preparation for nucleic acid extraction is applicable.

For example, frozen biological samples can be thawed, incubated (for example, to reduce condensation), deproteinated, rinsed and dehydrated in preparation for nucleic acid extraction.

FFPE biological samples or other paraffin-embedded biological samples can be sectioned, deparaffinized, deproteinated, rinsed and dehydrated in preparation for nucleic acid extraction. See, e.g., U.S. Pat. No. 6,610,488. Solvents and/or solutions which may be used for de-paraffinization of paraffin-embedded biological samples include limonene, aqueous detergent solutions, and hydrocarbons (for example, alkanes, isoalkanes and aromatic compounds such as xylene).

Solvents which can be used to dehydrate or re-hydrate biological samples include ethanol, water, and mixtures thereof.

5.7 Phenotypic Characterizations

The phenotypic characterization of training biological samples used to train a classifier, or as to which a test biological sample can be classified, may be a tumor type, the tissue of origin of a disease (such as of a cancer of unknown primary), the response to a treatment, the aggressiveness or stage of a disease, identity of an infectious agent infecting a biological sample or the subject from which the biological sample is derived, the tissue type, strain of infectious agent infecting a biological sample or the subject from which it is derived, the age of a subject, the gender of a subject, etc. In some embodiments, the phenotypic characterization is a tissue of origin of a cancer of unknown primary.

In a specific embodiment, a biological sample is classified as to multiple phenotypic characterizations, where each of the multiple phenotypic characterizations belong to the same phenotypic category. An example of a phenotypic category is a tissue of origin of a cancer of known primary, where the multiple phenotypic characterizations are different tissues of the cancer of unknown primary, including but not limited to bladder, breast, cholangiocarcinoma/gallbladder, central nervous system, colorectal, endometrial, gastric, germ cell, head and neck squamous cell carcinomas (SCC), malignant mesothelioma, and neuroendocrine cancer, kidney, hepatocellular, non-small cell lung, non-Hodgkin's lymphoma, melanoma, ovarian, pancreatic, prostate, soft tissue sarcoma, and thyroid.

In specific embodiments, the phenotypic category is a type of tissue, and the multiple phenotypic characterizations include but are not limited to liver, brain, heart, skeletal muscle, white adipose, blood, lung, kidney, bone marrow, breast, kidney, blood, bone marrow, cartilage, colon, embryo, gut, hair root, muscle, oocytes, pancreas, placenta, retina, skin, testicles, thyroid, ovary, bladder, and prostate.

In specific embodiments, the phenotypic category is the type of an infectious agent present, i.e., the identity of an infectious agent responsible for the presence of an infection. In an embodiment where the infectious agent is a virus, the multiple phenotypic characterizations can be different types of virus (for example, influenza virus, herpes virus, human immunodeficiency virus, etc.) or the strain of infectious agent which are infecting a biological sample (such as the differing strains of the virus) or the subject from which the biological sample is derived. For example, the phenotypic category may be influenza, the multiple phenotypic characterizations can be the differing strains of the influenza virus. In yet another embodiment, the phenotypic category is an avian influenza virus, and the multiple phenotypic characterizations are the differing strains of the avian influenza virus or the subject from which the biological sample is derived.

In specific embodiments of the present invention, the phenotypic characterization is a disease state, such as but not limited to presence (or absence), aggressiveness, or stage of disease in a biological sample and or a subject from which the biological sample was obtained. Exemplary diseases include, but are not limited to, asthma, ataxia telangiectasia (Jaspers and Bootsma, 1982, *Proc. Natl. Acad. Sci. U.S.A.* 79: 2641), bipolar disorder, a cancer, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, *Hepatology* 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80), AIDS, rheumatoid arthritis, coronary artery disease, and multiple sclerosis.

Phenotypic characterizations that are cancers include, but are not limited to, sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, and heavy chain disease. Other cancers include, but are not limited to, colorectal, non-small cell lung, gastric, kidney, hepatocellular, non-Hodgkin's lymphoma, prostate, soft tissue sarcoma, thyroid, germ cell, cholangiocarcinoma/gallbladder, central nervous system, colorectal, endometrial, head and neck squamous cell carcinomas (SCC), malignant mesothelioma, and neuroendocrine cancer.

In some embodiments, a phenotypic characterization is a cell type. Exemplary cell types include, but are not limited to, wet stratified barrier epithelial cells such as surface epithelial cells of stratified squamous epithelium of cornea, tongue, oral cavity, esophagus, anal canal, distal urethra and vagina, basal cells (stem cell) of epithelia of cornea, tongue, oral cavity, esophagus, anal canal, distal urethra and vagina, and urinary epithelium cells (lining urinary bladder and urinary ducts).

Exemplary cell types further include, but are not limited to, metabolism and storage cells such as hepatocytes (liver cells), white fat cells, brown fat cells, and liver lipocytes. Exemplary cell types further include, but are not limited to, barrier function cells (lung, gut, exocrine glands and urogenital tract) such as type I pneumocytes (lining air space of lung), pancreatic duct cells (centroacinar cell), nonstriated duct cells (of sweat gland, salivary gland, mammary gland, etc.), kidney glomerulus parietal cells, kidney glomerulus podocytes, loop of Henle thin segment cells (in kidney), kidney collecting duct cells, and duct cells (of seminal vesicle, prostate gland, etc.).

Exemplary cell types further include, but are not limited to, blood and immune system cells such as erythrocytes (red blood cell), megakaryocytes (platelet precursor), monocytes, connective tissue macrophages (various types), epidermal Langerhans cells, osteoclasts (in bone), dendritic cells (in lymphoid tissues), microglial cells (in central nervous system), neutrophil granulocytes, eosinophil granulocytes, basophil granulocytes, mast cells, helper T cells, suppressor T cells, cytotoxic T cells, B cells, natural killer cells, and reticulocytes.

Exemplary cell types further include, but are not limited to, autonomic neuron cells such as cholinergic neural cells, adrenergic neural cells, and peptidergic neural cells. Exemplary cell types further include, but are not limited to, sense organ and peripheral neuron supporting cells such as inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, type I taste bud supporting cells, olfactory epithelium supporting cells, Schwann cells, satellite cells (encapsulating peripheral nerve cell bodies), and enteric glial cells.

Exemplary cell types further include, but are not limited to, central nervous system neurons and glial cells such as astrocytes, neuron cells, oligodendrocytes, and spindle neurons. Exemplary cell types further include, but are not limited to, lens cells such as anterior lens epithelial cells, crystallin-containing lens fiber cells, and karan cells. Exemplary cell types further include, but are not limited to, pigment cells such as melanocytes and retinal pigmented epithelial cells. Exemplary cell types further include, but are not limited to, germ cells such as oogoniums/oocytes, spermatids, spermatocytes, spermatogonium cells, (stem cell for spermatocyte), and spermatozoon. Exemplary cell types further include, but are not limited to, nurse cells such as ovarian follicle cells, sertoli cells (in testis), and thymus epithelial cells. For more reference on cell types see Freitas Jr., 1999, *Nanomedicine,* Volume I: Basic Capabilities, Landes Bioscience, Georgetown, Tex.

5.8 Measurements of the Abundance Levels of Transcripts

This section provides exemplary methods for measuring the abundance levels of transcripts in nucleic acid preparations derived from biological samples. One of skill in the art will appreciate that this invention is not limited to the following specific measurement methods.

5.8.1 Transcript Assay Using Microarrays

The techniques described in this section are particularly useful for the determination of the abundance levels of transcripts in a cell or cell type or any other biological sample. These techniques include the provision of polynucleotide probe arrays that can be used to provide simultaneous determination of the expression levels of a plurality of genes.

The expression level of a nucleotide sequence of a gene can be measured by any high throughput technique. However measured, the result is either the absolute or relative amounts of transcripts including, but not limited to, values representing abundances or abundance ratios. Preferably, measurement of the expression profile is made by hybridization to transcript arrays, which are described in this subsection. In one embodiment, "transcript arrays" are used. Transcript arrays can be employed for analyzing the expression profile in a cell sample and especially for measuring the expression profile of a cell sample of a particular tissue type or developmental state or afflicted with a disease or disorder or exposed to a drug of interest.

In one embodiment, an expression profile that is obtained by hybridizing detectably labeled polynucleotides representing the nucleotide sequences in mRNA transcripts present in a cell (for example, fluorescently labeled cDNA synthesized from total cell mRNA) to a microarray. In some embodiments, a microarray is an array of positionally-addressable binding (for example, hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described hereinbelow. However produced, microarrays share certain characteristics. The arrays are reproducible, allowing multiple copies of a given array to be produced and easily compared with each other.

Preferably, a given binding site or unique set of binding sites in the microarray will specifically bind (for example, hybridize) to a nucleotide sequence in a single gene from a cell or organism (for example, to exon of a specific mRNA or a specific cDNA derived therefrom). The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (for example, the sequence) of each probe can be determined from its position on the array (for example, on the support or surface). In some embodiments, the arrays are ordered arrays.

Preferably, the density of probes on a microarray or a set of microarrays is 100 different (for example, non-identical) probes per 1 cm$^2$ or higher. In some embodiments, a microarray can have at least 550 probes per 1 cm$^2$, at least 1,000 probes per 1 cm$^2$, at least 1,500 probes per 1 cm$^2$ or at least 2,000 probes per 1 cm$^2$. In some embodiments, the microarray is a high density array, preferably having a density of at least 2,500 different probes per 1 cm$^2$. A microarray can contain at least 2,500, at least 5,000, at least 10,000, at least 15,000, at least 20,000, at least 25,000, at least 50,000 or at least 55,000 different (for example, non-identical) probes.

In one embodiment, the microarray is an array (for example, a matrix) in which each position represents a discrete binding site for a nucleotide sequence of a transcript encoded by a gene (for example, for an exon of an mRNA or a cDNA derived therefrom). In such and embodiment, the collection of binding sites on a microarray contains sets of binding sites for a plurality of genes. For example, in various embodiments, a microarray can comprise binding sites for products encoded by fewer than 50% of the genes in the genome of an organism. Alternatively, a microarray can have binding sites for the products encoded by at least 50%, at least 75%, at least 85%, at least 90%, at least 95%, at least 99% or 100% of the genes, or at least X genes, where X=2500, 5000, 10000, 15000, 20000, 25000, 30000, 40000, or 55000 genes, in the genome of an organism (for example, human, mammal, rat, mouse, pig, dog, cat, etc.). In other embodiments, a microarray can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, for example, a synthetic oligomer or a gene fragment, for example corresponding to an exon.

In some embodiments, a gene is represented in profiling arrays, a type of microarray, by a set of binding sites comprising probes with different polynucleotides that are complementary to different sequence segments of the gene. Such polynucleotides are preferably of the length of 15 to 200 bases, more preferably of the length of 20 to 100 bases, most preferably 40-60 bases. In some embodiments, the profiling arrays comprise one probe specific to each target gene. However, if desired, the profiling arrays can contain at least 2, 5, 10, 100, or 1000 or more probes specific to some target genes.

5.8.1.1 Preparing Probes for Microarrays

As noted above, the "probe" to which a RNA transcript, or nucleic acid derived therefrom, specifically hybridizes is a complementary polynucleotide sequence.

In some embodiments, the probes may comprise DNA or DNA "mimics" (for example, derivatives and analogues). In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, for example, phosphorothioates. DNA can be obtained, for example, by polymerase chain reaction (PCR) amplification of segments containing exons from genomic DNA, cDNA (for example, by RT-PCR), or cloned sequences. Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, for example, using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between 10 and 600 bases in length, more typically between 20 and 100 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, for example, Egholm et al., 1993, *Nature* 363:566-568; and U.S. Pat. No. 5,539,083).

In alternative embodiments, the hybridization sites (for example, the probes) are made from plasmid or phage clones of genes, cDNAs (for example, expressed sequence tags), or inserts therefrom (Nguyen et al., 1995, *Genomics* 29:207-209).

In specific embodiments, biological samples are processed using the NuGEN WT-Ovation® system (NuGEN Technologies, Inc., San Carlos, Calif.) for FFPE biological samples for cDNA synthesis and the FL-Ovation™ cDNA Biotin Module for labeling. In some embodiments, biological samples are analyzed using the Genisphere RampUP™ 2-cycle kit (Genisphere Inc., Hatfield, Pa.). Generally, in NuGEN and Genisphere assays, labeled (biotinylated) cDNA is produced. In other assays, biotinylated cRNA may be produced.

In specific embodiments, biological samples, such as but not limited to frozen biological samples, are processed using a commercially available kit, which can be but is not limited to Genisphere SenseAMP™ (Genisphere Inc., Hatfield, Pa.), Affymetrix GeneChip® reagents (Affymetrix Inc., Santa Clara, Calif.), BioArray® HighYield® RNA Transcript Labeling Kit (Enzo Biochem, Inc., New York, N.Y.), or MagMAX™-96 for Microarrays Total RNA Isolation Kit (Ambion, Inc., Austin, Tex.).

5.8.1.2 Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, for example, from glass, plastic (for example, polypropylene, nylon), polyacrylamide, nitrocellulose, gel, or other porous or nonporous material.

One method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al, 1996, *Genome Res.* 6:639-645; and Schena et al., 1995, *Proc. Natl. Acad Sci. U.S.A.* 93:10539-11286).

A second method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (for example, 60-mers) of known sequence are synthesized directly on a surface such as a derivatized glass slide. The array produced can be redundant, with several polynucleotide molecules per gene.

Other methods for making microarrays, for example, by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., 2001, *Molecular Cloning*, 3rd edition, Cold Spring Harbor Laboratory Press) could be used.

In one embodiment, microarrays are manufactured by means of an ink jet printing device for oligonucleotide synthesis, for example, using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays can be synthesized in arrays, for example, on a glass slide, by serially depositing individual nucleotide bases in "microdroplets" of a high surface tension solvent such as propylene carbonate. The microdroplets have small volumes (for example, 100 pL or less, more preferably 50 pL or less) and are separated from each other on the microarray (for example, by hydrophobic domains) to form circular surface tension wells which define the locations of the array elements (i.e., the different probes). Polynucleotide probes are normally attached to the surface covalently at the 3N end of the polynucleotide. Alternatively, polynucleotide probes can be attached to the surface covalently at the 5N end of the polynucleotide (see for example, Blanchard, 1998, in *Synthetic DNA Arrays in Genetic Engineering*, Vol. 20, J. K. Setlow, Ed., Plenum Press, New York at pages 111-123).

5.8.1.3 Target Polynucleotide Molecules

Target polynucleotides that can be analyzed include, but by no means are limited to, messenger RNA (mRNA) molecules, cDNAs of mRNA molecules, cRNA molecules (i.e., RNA molecules prepared from cDNA molecules that are transcribed in vivo) and fragments thereof. Target polynucleotides that can also be analyzed by the methods of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules can be naturally occurring nucleic acid molecules such as mRNA molecules, isolated from biological sample. Alternatively, the polynucleotide molecules can be synthesized, including, for example, nucleic acid molecules synthesized enzymatically in vivo or in vitro, such as cDNA molecules, or polynucleotide molecules synthesized by PCR, RNA molecules synthesized by in vitro transcription off of cDNA, etc. In some embodiments, the target polynucleotides will correspond to particular gene transcripts (for example, to particular mRNA sequences expressed in cells or to particular cDNA sequences derived from such mRNA sequences). However, in specific embodiments, the target polynucleotides can correspond to particular fragments (for example, an exon) of a gene transcript.

In some embodiments, the target polynucleotides to be analyzed are prepared in vitro from nucleic acids extracted from cells. For example, in one embodiment, RNA is extracted from cells (for example, total cellular RNA, poly (A)$^+$ messenger RNA, fraction thereof) and messenger RNA is purified from the total extracted RNA. Methods for preparing total and poly(A)$^+$ RNA are well known in the art, and are described generally, for example, in Sambrook et al., supra. In one embodiment, RNA is extracted from cells of the various types of interest using guanidinium thiocyanate lysis followed by CsCl centrifugation and an oligo dT purification (Chirgwin et al., 1979, *Biochemistry* 18:5294-

5299). In another embodiment, RNA is extracted from cells using guanidinium thiocyanate lysis followed by purification on RNeasy columns (Qiagen). cDNA is then synthesized from the purified mRNA using, for example, oligo-dT or random primers. In some embodiments, the target polynucleotides are cRNA prepared from purified messenger RNA extracted from cells. As used in this application, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, for example, U.S. Pat. Nos. 5,891, 636, 5,716,785; 5,545,522 and 6,132,997; see also, U.S. Pat. Nos. 6,271,002, and 7,229,765. Both oligo-dT primers (U.S. Pat. Nos. 5,545,522 and 6,132,997) and random primers (U.S. Pat. No. 7,229,765) that contain an RNA polymerase promoter or complement thereof can be used. The target polynucleotides can be short and/or fragmented polynucleotide molecules that are representative of the original nucleic acid population of the cell.

The target polynucleotides to be analyzed are typically detectably labeled. For example, cDNA can be labeled directly, for example, with nucleotide analogs, or indirectly, for example, by making a second, labeled cDNA strand using the first strand as a template. Alternatively, the double-stranded cDNA can be transcribed into cRNA and labeled.

In some instances, the detectable label is a fluorescent label, for example, by incorporation of nucleotide analogs. Other labels suitable for use include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Some radioactive isotopes include, but are not limited to, $^{32}P$, $^{35}S$, $^{14}C$, $^{15}N$ and $^{125}I$. Fluorescent molecules include, but are not limited to, fluorescein and its derivatives, rhodamine and its derivatives, texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41. Fluorescent molecules further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable, but are not limited to, ferritin, hemocyanin, and colloidal gold. Alternatively, in some embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.8.1.4 Hybridization to Microarrays

As described supra, nucleic acid hybridization and wash conditions are chosen so that the polynucleotide molecules to be analyzed (referred to in this application as the "target polynucleotide molecules) specifically bind or specifically hybridize to the complementary polynucleotide sequences of the array, preferably to a specific array site, where its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (for example, synthetic oligodeoxyribonucleic acids) may need to be denatured prior to contacting with the target polynucleotide molecules, for example, to remove hairpins or dimers which form due to self complementary sequences.

Optimal hybridization conditions will depend on the length (for example, oligomer versus polynucleotide greater than 200 bases) and type (for example, RNA, or DNA) of probe and target nucleic acids. General parameters for specific (for example, stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad Si. U.S.A.* 93:10614). Useful hybridization conditions are also provided in for example, Tijessen, 1993, *Hybridization with Nucleic Acid Probes*, Elsevier Science Publishers B.V. and Kricka, 1992, Nonisotopic DNA Probe Techniques, Academic Press, San Diego, Calif.

Exemplary hybridization conditions for use with the screening and/or signaling chips include hybridization at a temperature at or near the mean melting temperature of the probes (for example, within 5° C., more preferably within 2° C.) in 1 M NaCl, 50 mM MES buffer (pH 6.5), 0.5% sodium Sarcosine and 30% formamide.

5.8.1.5 Signal Detection and Data Analysis

It will be appreciated that when target sequences, for example, cDNA or cRNA, complementary to the RNA of a cell or a nucleic acid preparation derived from a biological sample is made and hybridized to a microarray under suitable hybridization conditions, the level of hybridization to the site in the array corresponding to a transcript of any particular gene will reflect the prevalence in the cell of mRNA or mRNAs transcribed from that gene.

When fluorescently labeled probes are used, the fluorescence emissions at each site of a transcript array can be, preferably, detected by scanning confocal laser microscopy. In one embodiment, a separate scan, using the appropriate excitation line, is carried out for each of two fluorophores used in such embodiments. Alternatively, a laser can be used that allows simultaneous sample illumination at wavelengths specific to the two fluorophores and emissions from the two fluorophores can be analyzed simultaneously (see Shalon et al., 1996, *Genome Res.* 6:639-645). In some embodiments, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, for example, in Schena et al., 1996, *Genome Res.* 6:639-645. Alternatively, the fiber-optic bundle described by Ferguson et al., 1996, *Nature Biotech.*

14:1681-1684, can be used to monitor mRNA abundance levels at a large number of sites simultaneously.

Signals are recorded and, in a preferred embodiment, analyzed by computer. In one embodiment, the scanned image is despeckled using a graphics program (for example, Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

5.9 Preprocessing Routines

Optionally, a number of different preprocessing routines can be performed by preprocessing module 60 to prepare training microarray experiments 46 and/or test microarray experiment 68 for use in the methods discussed above in conjunction with FIGS. 2 and 3. Some such preprocessing protocols are described in this section.

5.9.1 Normalization Techniques

Typically, the preprocessing comprises normalizing the abundance measurement of transcripts in nucleic acid preparations derived from a biological sample. Many of the preprocessing protocols described in this section are used to normalize microarray data and are called normalization protocols. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, abundance values are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

Z-score$_{ij}$=($I_{ij}$−$mnI_i$)/$sdI_i$, and

Zdiff$_j(x,y)$=Z-score$_{xj}$−Z-score$_{yj}$ where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $Im_{ij}$=($I_{ij}$/median$I_i$).

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used in this application, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $Im_{ij}$=log(1.0+($I_{ij}$/median$I_i$)).

Yet another normalization protocol is the Z-score standard deviation log of intensity protocol. In this protocol, raw expression intensities are normalized by the mean log intensity ($mnLI_i$) and standard deviation log intensity ($sdLI_i$). For microarray data, the mean log intensity and the standard deviation log intensity is computed for the log of raw intensity of control genes. Then, the Z-score intensity Zlog-S$_{ij}$ for probe i and spot j is:

Z log $S_{ij}$=(log($I_{ij}$)−$mnLI_i$)/$sdLI_i$.

Still another normalization protocol is the Z-score mean absolute deviation of log intensity protocol. In this protocol, raw intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity Z log A$_{ij}$ for probe i and spot j is:

Z log $A_{ij}$=(log($I_{ij}$)−$mnLI_i$)/$madLI_i$.

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used in this application, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

An intensity dependent normalization can be implemented in R, a language and environment for statistical computing and graphics. In a specific embodiment, the normalization method uses a lowess( ) scatter plot smoother that can be applied to all or a subgroup of probes on the array. For a description of lowess( ), see, for example, Becker et al., "The New S Language," *Wadsworth and Brooks/Cole* (S version), 1988; Ripley, 1996, *Pattern Recognition and Neural Networks*, Cambridge University Press; and Cleveland, 1979, *J. Amer. Statist. Assoc.* 74, 829:836, each of which is hereby incorporated by reference in its entirety.

5.9.2 Standardization Techniques

Gene expression profiles comprising transcript abundance values may be standardized prior to being used for training a classifier to reduce technical variation incurred by different processing conditions. A gene expression profile comprising transcript abundance values of a test biological sample to be classified also may be standardized prior to use. The transcript abundance levels from the matched pairs may be standardized prior to being used for training a classifier useful for classifying a phenotypic characterization of interest. (Preferably, the transcript abundance level data from the matched pairs are not standardized before identifying the highly-correlated genes.) Any standardization technique known in the art can be used to standardize the expression profiles.

For example, microarray expression data may be standardized by dividing the log-expression values on a microarray by the mean expression of all genes across the microarray. This approach works well if the relation between abundance for a given gene (which is the quantity microarrays are designed to measure) and hybridization signal measured by the scanner is approximately linear across replicate samples. As established in Bolstad et al. 2003, Bioinformatics 19, 185-193, and Moraleda et al., 2004, Proceedings of the American Society of Clinical Oncology annual meeting Vol. 23, each of which is hereby incorporated by reference herein, this relation is non-linear for common microarray designs and typical clinical samples, saturating at higher levels of mRNA abundance.

In some embodiments, housekeeping genes may be used for standardization. See, for example, Kohane et al., 2003 *Microarrays for Integrative Genomics* The MIT Press, 2003. It is an assumption of this method that genes with similar levels of expression are affected in similar ways by the obscuring variations. This idea is the basis for other methods of microarray standardization, including quantile normalization (Bolstad et al. 2003, Bioinformatics 19, 185-193, which is hereby incorporated by reference herein) and invariant set normalization (Li et al., 2003, *The Analysis of Gene Expression Data: Methods and Software*, Springer, pp. 120-141, which is hereby incorporated by reference herein). Quantile normalization considers a set of arrays, and normalizes each against all others such that the quantiles of all arrays agree after the normalization. Invariant set normalizes a pair of arrays at a time such that the non-differentially expressed genes in the two arrays have similar ranks after the normalization. Housekeeping genes and their utility in microarray studies has been recognized previously. See, for example, Warrington et al., 2000, Physiol. Genomics 2, 143-147; and de Kok et al., 2005, Laboratory Investigation 85, 154-159, each of which is hereby incorporated by reference herein in its entirety.

In some embodiments, prior to determining the phenotypic characterization of the sample, abundance data for the sample is standardized. The abundance data for the transcripts in nucleic acid preparations derived from the biological sample may be standardized using the systems or methods disclosed in U.S. patent application Ser. No. 12/378,187, entitled "Systems and Methods for Standardization of Microarray Data for Diagnostic Use," filed on Jan. 10, 2009, which is incorporated by reference herein in its entirety.

A kernel transformation standardization method disclosed in application Ser. No. 12/378,187, which is applicable to this invention, is illustrated in FIGS. 7A-7B and 8. In some embodiments according to this standardization method, different standardization reference arrays for use in standardizing expression profiles derived from biological samples of a given sample type are generated by varying the set of gene used for the standardization based on the consistent behavior of the abundance levels for the respective transcripts in nucleic acid preparations derived from training biological samples of that given sample type (such as FFPE biological samples). Following is a description of the steps in the kernel transformation standardization method.

Step 702.

A plurality of training microarray datasets 46 is received. In some embodiments, the plurality of training microarray datasets 46 comprise microarray datasets for at least one phenotypic characterization, at least two different phenotypic characterizations, at least three different phenotypic characterizations, at least four different phenotypic characterizations, or at least five different phenotypic characterizations, at least ten different phenotypic characterizations, at least fifty different phenotypic characterizations, at least five hundred different phenotypic characterizations, at least one thousand different phenotypic characterizations, at least ten thousand different phenotypic characterizations, or between ten and one thousand phenotypic characterizations.

Step 704.

In step 704, each respective training microarray dataset 46 is standardized by dividing each transcript abundance level in the respective training microarray dataset by a measure of central tendency for all the transcript abundance levels in the respective training microarray dataset. The measure of central tendency can be, for example, a geometric mean, an arithmetic mean, median or mode of all of the transcript abundance levels 50 in the respective training microarray dataset 46.

Step 706.

In typical embodiments, each of the training microarray datasets 46 contain abundance values for the same respective transcripts in nucleic acid preparations derived from biological samples. It is possible that some training microarray datasets 46 do not have abundance values for all of these transcripts. In step 706, the plurality of transcripts represented by the training microarray datasets 46 in the training microarray dataset data store 44 are divided into a plurality of abundance bins based on the measured abundance values for the transcripts in the training microarray datasets 46. Each of the abundance bins represents a different abundance value range exhibited by the plurality of transcripts in the plurality of training microarray datasets 46. In some embodiments, the plurality of abundance bins is between 3 and 50 abundance bins, between 3 and 40 abundance bins, between 3 and 30 abundance bins, or between 3 and 15 abundance bins. In some embodiments, a measure of central tendency is determined for each transcript for which abundance data is available in training microarray dataset data store 44 across the training microarray datasets 46 in the data store. Transcripts in the plurality of transcripts are then ranked. Then each transcript is assigned to one abundance bin in a plurality of abundance bins based on the ranked measure of central tendency for the transcript.

The measure of central tendency for a given transcript can be, for example, a geometric mean, an arithmetic mean, median or mode of the given transcript abundance level 50 across the training microarray datasets 46 in the training microarray dataset data store 44. In some embodiments, a first range of measured abundance values of transcripts in a first abundance bin in the plurality of abundance bins overlaps a second range of measured abundance values of transcripts in a second abundance bin in the plurality of abundance bins. In some embodiments, a first range of measured abundance values of transcripts in a first abundance bin in the plurality of abundance bins does not overlap a second range of measured abundance values of transcripts in a second abundance bin in the plurality of abundance bins.

In some embodiments, each abundance bin in the plurality of abundance bins is assigned transcripts in an abundance value range that does not overlap the abundance value range of any other abundance bin in the plurality of abundance bins. In some embodiments, the abundance value range for each abundance bin in the plurality of abundance bins is chosen so that approximately equal numbers of transcripts are assigned to each of the abundance bins based on transcript abundance levels.

Step 708.

In step 708, a measure of variability is computed for each transcript in the plurality of transcripts for which abundance data is available in the training microarray dataset data store 44. In some embodiments, the measure of variability computed for each respective transcript is based upon a coefficient of variation of transcript abundance level of the respective transcript across the training microarray datasets 46 in training microarray dataset data store 44. Examples of measures of variability of the abundance value for a given transcript across the training microarray datasets 46 include, but are not limited to, standard deviation, variance, range, and interquartile range of the abundance value of the transcript across the training microarray datasets 46.

Step 708 does not require that there be a transcript abundance level for a given gene in each of the training microarray datasets. A measure of variability of the abundance value for a given transcript is computed based upon those training microarray datasets 46 in which there was an abundance value for the given transcript.

Step 710.

Step 708 designated, for each respective abundance bin in the plurality of abundance bins, a predetermined number of transcripts in the respective abundance bin having the lowest abundance variability (as compared to the variability of the other transcripts in the respective abundance bin) are designated to be part of a candidate standardization data structure. For example, in one embodiment, the fifty transcripts in each abundance bin having the lowest measure of transcript abundance level variability are designated to be part of a candidate standardization data structure. In some embodiments, the predetermined number is 2, 3, 4, 5, 6, 7, 8, 9, 10, or more than 10 transcripts. In some embodiments, the predetermined number is 10 or more transcripts, 40 or more transcripts, or 100 or more transcripts. In some embodiments, the predetermined number is up to five percent of the transcripts in the respective abundance bin that have the lowest transcript abundance level variability (as compared to the remaining transcripts in the respective abundance bin). In some embodiments, the predetermined number is up to ten percent, up to fifteen percent, up to twenty percent, or up to twenty-five percent of the transcripts in the respective abundance bin that have the lowest transcript abundance level variability (as compared to the remaining transcripts in the respective abundance bin).

Step 712.

In step 712, a reference value for each respective transcript in the candidate reference data structure is calculated as a measure of central tendency of that transcript across the training microarray datasets 46 in the training microarray dataset data store 44. The measure of central tendency for each respective transcript can be, for example, a geometric mean, an arithmetic mean, a median or a mode of the abundance of each respective transcript across the training microarray datasets in the training microarray dataset data store 44. Thus, consider the case in which the measure of central tendency is an average. Thus, in this case, the average of the abundance of transcript 1 in the candidate standardization data structure across the training microarray datasets 46 in the training microarray dataset data store 44 is computed, the average of the abundance of transcript of transcript 2 in the candidate standardization data structure across the training microarray datasets 46 in the training microarray dataset data store is computed, and so forth until an average is been computed for each of the transcripts in the candidate standardization data structure.

Step 712 does not require that there be a transcript abundance level for a given transcript in each of the training microarray datasets 46 in the training microarray dataset data store 44. For example, an average for a given transcript can simply be computed based upon those training microarray datasets 46 in which there is an abundance value for the given transcript.

Step 714.

In step 714, a determination is made as to whether a previous instance of the candidate standardization data structure has been computed. The first time steps 706 through 712 are performed (i.e., the first instance of steps 706 through 712), condition 714 will be 714—No and process control will shift to step 718 because a previous instance of the candidate standardization data structure has not been computed. The second and later times steps 706 through 712 are performed, condition 714 will be 714—Yes and process control will shift to step 716 because a previous instance of the candidate standardization data structure has been computed.

Steps 718-722.

In steps 718 through 722, each of the transcript values in the training microarray datasets 46 in the training microarray dataset data store is transformed using a kernel transformation based upon the candidate standardization data structure computed in the previous instance of steps 706-712 (i.e., the last time steps 706-712 were run). Typically, this is performed on a training microarray dataset 46 by training microarray dataset 46 basis. For example, in step 718, a training microarray dataset 46 is selected. In step 720, for each respective transcript abundance level in the selected training microarray dataset, the respective transcript abundance level is transformed using a kernel transformation based upon the candidate standardization data structure.

In one embodiment, the kernel transformation transforms a transcript abundance level x in the training microarray dataset to the transcript abundance level y by the formula:

$$y = \frac{\sum_{j=0}^{m-1} w_j \cdot (t_j + s \cdot (x - h_j))}{\sum_{j=0}^{m-1} w_j}$$

where
- j is an index to a set of values C of cardinality m of transcript abundance level in the candidate standardization data structure having values within a threshold value w of x;
- $t_j$ is a value of central tendency, for a transcript j, in the set of values C that is stored in the candidate standardization data structure;
- $h_j$ is a transcript abundance level for the transcript j in the training microarray dataset selected in step 718;
- $w_j$ is $$1 - \left|\frac{x - h_j}{w}\right|^p;$$

- w is the kernel function half-width (for example, 1.5);
- p is the kernel function parameter (for example 1); and $$s = \frac{t_{max} - t_{min}}{x_{max} - x_{min}}$$

- $t_{max}$=the median value of a highest portion of the transcript abundance levels in the candidate standardization data structure;
- $t_{min}$=the median value of a lowest portion of the transcript abundance levels in the candidate standardization data structure;
- $x_{max}$=the median value of the transcripts in the training microarray dataset selected in step 718 that are the same as the transcripts that form the highest portion of the transcript abundance levels in the candidate standardization data structure; and
- $x_{min}$=the median value of the transcripts in the training microarray dataset selected in step 718 that are the same as the transcripts that form the lowest portion of the transcript abundance levels in the candidate standardization data structure.

In some embodiments, the highest portion of the transcript abundance levels in the candidate standardization data structure is the highest q quantile of transcript abundance levels in the candidate standardization data structure, where the q quantile is expressed on the 0 to 1 scale. In some embodiments, the lowest portion of the transcript abundance levels in the candidate standardization data structure is the lowest q quantile of transcript abundance levels in the candidate standardization data structure, where the q quantile is between 0 and 1. For example, in one embodiment, q is 0.1 and, therefore,

- the highest q quantile of transcript abundance level central tendency values in the candidate standardization data structure are the transcript abundance levels that are in the upper ten percent, in terms of the transcript abundance level central tendency values, in the candidate standardization data structure, and
- the lowest q quantile of transcript abundance level central tendency values in the candidate standardization data structure are the transcript abundance levels that are in the lower ten percent, in terms of the transcript abundance level central tendency values, in the candidate standardization data structure.

The kernel transformation for a given transcript abundance level x is illustrated in FIG. 8. In FIG. 8, each $t_j$ is the transcript abundance level measure of central tendency for a transcript j, in the set C that is stored in the standardization data structure and $w_i$ are weights assigned to each $t_i$. Further, each si is a smoothed target value computed in the manner described below. In some embodiments w is between 0.1 and 2.0. In one embodiment, w is 1.5. In some embodiments, p is between 0.1 and 3.0. In one embodiment p is 1. In some embodiments $t_j$ is an average transcript abundance level, for a transcript j, in the set of values C that is stored in the candidate standardization data structure.

This kernel transformation is performed for each transcript in the microarray datasets selected in the last instance of step 718. In step 722, a determination is made as to whether each of the training microarray datasets 46 in the training microarray dataset data store 44 have been normalized. If not (722—No), control passes to step 718 where an additional microarray is selected. If so, (722—Yes), control passes to step 706 and loop 706-716 is repeated.

Step 716.

Loop 706-716 is repeated until the percent similarity between the transcripts in the new candidate data structure and the previous candidate data structure is deemed above a threshold value. Step 716 determines whether the percent similarity between the transcripts in the new candidate data structure and the previous candidate data structure is deemed above a threshold value. In some embodiments, this threshold value is at least sixty percent, at least seventy percent, at least eighty percent, at least ninety percent, at least ninety-five percent, at least ninety-nine percent or at least 100 percent.

In some embodiments, the threshold value is ninety percent. This means that at least ninety percent of the transcripts in the standardization data structure after the last iteration of loop 706-716 are found in the standardization data structure computed by the iteration of loop 706-716 that was run just prior to the last iteration of loop 706-716. In some embodiments, the threshold value is eighty percent.

In some embodiments, a percent similarity between the identity of the transcripts in the last candidate standardization data structure and the identity of the transcripts in a previous instance of the candidate standardization data structure is deemed above a threshold value when there are less than one hundred transcripts in the candidate standardization data structure that are not in a previous instance of the candidate standardization data structure.

In some embodiments, a percent similarity between the identity of the transcripts in the last candidate standardization data structure and the identity of the transcripts in a previous instance of the candidate standardization data structure is deemed above a threshold value when there are less than fifty transcripts in the candidate standardization data structure that are not in a previous instance of the candidate standardization data structure.

In some embodiments, a percent similarity between the identity of the transcripts in the last candidate standardization data structure and the identity of the transcripts in a previous instance of the candidate standardization data structure is deemed above a threshold value when there are less than five transcripts in the candidate standardization data structure that are not in a previous instance of the candidate standardization data structure.

In some embodiments, a percent similarity between the identity of the transcripts in the last candidate standardization data structure and the identity of the transcripts in a previous instance of the candidate standardization data structure is deemed above a threshold value when loop 706-716 (consisting of steps 706-722 as needed) have been repeated two or more times, three or more times, four or more times, or five or more times.

Steps 722-730.

Once the percent similarity between the new candidate standardization data structure and the previous data structure is deemed above a threshold (716—Yes), process control ultimately passes to step 728 where the standardization data structure is outputted to a user interface device, a monitor, a computer-readable storage medium, a computer-readable memory, or a local or remote computer system; or the standardization data structure is displayed. As illustrated in Step 730, the standardization data structure comprises an identity, and for each identity, a standardized value. In the standardization data structure produced by the method of FIGS. 7A-7B, each identity is the identity of a transcript. For each respective transcript identity in the standardization data structure, there is a corresponding standardization value for the respective transcript that is a measure of central tendency of the transcript across all of the training microarray datasets 46 in the training microarray dataset data store.

Once the standardization data structure has been constructed it can be used to standardize an unstandardized microarray dataset, where the unstandardized microarray dataset comprises abundance values for a plurality of transcripts. In the method, a standardization data structure is applied to each of the abundance values in the unstandardized microarray dataset thereby computing a standardized microarray dataset. Here, the standardization data structure comprises a plurality of values of central tendency and a transcript identifier for each respective value of central tendency. The plurality of values of central tendency is derived from the training microarray datasets using the method described above. Advantageously, there is no requirement that the unstandardized microarray dataset be included in the training microarray datasets that were used to construct the standardize data structure.

The application of the standardization data structure to an abundance value in the unstandardized microarray dataset comprises transforming the abundance value x for the transcript in the unstandardized microarray dataset to the transcript abundance level y in the standardized unstandardized microarray dataset by the formula:

$$y = \frac{\sum_{j=0}^{m-1} w_j \cdot (t_j + s \cdot (x - h_j))}{\sum_{j=0}^{m-1} w_j}$$

where j is an index to a set of values C of cardinality m of central tendency in the standardization data structure having values within a threshold value w of x;

$t_j$ is a value of central tendency, for a transcript j, in the set C that is stored in the standardization data structure;

$h_j$ is a transcript abundance level for the transcript j in the unstandardized microarray dataset;

$w_j$ is $$1 - \left| \frac{x - h_j}{w} \right|^p ;$$

w is the kernel function half-width;
p is the kernel function parameter,
s is an average slope of the kernel function;

$$s = \frac{t_{max} - t_{min}}{x_{max} - x_{min}}$$

$t_{max}$=the median value of a highest portion of the plurality of values of central tendency in the standardization data structure;

$t_{min}$=the median value of a lowest portion of the plurality of values of central tendency in the standardization data structure;

$x_{max}$=the median value of the transcripts in the plurality of transcripts of the unstandardized microarray dataset that are the same as the transcripts that form the highest portion of the plurality of values of central tendency in the standardization data structure; and $x_{min}$=the median value of the transcripts in the plurality of transcripts of the unstandardized microarray dataset that are the same as the transcripts that form the lowest portion of the plurality of values of central tendency in the standardization data structure.

In some embodiments, the highest portion of the plurality of values of central tendency is the highest q quantile of the plurality of values of central tendency and the lowest portion of the plurality of values of central tendency is the lowest q quantile of the plurality of values of central tendency in the standardization data structure, where q is between 0 and 1 (for example, 0.1, meaning that the top 10 percent and bottom 10 percent are used).

Once the standardization data structure has been applied to each of the abundance values in the unstandardized microarray dataset using the kernel transformation described above, the standardized microarray dataset is outputted to a user, a user interface device, a monitor, a computer-readable storage medium, a computer-readable memory, or a local or remote computer system, or the standardized test microarray dataset is displayed. In some embodiments, the unstandardized microarray dataset is received from a remote source over a wide area network and the standardized microarray dataset is communicated to the remote source over the wide area network.

A rank-based standardization method disclosed in application Ser. No. 12/378,187, which also is applicable to this invention, is illustrated in FIGS. 9A-9D. Following is a description of the steps in the rank-based standardization method.

Step 902.

In step 902 of FIG. 9A, the plurality of training microarray datasets 46 is considered as a two-dimensional table.

Each column is a training microarray datasets 46 and each row is a transcript abundance level 50 in the training microarray datasets. Thus, each box in the two-dimensional table of step 902 represents an abundance level for a transcript in a training microarray dataset 46.

Step 904.

In step 904, the individual transcript abundance levels are ranked on a column by column basis. In one ranking approach, transcript abundance levels in a given training microarray dataset 46 are ranked from most abundant (top of the column) to least abundant (bottom of the column). In another ranking approach, transcript abundance levels in a given training microarray dataset 46 are ranked from least abundant (top of the column) to most abundant (bottom of the column). In step 904, there is no guarantee that each of the transcript abundance levels in a given row of the table is the same after ranking. For example, transcript abundance level "A" may be the most abundant in the first training microarray datasets 46 but only the second most abundant in the second training microarray datasets 46. So, in step 904, transcript abundance level "A" would be in the top cell for the first training microarray datasets 46 but in the cell below the top cell for the second training microarray datasets 46 (in embodiments where transcript abundance levels are ranked from most abundant to least abundant). This point is illustrated in FIG. 9B which provides an illustration of the algorithm of FIG. 9A using exemplary data. As illustrated in step 902, each cell in the top row is the transcript abundance level $eg_1$. But, when the transcript abundance levels are ranked by abundance value in step 904, it is seen that, for many of the exemplary training microarray datasets 46, the most abundant transcript abundance level is $eg_6$ (those exemplary training microarray datasets 46 in which $eg_6$ rises to the top row of the two-dimensional chart). However, for exemplary training microarray dataset $X_2^s$, transcript abundance level $eg_2$ is the most abundant and for exemplary training microarray dataset $X_7^s$, transcript abundance level $eg_p$ is the most abundant. In the sorted two-dimensional table 904, each transcript abundance level in a row (collection of transcript abundance levels) is the transcript abundance level for a transcript from a different training microarray dataset 46 having the same transcript abundance level ranking in the different training microarray datasets.

Step 906.

In step 906, a measure of central tendency is taken for each row of the sorted two-dimensional table 904. In some embodiments, the measure of central tendency is an average. In such embodiments, the average value across each row is taken as illustrated in FIG. 9A. That means that, for a given row in the sorted two-dimensional table 904, each element in the row is averaged together to form a value E as illustrated in FIG. 9A. In various embodiments, the measure of central tendency taken across each row of the sorted two-dimensional table 904 is a geometric mean, an arithmetic mean, median or mode of a collection of transcript abundance levels in the plurality of training microarray datasets.

Step 908.

In step 908, the measure of central tendency for each row, and the identity of each row is stored as a standardization data structure. In this standardization data structure, the identity of each is the transcript abundance level ranking of the two-dimensional table 904. Thus, for example, in the first row of the standardization data structure of FIG. 9A, the identity is 1, which means that the corresponding measure of central tendency is the measure of central tendency for the most abundant transcript abundance level in each of the training microarray datasets 46 (in those embodiments where step 904 involves ranking from most abundant to least abundant transcript abundance level in each training microarray datasets 46).

Once the standardization data structure has been constructed, it can be used to standardize test microarray datasets 68 as illustrated in FIGS. 9C and 9D. FIGS. 9C and 9D illustrate a method in which each measure of central tendency in the standardization data structure is for a set of transcript abundance levels where each transcript abundance level in the set is the transcript abundance levels of a transcript from a different training microarray dataset in the plurality of training microarray datasets that has the same ranking. The identifier for each transcript abundance level in the standardization data structure is the transcript abundance level ranking of the transcript abundance level in the training microarray datasets. In the method, the standardization data structure is applied to the transcript abundance levels of each transcript in the test microarray dataset. For a given transcript abundance level in the test microarray dataset having a transcript abundance level x, this applying comprises transforming the abundance level x for the transcript to the transcript abundance level y in the standardized test microarray dataset by (i) determining a rank of the abundance level x for the transcript in a ranking of the first plurality of transcript abundance levels in the test microarray dataset. Then, the transcript abundance level is assigned the value y in the standardized test microarray dataset, where y is the value of central tendency in the values of central tendency in the standardization data structure that has the same rank as the rank of the transcript abundance level x.

Step 950.

In FIG. 9C, for example, at step 950 there is a test microarray dataset 68 that is to be standardized.

Step 952.

At step 952, the transcript abundance levels in the test microarray dataset 68 are ranked in the same manner that training microarray datasets 46 were ranked in step 904 of FIG. 9A. Once ranked in this manner, the ranking of the individual transcript abundance levels within the test microarray dataset 68 serve as an index into the standardization data structure. For example, the $10^{th}$ most abundant transcript abundance level in the test microarray dataset 68 has the index "10" (in those embodiments in which the dataset is ranked from most abundant to least abundant in step 952) and is thus equated to the $10^{th}$ value in the standardization data structure.

Step 954.

In step 954, each respective transcript abundance level in the test microarray dataset 68 is replaced with the value in the standardization data structure that has the same index as the respective transcript abundance level. For example, the $1^{st}$ ranked transcript abundance level in the test microarray dataset 68 is replaced with the $1^{st}$ ranked value in the standardization data structure, the $2^{nd}$ ranked transcript abundance level in the test microarray dataset 68 is replaced with the $2^{nd}$ ranked value in the standardization data structure, and so forth thereby creating the standardized test microarray dataset with standardized values. In the approach illustrated in FIG. 2, the test microarray dataset 68 must have the same number of transcript abundance levels as the training microarray datasets 46 so that, when the transcript abundance levels of the test microarray dataset 68 are ranked, their ranking serves as an exact index into standardization data structure in the manner described above.

FIG. 9D provides an illustration of the standardization method of FIG. 9C. In step 950 of FIG. 9D, a test microarray dataset 68 having transcript abundance levels (eg$_1$, eg$_2$, eg$_3$, eg$_4$, eg$_5$, eg$_7$, . . . , eg$_p$) is obtained. In step 954, the transcript abundance levels of the test microarray dataset 68 are ranked based on their abundance values such that the order of the transcript abundance levels is now {eg$_1$, eg$_2$, eg$_3$, eg$_4$, eg$_5$, eg$_7$, . . . , egp}. In step 954, ranked transcript abundance levels are replaced with the value having the same index from the standardization data structure. For example, eg$_2$ (ranked first in step 952 of FIG. 9D) is replaced with the first value in the standardization data structure (E$_1$), eg$_6$ (ranked second in step 952 of FIG. 9D) is replaced with the second value in the standardization data structure (E$_2$), eg$_3$ (ranked third in step 952 of FIG. 9D) is replaced with the third value in the standardization data structure (E$_3$) and so forth thereby constructing, in step 954, the standardization test microarray dataset with standardized values, which corresponds to the test microarray dataset 68.

5.10 Measures of Similarity

The correlation between abundance values of a transcript derived from the first type of biological sample and abundance values of that transcript derived from the second type of biological sample of the matched pairs in the population of matched pairs may be quantified through computation of a measure of similarity between these abundance values. There are many ways in which correlation between the variance in abundance values of a transcript derived from the first type of biological sample and the second type of biological sample of the matched pairs can be computed. Indeed, any statistical method in the art for determining the probability that two datasets are related may be used in accordance with the methods of the present invention in order to identify whether there is a correlation between the abundance values of a transcript derived from the first type of biological sample and the abundance levels of that transcript derived from the second type of biological sample of the matched pairs.

One way to compute the similarity metric sim(p$_{i_1}$, p$_{i_2}$) for each transcript i, where p$_{i_1}$ represents abundance levels of transcript i in nucleic acid preparations derived from the first type of biological sample of the matched pairs in the population of matched pairs and p$_{i_2}$ represents abundance levels of transcript i in nucleic acid preparations derived from the analogous second type of biological sample of the matched pairs in the population of matched pairs, is to compute the negative square of the Euclidean distance. In alternative embodiments, metrics other than Euclidean distance can be used to compute sim(p$_{i_1}$, p$_{i_2}$), such as a Manhattan distance, a Chebychev distance, an angle between vectors, a correlation distance, a standardized Euclidean distance, a Mahalanobis distance, a squared Pearson correlation coefficient, or a Minkowski distance. In some embodiments a Pearson correlation coefficient, a squared Euclidean distance, a Euclidean sum of squares, or squared Pearson correlation coefficients is used to determine similarity. Such metrics can be computed, for example, using SAS (Statistics Analysis Systems Institute, Cary, N.C.) or S-Plus (Statistical Sciences, Inc., Seattle, Wash.). Such metrics are described in Draghici, 2003, *Data Analysis Tools for DNA Microarrays*, Chapman & Hall, CRC Press London, chapter 11, which is hereby incorporated by reference herein in its entirety for such purpose.

Correlation based on ranks also is possible, where x$_i$ and y$_i$ are the ranks of the abundance values in ascending or descending numerical order. See for example, Conover, *Practical Nonparametric Statistics*, 2$^{nd}$ ed., Wiley, (1971). Shannon mutual Information also can be used as a measure of similarity. See for example, J. Pierce, 1980, *An Introduction To Information Theory: Symbols, Signals, and Noise*, Dover Publications, which is incorporated by reference herein in its entirety.

The correlation between abundance values of a transcripts over pairs of replicate biological samples also may be quantified through computation of a measure of similarity.

5.11 Classifiers

Various classifiers known in the art can be trained according to the methods described in this application, and used to classify a test biological sample as to a phenotypic characterization. Algorithms are used to produce classifiers capable of accurately predicting phenotypic characterizations of gene expression profiles derived from biological samples.

The classifier may be an algorithm used for classification by applying a non-supervised or supervised learning algorithm to evaluate the gene expression data derived from training experiments. Any standard non-supervised or supervised learning technique known in the art can be used to generate a classifier. Below are non-limiting examples of non-supervised and supervised algorithms known in the art. Given the disclosure in this application, one of skill in the art will appreciate that other pattern classification or regression techniques and algorithms may be used for the classifier and the present invention encompasses all such techniques.

Neural Networks.

In some embodiments, the classifier is learned using a neural network. A neural network is a two-stage regression or classification decision rule. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference herein in its entirety. Neural networks are also described in Draghici, 2003, *Data Analysis Tools for DNA Microarrays*, Chapman & Hall/ CRC; and Mount, 2001, *Bioinformatics: sequence and genome analysis*, Cold Spring Harbor Laboratory Press, Cold Spring Harbor, N.Y., each of which is hereby incorporated by reference herein in its entirety. What are discussed below are some exemplary forms of neural networks.

The basic approach to the use of neural networks is to start with an untrained network, present a training pattern to the input layer, and to pass signals through the net and determine the output at the output layer. These outputs are then compared to the target values; any difference corresponds to an error. For classification, this error can be either squared error or cross-entropy (deviation). See, for example, Hastie et al., 2001, *The Elements of Statistical Learning*, Springer-Verlag, New York, which is hereby incorporated by reference herein in its entirety.

Three commonly used training protocols are stochastic, batch, and on-line. In stochastic training, patterns are chosen randomly from the training set and network weights are updated for each pattern presentation. Multilayer nonlinear networks trained by gradient descent methods such as stochastic back-propagation perform a maximum-likelihood estimation of weight values in the classifier defined by the network topology. In batch training, all patterns are presented to the network before learning takes place. Typically, in batch training, several passes are made through the training data. In online training, each pattern is presented once and only once to the net.

A recurrent problem in the use of three-layer networks is the optimal number of hidden units to use in the network. The number of inputs and outputs of a three-layer network are determined by the problem to be solved. In the present invention, the number of inputs for a given neural network will equal the number of biomarkers selected from Y. The number of output for the neural network will typically be just one. If too many hidden units are used in a neural network, the network will have too many degrees of freedom and if trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

Clustering.

In some embodiments, the classifier is learned using clustering. In some embodiments, abundance values for select transcripts in nucleic acid preparations derived from the biological samples are used to cluster individual biological samples in the training population. For example, consider the case in which ten abundance values for ten corresponding transcripts. Each member m of the training population will have abundance values for each of the ten transcripts. In some embodiments, prior to clustering, the abundance values are normalized to have a mean value of zero and unit variance.

Those members of the training population that exhibit similar expression patterns across the training population will tend to cluster together. A particular combination of abundance levels of transcripts is considered to be a good classifier in this aspect of the invention when the vectors cluster into the phenotypic characterization. Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x) is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973. More recently, Duda et al., Pattern Classification, $2^{nd}$ edition, John Wiley & Sons, Inc. New York, has been published. Pages 537-563 describe clustering in detail. More information on clustering techniques can be found in Kaufman and Rousseceuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Principal Component Analysis.

In some embodiments, the classifier is learned using principal component analysis. Principal component analysis is a classical technique to reduce the dimensionality of a data set by transforming the data to a new set of variable (principal components) that summarize the features of the data. See, for example, Jolliffe, 1986, *Principal Component Analysis*, Springer, New York, which is hereby incorporated by reference herein in its entirety. Principal component analysis is also described in Draghici, 2003, *Data Analysis Tools for DNA Microarrays*, Chapman & Hall/CRC, which is hereby incorporated by reference herein in its entirety. What follows is non-limiting examples of principal components analysis.

Principal components (PCs) are uncorrelated and are ordered such that the $k^{th}$ PC has the $k^{th}$ largest variance among PCs. The $k^{th}$ PC can be interpreted as the direction that maximizes the variation of the projections of the data points such that it is orthogonal to the first k−1 PCs. The first few PCs capture most of the variation in the data set. In contrast, the last few PCs are often assumed to capture only the residual 'noise' in the data.

In one approach to using PCA to learn a classifier, vectors for the select abundance values of transcripts in nucleic acid preparations in Y can be constructed in the same manner described for clustering above. In fact, the set of vectors, where each vector represents the abundance values for the select abundance values of transcripts in nucleic acid preparations derived from a particular member of the training population, can be viewed as a matrix. In some embodiments, this matrix is represented in a Free-Wilson method of qualitative binary description of monomers (Kubinyi, 1990, *3D QSAR in drug design theory methods and applications*, Pergamon Press, Oxford, pp 589-638, hereby incorporated by reference herein), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors, where each vector represents a member of the training population, is plotted. Many different types of plots are possible. In some embodiments, a one-dimensional plot is made. In this one-dimensional plot, the value for the first principal component from each of the members of the training population is plotted. In this form of plot, the expectation is that members of a phenotypic characterization will cluster in one range of first principal component values and members of another phenotypic characterization will cluster in a second range of first principal component values.

In some embodiments, the members of the training population are plotted against more than one principal component. For example, in some embodiments, the members of the training population are plotted on a two-dimensional plot in which the first dimension is the first principal component and the second dimension is the second principal component.

Nearest Neighbor Analysis.

In some embodiments, the classifier is learned using nearest neighbor analysis. Nearest neighbor classifiers are memory-based and require no classifier to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_o\|.$$

Typically, when the nearest neighbor algorithm is used, the abundance data from Y used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of abundance values of transcripts represents the feature space into which members of the test set are plotted. Next, the ability of the training set to correctly characterize the members of the test set is computed. In some embodiments, nearest neighbor computation is performed several times for a given combination of abundance values of transcripts. In each iteration of the computation, the members of the training population are randomly assigned to the training set and the test set. Then, the quality of the combination of biomarkers is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, New York, each of which is hereby incorporated by reference herein in its entirety.

Linear Discriminant Analysis.

In some embodiments, the classifier is learned using linear discriminant analysis. Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the abundance values for the select combinations of transcripts across a subset of the training population serve as the requisite continuous independent variables. The trait subgroup classification (a phenotypic characterization) of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the abundances of a transcript across the training set separates in the groups of the phenotypic characterizations and how these feature values correlate with the feature values of other biomarkers. In some embodiments, LDA is applied to the data matrix of the members in the training sample by the transcripts in a combination of transcripts. Then, the linear discriminant of each member of the training population is plotted. Ideally, those members of the training population representing a phenotypic characterization will cluster into one range of linear discriminant values (for example, negative) and those members of the training population representing another phenotypic characterization will cluster into a second range of linear discriminant values (for example, positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; and Venables & Ripley, 1997, *Modern Applied Statistics with s-plus*, Springer, New York, each of which is hereby incorporated by reference herein in its entirety.

Quadratic Discriminant Analysis.

In some embodiments, the classifier is learned using linear discriminant analysis. Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

Support Vector Machine.

In some embodiments, the classifier is learned using a support vector machine. SVMs are described, for example, in Cristianini and Shawe-Taylor, 2000, *An Introduction to Support Vector Machines*, Cambridge University Press, Cambridge; Boser et al., 1992, "A training algorithm for optimal margin classifiers," in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y., Duda, *Pattern Classification*, Second Edition, 2001, John Wiley & Sons, Inc.; and Hastie, 2001, *The Elements of Statistical Learning*, Springer, New York; and Furey et al., 2000, Bioinformatics 16, 906-914, each of which is hereby incorporated by reference herein in its entirety. When used for classification, SVMs separate a given set of binary labeled data training data with a hyper-plane that is maximally distant from them. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space. For more information on support vector machines see, for example, Furey et al., 2000, Bioinformatics 16, page 906-914, which is hereby incorporated by reference herein.

Decision Tree.

In one embodiment the classifier is a decision tree. Decision trees are described generally in Duda, 2001, *Pattern Classification*, John Wiley & Sons, Inc., New York, pp. 395-396, which is hereby incorporated herein by reference. One specific algorithm that can be used is a classification and regression tree (CART). Other specific algorithms for include, but are not limited to, ID3, C4.5, MART, and Random Forests. CART, ID3, and C4.5, each described in Duda, 2001, *Pattern Classification*, John Wiley & Sons, Inc., New York, pp. 396-408 and pp. 411-412, which is hereby incorporated by reference herein in its entirety. CART, MART, and C4.5 are also described in Hastie et al., 2001, *The Elements of Statistical Learning*, Springer-Verlag, New York, Chapter 9, which is hereby incorporated by reference herein in its entirety. The Random Forests technique is described in Breiman, 1999, "Random Forests—Random Features," Technical Report 567, Statistics Department, University of California at Berkeley, September 1999, which is hereby incorporated by reference herein in its entirety.

In addition to univariate decision trees in which each split is based on a abundance values for a corresponding transcript in Y, or the relative abundance value of two such biomarkers, the classifier can be a multivariate decision tree. In such a multivariate decision tree, some or all of the decisions actually comprise a linear combination of abundance values for a plurality of transcripts. Multivariate decision trees are described in Duda, 2001, *Pattern Classification*, John Wiley & Sons, Inc., New York, pp. 408-409, which is hereby incorporated by reference herein in its entirety.

Multivariate Adaptive Regression Splines.

Another approach that can be used to learn a pairwise probability function $g_{pq}(X, W_{pq})$ uses multivariate adaptive regression splines (MARS). MARS is an adaptive procedure for regression, and is well suited for the high-dimensional problems addressed by the present invention. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference herein in its entirety.

Centroid Classifier Techniques.

In one embodiment a nearest centroid classifier technique is used. Such a technique computes, for the phenotypic characterizations, a centroid given by the average abundance levels of the biomarkers from biological samples in the training population in the phenotypic characterization class (i.e., a specific phenotypic characterization), and then assigns new samples (the test biological sample) to the class whose centroid is nearest. This approach is similar to k-means clustering except clusters are replaced by known classes. This algorithm can be sensitive to noise when a large number of transcripts are used. One enhancement to the technique uses shrinkage: for each transcript used, differences between phenotypic characterization class centroids are set to zero if they are deemed likely to be due to chance. This approach is implemented in the Prediction Analysis of Microarray, or PAM. See, for example, Tibshirani et al., 2002, *Proceedings of the National Academy of Science USA* 99; 6567-6572, which is hereby incorporated by reference herein in its entirety. Shrinkage is controlled by a threshold below which differences are considered noise. Transcripts that show no difference above the noise level are removed. A threshold can be chosen by cross-validation. As the threshold is decreased, more transcripts from a given expression profile are included and estimated classification errors decrease, until they reach a bottom and start climbing again as a result of noise biomarkers—a phenomenon known as overfitting.

Regression.

In some embodiments, the classifier is a regression classifier, such as a logistic regression classifier. Such a regression classifier includes a coefficient for each of the transcripts used to construct the classifier. In such embodiments, the coefficients for the regression classifier are computed using, for example, a maximum likelihood approach. In such a computation, the abundance values for the transcripts are used.

Other Methods.

In some embodiments, the classifier is learned using k-nearest neighbors (k-NN), an artificial neural network (ANN), a parametric linear equation, a parametric quadratic equation, a naive Bayes analysis, linear discriminant analysis, a decision tree, or a radial basis function.

5.12 Apparatus, Computer and Computer Program Product Implementations

The present invention can be implemented as a computer program product that comprises a computer program mechanism embedded in a computer-readable storage medium. Further, any of the methods of the present invention can be implemented in one or more computers or other forms of apparatus. Examples of apparatus include but are not limited to, a computer, and a spectroscopic measuring device (for example, a microarray reader or microarray scanner). Further still, any of the methods of the present invention can be implemented in one or more computer program products. Some embodiments of the present invention provide a computer program product that encodes any or all of the methods disclosed in this application. Such methods can be stored on a CD-ROM, DVD, magnetic disk storage product, or any other computer-readable data or program storage product. Such computer readable storage media are intended to be tangible, physical objects (as opposed to carrier waves). Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave (it will be clear that such use of carrier wave is for distribution, not storage).

Some embodiments of the present invention provide a computer program product that contains any or all of the program modules shown in FIG. 1. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

In a specific embodiment, the computer program provides for outputting a result of the claimed method to a user, a user interface device, a computer readable storage medium, a monitor, a local computer, or a computer that is part of a network. Such computer readable storage media are intended to be tangible, physical objects (as opposed to carrier waves).

5.13 Exemplary Embodiments

This section provides some specific embodiments of the present invention, as follows: In some aspects, the disclosure provides a computer-implemented method of identifying a plurality of protein-coding genes whose transcript levels in nucleic acid preparations derived from biological samples are useful for classifying both a first type of biological sample and a second type of biological sample, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, said method comprising: identifying a plurality of protein-coding genes, each of which has a transcript with an abundance level in a nucleic acid preparation derived from said first type of biological sample of a matched pair that is correlated with an abundance level of said transcript of said protein-coding gene in a nucleic acid preparation derived from the other member of the matched pair, the other member being said second type of biological sample that is analogous to said first type of biological sample, wherein said abundance levels are deemed to be correlated if a measure of similarity between said abundance levels is above a predetermined threshold, and wherein said measure of similarity is computed over a set M of matched pairs, wherein the number of matched pairs in set M is at least 5, at least 10, at least 20, at least 30, at least 50, at least 80, or at least 100.

In some embodiments, the methods described above include outputting to a user, a user interface device, a computer readable storage medium, a monitor, a local computer, or a computer that is part of a network; or displaying, the identities of said identified plurality of protein-coding genes.

In some embodiments, the methods described above include, before said identifying step, steps of standardizing measured abundance levels of mRNAs, nucleic acids derived from the respective mRNAs, cDNAs corresponding to said respective mRNAs, or cRNAs corresponding to said respective mRNAs, in said nucleic acid preparation derived from said first type of biological sample of said matched pair and standardizing measured levels of mRNAs, nucleic acids derived from the respective mRNAs, cDNAs corresponding to said respective mRNAs, or cRNAs corresponding to said respective mRNAs, in said nucleic acid preparation derived from said second type of biological sample of said matched pair, wherein said measured abundance levels in said nucleic acid preparation derived from said first type of biological sample of said matched pair and said measured abundance levels in said nucleic acid preparation derived from said second type of biological sample of said matched pair are all measured amounts of mRNA, all measured amounts of nucleic acids derived from the respective mRNAs, all measured amounts of cDNAs, or all measured amounts of cRNAs.

In some embodiments, the methods described above include, before said identifying step, a step of comparing an expression profile of said first type of biological sample to an expression profile of said second type of biological sample, each said expression profile comprising respective expression levels of said plurality of protein-coding genes in each said biological sample.

In some embodiments, the methods described above include, before said identifying step and after said standardizing steps, a step of comparing an expression profile of said first type of biological sample to an expression profile of said second type of biological sample, each said expression profile comprising respective expression levels of said plurality of protein-coding genes in each said biological sample.

In some embodiments of the methods described above, said abundance levels used in said identifying step are not standardized abundance levels.

In some aspects, the disclosure includes a computer-implemented method of training a classifier for classifying biological samples as to a phenotypic characterization comprising performing the method of any one of the embodiments described above, and further comprising training a classifier for classifying biological samples as to a phenotypic characterization using abundance levels of respective transcripts of a set of genes in nucleic acid preparations derived from training biological samples from subjects having said phenotypic characterization, wherein said identified plurality of protein-coding genes are at least 90% of said set, said set containing at least 111 genes.

In some embodiments, the methods described above include outputting to a user, a user interface device, a computer readable storage medium, a monitor, a local computer, or a computer that is part of a network; or displaying, one or more parameters of said classifier.

In some embodiments of the methods described above, said phenotypic characterization is selected from the group consisting of presence of a disease or disorder, tissue of origin of a cancer of unknown primary, response to a treatment, aggressiveness or stage of a disease, identity of an infectious agent responsible for the presence of an infection, tissue type, strain of an infectious agent responsible for the presence of an infection, age of the subject, and gender of the subject.

In some embodiments of the methods described above, said classifier classifies as to multiple phenotypic characterizations, wherein said multiple phenotypic characterizations belong to a same phenotypic category.

In some embodiments of the methods described above, said phenotypic category is a tissue of origin of a cancer of unknown primary.

In some embodiments of the methods described above, said multiple phenotypic characterizations are different tissues of origin of a cancer of unknown primary.

In some embodiments of the methods described above, said different tissues of origin are selected from the group consisting of bladder, breast, cholangiocarcinoma/gallbladder, central nervous system, colorectal, endometrial, gastric, germ cell, head and neck squamous cell carcinomas, malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid.

In some embodiments of the methods described above, said plurality of protein-coding genes is at least 100 genes, at least 111 genes, at least 125 genes, at least 150 genes, at least 200 genes, at least 500 genes, at least 1000 genes, at least 1500 genes, at least 2000 genes, at least 2500 genes, at least 3000 genes, at least 3500 genes, at least 4000 genes, at least 5000 genes, at least 6000 genes, at least 7500 genes, or at least 10,000 genes.

In some embodiments of the methods described above, said predetermined threshold is a central tendency of a distribution of values of a measure of similarity, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is higher than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is lower than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said pairs of replicate said second type of biological samples are of the same tissue type of malignancy as said second type of biological sample.

In some embodiments of the methods described above, said measure of similarity is a Pearson correlation coefficient.

In some embodiments of the methods described above, said central tendency is a median.

In some embodiments, the methods described above include a step of computing said values of said measure of similarity to provide said distribution of values of said measure of similarity.

In some embodiments, the methods described above include, before said identifying step, a step of measuring said abundance levels in said nucleic acid preparations derived from said first type of biological sample and said abundance levels in said nucleic acid preparations derived from said second type of biological sample by measuring abundance levels of the respective mRNAs, abundance levels of nucleic acids derived from the respective mRNAs, abundance levels of cDNAs corresponding to said respective mRNAs, or abundance levels of cRNAs corresponding to said respective mRNAs.

In some embodiments of the methods described above, said first type of biological sample of said matched pair is a fixed biological sample that has been fixed with a crosslinking agent In some embodiments of the methods described above, said first type of biological sample of said matched pair is a formalin-fixed paraffin-embedded biological sample.

In some embodiments of the methods described above, said second type of biological sample of said matched pair is a fresh biological sample, a frozen biological sample, or a biological sample that has been preserved with a non-crosslinking preservative.

In some embodiments of the methods described above, said second type of biological sample is a frozen biological sample.

In some embodiments of the methods described above, said first type of biological sample of said matched pair is a FFPE biological sample and said second type of biological sample of said matched pair is a frozen biological sample.

In some embodiments of the methods described above, said training biological samples are fixed biological samples that have been fixed with a same crosslinking agent as said first type of biological sample of said matched pair.

In some embodiments of the methods described above, said training biological samples are formalin-fixed paraffin-embedded biological samples.

In some embodiments of the methods described above, said training biological samples are of a same sample type as said first type of biological sample of said matched pair.

In some embodiments of the methods described above, said training biological samples are of a same sample type as said second type of biological sample of said matched pair.

In some embodiments of the methods described above, said training biological samples are frozen biological samples.

In some embodiments of the methods described above, said plurality of training biological samples comprises biological samples of a same sample type as said first type of biological sample of said matched pair and biological samples of a same sample type as said second type of biological sample of said matched pair.

In some aspects, the disclosure provides a computer-implemented method of training a classifier useful for classifying as to a phenotypic characterization a biological sample, said method comprising: training a classifier for classifying biological samples as to a phenotypic characterization using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples.

In some embodiments, the methods described above include, prior to step (a) the steps of: identifying said protein-coding genes; and standardizing abundance levels of respective transcripts in said set of genes in nucleic acid preparations derived from said plurality of training biological samples, to provide standardized abundance levels, wherein said standardized abundance levels are said abundance levels used in said training step.

In some embodiments, the methods described above include, prior to step (a) the steps of: standardizing measured levels of mRNAs, nucleic acids derived from the respective mRNAs, cDNAs corresponding to said respective mRNAs, or cRNAs corresponding to said respective mRNAs, in said nucleic acid preparation derived from said first type of biological sample of said matched pair, and standardizing measured levels of mRNAs, nucleic acids derived from the respective mRNAs, cDNAs corresponding to said respective mRNAs, or cRNAs corresponding to said respective mRNAs, in said nucleic acid preparation derived from said second type of biological sample of said matched pair, wherein said measured abundance levels in said nucleic acid preparation derived from said first type of biological sample of said matched pair and said measured abundance levels in said nucleic acid preparation derived from said second type of biological sample of said matched pair are all measured amounts of mRNA, all measured amounts of nucleic acids derived from the respective mRNAs, all measured amounts of cDNAs, or all measured amounts of cRNAs, to provide standardized abundance levels; and identifying said protein-coding genes using said standardized abundance levels.

In some embodiments, the methods described above include outputting to a user, a user interface device, a computer readable storage medium, a monitor, a local computer, or a computer that is part of a network; or displaying, one or more parameters of said classifier.

In some embodiments of the methods described above, said phenotypic characterization is selected from the group consisting of presence of a disease or disorder, tissue of origin of a cancer of unknown primary, response to a treatment, aggressiveness or stage of a disease, identity of an infectious agent responsible for the presence of an infection, tissue type, strain of an infectious agent responsible for the presence of an infection, age of the subject, and gender of the subject.

In some embodiments of the methods described above, said training biological samples are from humans.

In some embodiments of the methods described above, said classifier classifies as to multiple phenotypic characterizations, wherein said multiple phenotypic characterizations belong to a same phenotypic category.

In some embodiments of the methods described above, said phenotypic category is a tissue of origin of a cancer of unknown primary.

In some embodiments of the methods described above, said multiple phenotypic characterizations are different tissues of origin of a cancer of unknown primary.

In some embodiments of the methods described above, said different tissues of origin are selected from the group consisting of bladder, breast, cholangiocarcinoma/gallbladder, central nervous system, colorectal, endometrial, gastric, germ cell, head and neck squamous cell carcinomas (SCC), malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid.

In some embodiments of the methods described above, said set of genes comprises at least 100, at least 111, at least 125, at least 150, at least 200, at least 500, at least 1000, at least 1500, at least 2000, at least 2500, at least 3000, at least 3500, at least 4000, at least 5000, at least 6000, at least 7500, or at least 10,000 of said protein-coding genes.

In some embodiments of the methods described above, said predetermined threshold is a central tendency of a distribution of values of a measure of similarity, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is higher than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is lower than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said pairs of replicate said second type of biological samples are of the same tissue type of malignancy as said second type of biological sample.

In some embodiments of the methods described above, said measure of similarity is a Pearson correlation coefficient.

In some embodiments of the methods described above, said central tendency is a median.

In some embodiments, the methods described above include a step of computing said values of said measure of similarity to provide said distribution of values of said measure of similarity.

In some embodiments, the methods described above include before said identifying step, a step of measuring said abundance levels of respective transcripts of said set of genes in nucleic acid preparations derived from said plurality of training biological samples by measuring abundance levels of the respective mRNAs, abundance levels of nucleic acids derived from the respective mRNAs, abundance levels of cDNAs corresponding to said respective mRNAs, or abundance levels of cRNAs corresponding to said respective mRNAs.

In some embodiments, the methods described above include obtaining said abundance levels of respective transcripts of a set of genes in nucleic acid preparations derived from a plurality of training biological samples by a method comprising hybridizing nucleic acids derived from said training biological samples against nucleic acids preparations derived from said second type of biological sample or said first type of biological sample.

In some embodiments of the methods described above, said first type of biological sample of said matched pair is a fixed biological sample that has been fixed with a crosslinking agent.

In some embodiments of the methods described above, said first type of biological sample of said matched pair is a formalin-fixed paraffin-embedded biological sample.

In some embodiments of the methods described above, said training biological samples are fixed biological samples that have been fixed with a same crosslinking agent as said first type of biological sample of said matched pair.

In some embodiments of the methods described above, said training biological samples are formalin-fixed paraffin-embedded biological samples.

In some embodiments of the methods described above, said second type of biological sample of said matched pair is a fresh biological sample, a frozen biological sample, or a biological sample that has been preserved with a non-crosslinking preservative.

In some embodiments of the methods described above, said second type of biological sample of said matched pair is a frozen biological sample.

In some embodiments of the methods described above, said training biological samples are of a same sample type as said first type of biological sample of said matched pair.

In some embodiments of the methods described above, said training biological samples are of a same sample type as said second type of biological sample of said matched pair.

In some embodiments of the methods described above, said training biological samples are frozen biological samples.

In some embodiments of the methods described above, said plurality of training biological samples comprises biological samples of a same sample type as said first type of biological sample of said matched pair and biological samples of a same sample type as said second type of biological sample of said matched pair.

In some embodiments of the methods described above, said first type of biological sample of said matched pair is a FFPE biological sample and said second type of biological sample of said matched pair is a frozen biological sample, and wherein said plurality of training biological samples are frozen biological samples.

In some embodiments of the methods described above, said classifier is useful for classifying as to said phenotypic characterization a biological sample that is of a same sample type as said first type of biological sample of said matched pair.

In some embodiments of the methods described above, said classifier is useful for classifying as to said phenotypic characterization a biological sample that is of a same sample type as said second type of biological sample of said matched pair.

In one aspect, the disclosure provides a computer-implemented method of classifying a test biological sample as to a phenotypic characterization using a classifier, said method comprising: (a) training a classifier for classifying biological samples as to a phenotypic characterization using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples; and (b) processing, using said classifier, abundance levels of respective transcripts of a group of genes in a nucleic acid preparation derived from said test biological sample, wherein said group of genes comprises said protein-coding genes of said set of genes, to classify said test biological sample as to said phenotypic characterization.

In one aspect, the disclosure provides a computer-implemented method of classifying a test biological sample as to a phenotypic characterization using a classifier, said method comprising: (a) processing, using said classifier, abundance levels of respective transcripts of a group of genes in a nucleic acid preparation derived from said test biological sample, to classify said test biological sample as to said phenotypic characterization, wherein said classifier is trained according to a method comprising: training said classifier using abundance levels of respective transcripts of a set of genes in nucleic acid preparations derived from a plurality of training biological samples, said training biological samples being from subjects having said phenotypic characterization; said set of genes containing at least 111 genes, wherein at least 90% of the genes in said set of genes are protein-coding genes, each of which protein-coding genes has a transcript with an abundance level in a nucleic acid preparation derived from a first type of biological sample of a matched pair that is correlated with an abundance level of said transcript of said protein-coding gene in a nucleic acid preparation derived from the other member of the matched pair, the other member being a second type of biological sample that is analogous to said first type of biological sample of the matched pair, wherein said first type of biological sample and said second type of biological sample are each of a sample type independently selected from the group consisting of a fresh biological sample, a frozen biological sample, a biological sample that has been preserved with a non-crosslinking preservative, and a fixed biological sample that has been fixed with a crosslinking agent, wherein said first type of biological sample and said second type of biological sample are not of the same said sample type, wherein said abundance levels in said nucleic acid preparations derived from said first type of biological sample and said abundance levels in said nucleic acid preparations derived from said second type of biological sample are deemed to be correlated if a measure of similarity between said abundance levels is above a predetermined threshold, wherein said measure of similarity is computed over a set M of matched pairs, wherein the number of matched pairs in set M is at least 5, at least 10, at least 20, at least 30, at least 50, at least 80, or at least 100, and wherein said plurality of training biological samples is at least 5 biological samples; and wherein said group of genes comprises said protein-coding genes of said set of genes.

In some embodiments, the methods described above include outputting to a user, a user interface device, a computer readable storage medium, a monitor, a local computer, or a computer that is part of a network; or displaying, from said classifier an indication of said phenotypic characterization.

In some embodiments, the methods described above include, prior to training said classifier, the steps of: (i) identifying a plurality of said protein-coding genes; and (ii) standardizing abundance levels of respective transcripts in said set of genes in nucleic acid preparations derived from said plurality of training biological samples, to provide standardized abundance levels, wherein said standardized abundance levels are said abundance levels used in said training step.

In some embodiments, the methods described above include, prior to training said classifier, the steps of: (i) standardizing measured levels of mRNAs, nucleic acids derived from the respective mRNAs, cDNAs corresponding to said respective mRNAs, or cRNAs corresponding to said respective mRNAs, in said nucleic acid preparation derived from said first type of biological sample of said matched pair, and standardizing measured levels of mRNAs, nucleic acids derived from the respective mRNAs, cDNAs corresponding to said respective mRNAs, or cRNAs corresponding to said respective mRNAs, in said nucleic acid preparation derived from said second type of biological sample of said matched pair, wherein said measured abundance levels in said nucleic acid preparation derived from said first type of biological sample of said matched pair and said measured abundance levels in said nucleic acid preparation derived from said second type of biological sample of said matched pair are all measured amounts of mRNA, all measured amounts of nucleic acids derived from the respective mRNAs, all measured amounts of cDNAs, or all measured amounts of cRNAs, to provide standardized abundance levels; and (ii) identifying a plurality of said protein-coding genes using said standardized abundance levels.

In some embodiments of the methods described above, said phenotypic characterization is selected from the group consisting of presence of a disease or disorder, tissue of origin of a cancer of unknown primary, response to a treatment, aggressiveness or stage of a disease, identity of an infectious agent responsible for the presence of an infection, tissue type, strain of an infectious agent responsible for the presence of an infection, age of the subject, and gender of the subject.

In some embodiments of the methods described above, said training biological samples are from humans.

In some embodiments of the methods described above, said test biological sample is from a human.

In some embodiments of the methods described above, said classifier classifies as to multiple phenotypic characterizations, wherein said multiple phenotypic characterizations belong to a same phenotypic category.

In some embodiments of the methods described above, said phenotypic category is a tissue of origin of a cancer of unknown primary.

In some embodiments of the methods described above, said multiple phenotypic characterizations are different tissues of origin of a cancer of unknown primary.

In some embodiments of the methods described above, said different tissues of origin are selected from the group consisting of bladder, breast, cholangiocarcinoma/gallbladder, central nervous system, colorectal, endometrial, gastric, germ cell, head and neck squamous cell carcinomas (SCC), malignant mesothelioma, neuroendocrine cancer, kidney, hepatocellular, non-small cell lung, non-Hodgkin's lymphoma, melanoma, ovarian, pancreatic, prostate, soft tissue sarcoma, and thyroid.

In some embodiments of the methods described above, said set of genes comprises at least 100, at least 111, at least 125, at least 150, at least 200, at least 500, at least 1000, at least 1500, at least 2000, at least 2500, at least 3000, at least 3500, at least 4000, at least 5000, at least 6000, at least 7500, or at least 10,000 of said protein-coding genes.

In some embodiments of the methods described above, said predetermined threshold is a central tendency of a distribution of values of a measure of similarity, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is higher than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said predetermined threshold is lower than a central tendency of a distribution of values of a measure of similarity by at least 5%, at least 10%, at least 15%, at least 20%, at least 30%, or at least 35% of the value of said central tendency, wherein said measure of similarity is computed for each respective individual gene in a plurality of candidate protein-coding genes, over respective abundance levels of transcript(s) of said individual candidate protein-coding gene in nucleic acid preparations derived from a number of pairs of replicate said second type of biological samples that are of the same tissue type and the same species as said second type of biological sample, and wherein the number of pairs of replicate said second type of biological samples is at least 5, at least 10, at least 20, at least 30, at least 50, at least 80, or at least 100.

In some embodiments of the methods described above, said pairs of replicate said second type of biological samples are of the same tissue type of malignancy as said second type of biological sample.

In some embodiments of the methods described above, said measure of similarity is a Pearson correlation coefficient.

In some embodiments of the methods described above, said central tendency is a median.

In some embodiments, the methods described above include, computing said values of said measure of similarity to provide said distribution of values of said measure of similarity.

In some embodiments, the methods described above include, before said identifying step, a step of measuring said abundance levels of respective transcripts of said set of genes in nucleic acid preparations derived from said plurality of training biological samples by measuring abundance levels of the respective mRNAs, abundance levels of nucleic acids derived from the respective mRNAs, abundance levels of cDNAs corresponding to said respective mRNAs, or abundance levels of cRNAs corresponding to said respective mRNAs.

In some embodiments, the methods described above include, before said identifying step, a step of measuring said abundance levels of respective transcripts of a group of genes in a nucleic acid preparation derived from said test biological sample by measuring abundance levels of the respective mRNAs, abundance levels of nucleic acids derived from the respective mRNAs, abundance levels of cDNAs corresponding to said respective mRNA, or abundance levels of cRNAs corresponding to said respective mRNAs.

In some embodiments, the methods described above include, obtaining said abundance levels of respective transcripts of a group of genes in a nucleic acid preparation derived from said test biological sample by a method comprising hybridizing nucleic acids derived from said test biological sample against nucleic acids preparations derived from said second type of biological sample or said first type of biological sample.

In some embodiments of the methods described above, said first type of biological sample of said matched pair is a fixed biological sample that has been fixed with a crosslinking agent.

In some embodiments of the methods described above, said first type of biological sample of said matched pair is a formalin-fixed paraffin-embedded biological sample.

In some embodiments of the methods described above, said training biological samples are fixed biological samples that have been fixed with a same crosslinking agent as said first type of biological sample of said matched pair.

In some embodiments of the methods described above, said training biological samples are formalin-fixed paraffin-embedded biological samples.

In some embodiments of the methods described above, said second type of biological sample of said matched pair is a fresh biological sample, a frozen biological sample, or a biological sample that has been preserved with a non-crosslinking preservative.

In some embodiments of the methods described above, said second type of biological sample of said matched pair is a frozen biological sample.

In some embodiments of the methods described above, said training biological samples are of a same sample type as said first type of biological sample of said matched pair.

In some embodiments of the methods described above, said training biological samples are of a same sample type as said second type of biological sample of said matched pair.

In some embodiments of the methods described above, said training biological samples are frozen biological samples.

In some embodiments of the methods described above, said plurality of training biological samples comprises biological samples of a same sample type as said first type of biological sample of said matched pair and biological samples of a same sample type as said second type of biological sample of said matched pair.

In some embodiments of the methods described above, said test biological sample is a fixed biological sample that has been fixed with a same crosslinking agent as said first type of biological sample of said matched pair.

In some embodiments of the methods described above, said test biological sample which is a first type of biological sample is a formalin-fixed paraffin-embedded biological sample.

In some embodiments of the methods described above, said test biological sample which is a first type of biological sample is of a same sample type as said first type of biological sample of said matched pair.

In some embodiments of the methods described above, said test biological sample which is a second type of biological sample is of a same sample type as said second type of biological sample of said matched pair.

In some embodiments of the methods described above, said test biological sample which is a second type of biological sample is a frozen biological sample.

In some embodiments of the methods described above, said first type of biological sample of said matched pair is a FFPE biological sample and said second type of biological sample of said matched pair is a frozen biological sample, wherein said plurality of training biological samples are frozen biological sample, and wherein said test biological sample is a FFPE biological sample.

In some embodiments of the methods described above, said first type of biological sample of said matched pair is a FFPE biological sample and said second type of biological sample of said matched pair is a frozen biological sample, wherein said plurality of training biological samples are frozen biological sample, and wherein said test biological sample is a frozen biological sample.

In one aspect, the disclosure provides a computer system for identifying a plurality of protein-coding genes whose transcript levels in nucleic acid preparations derived from biological samples are useful for classifying both biological samples that have been second type of and biological samples that have been first type of, said computer system comprising: one or more processor units; and one or more memory units connected to said one or more processor units, said one or more memory units containing one or more modules which comprise one or more programs which cause said one or more processor units to execute steps comprising: (a) performing a method as described above.

In some embodiments of the computer system described above, said one or more memory units contain one or more modules which comprise one or more programs which cause said one or more processor units to execute steps comprising: (b) after step (a), outputting to a user, a user interface device, a monitor, a computer-readable storage medium, a computer-readable memory, or a local or remote computer system; or displaying, the identities of the identified plurality of protein-coding genes.

In one aspect, the disclosure provides a computer system for training a classifier for classifying biological samples as to a phenotypic characterization, said computer system comprising: one or more processor units; and one or more memory units connected to said one or more processor units, said one or more memory units containing one or more modules which comprise one or more programs which cause said one or more processor units to execute steps comprising: (a) performing a method as described above.

In some embodiments of the computer system described above, said one or more memory units contain one or more modules which comprise one or more programs which cause said one or more processor units to execute steps comprising: (b) after step (a), outputting to a user, a user interface device, a monitor, a computer-readable storage medium, a computer-readable memory, or a local or remote computer system; or displaying, the identities of the identified plurality of protein-coding genes.

In some embodiments of the computer system described above, said one or more memory units contain one or more modules which comprise one or more programs which cause said one or more processor units to execute steps comprising: (b) after step (a), outputting to a user, a user interface device, a monitor, a computer-readable storage medium, a computer-readable memory, or a local or remote computer system; or displaying, one or more parameters of said classifier.

In one aspect, the disclosure provides a computer program product for use in conjunction with a computer having one or more memory units and one or more processor units, the computer program product comprising a computer readable storage medium having a computer program mechanism encoded thereon, wherein said computer program mechanism can be loaded into the one or more memory units of said computer and cause the one or more processor units of the computer to execute steps comprising: (a) performing a method as described above.

In some embodiments of the computer system described above, said computer program mechanism can be loaded into the one or more memory units of said computer and cause the one or more processor units of the computer to execute steps comprising: (b) after step (a), outputting to a user, a user interface device, a monitor, a computer-readable storage medium, a computer-readable memory, or a local or remote computer system; or displaying, the identities of the identified plurality of protein-coding genes.

In some embodiments of the computer system described above, said computer program mechanism can be loaded into the one or more memory units of said computer and cause the one or more processor units of the computer to execute steps comprising performing a method as described above, further comprising: (b) after step (a), outputting to a user, a user interface device, a monitor, a computer-readable storage medium, a computer-readable memory, or a local or remote computer system; or displaying, one or more parameters of said classifier.

In one aspect, the disclosure provides a computer system for training a classifier useful for classifying as to a phenotypic characterization both biological samples that have been second type of and biological samples that have been first type of, said computer system comprising: one or more processor units; and one or more memory units connected to said one or more processor units, said one or more memory units containing one or more modules which comprise one or more programs which cause said one or more processor units to execute steps comprising: (a) performing a method as described above.

In some embodiments of the computer system described above, said one or more memory units containing one or more modules which comprise one or more programs which cause said one or more processor units to execute steps comprising: (b) after step (a), outputting to a user, a user interface device, a monitor, a computer-readable storage medium, a computer-readable memory, or a local or remote computer system; or displaying, one or more parameters of said classifier.

In one aspect, the disclosure provides a computer program product for use in conjunction with a computer having one or more memory units and one or more processor units, the computer program product comprising a computer readable storage medium having a computer program mechanism encoded thereon, wherein said computer program mechanism can be loaded into the one or more memory units of said computer and cause the one or more processor units of the computer to execute steps comprising: performing a method as described above.

In some embodiments of the computer system described above, said computer program mechanism can be loaded into the one or more memory units of said computer and cause the one or more processor units of the computer to execute steps comprising: (b) after step (a), outputting to a user, a user interface device, a monitor, a computer-readable storage medium, a computer-readable memory, or a local or remote computer system; or displaying, one or more parameters of said classifier.

In one aspect, the disclosure provides a computer system for classifying a test biological sample as to a phenotypic characterization using a classifier, said computer system comprising: one or more processor units; and one or more memory units connected to said one or more processor units, said one or more memory units containing one or more modules which comprise one or more programs which cause said one or more processor units to execute steps comprising: performing a method as described above.

In some embodiments of the computer system described above, said one or more memory units containing one or more modules which comprise one or more programs which cause said one or more processor units to execute steps comprising: (b) after step (a), outputting to a user, a user interface device, a monitor, a computer-readable storage medium, a computer-readable memory, or a local or remote computer system; or displaying, from said classifier an indication of said phenotypic characterization.

In one aspect, the disclosure provides a computer program product for use in conjunction with a computer having one or more memory units and one or more processor units, the computer program product comprising a computer readable storage medium having a computer program mechanism encoded thereon, wherein said computer program mechanism can be loaded into the one or more memory units of said computer and cause the one or more processor units of the computer to execute steps comprising: performing a method as described above.

In some embodiments of the computer system described above, said computer program mechanism can be loaded into the one or more memory units of said computer and cause the one or more processor units of the computer to execute steps comprising: (b) after step (a), outputting to a user, a user interface device, a monitor, a computer-readable storage medium, a computer-readable memory, or a local or remote computer system; or displaying, from said classifier an indication of said phenotypic characterization.

6. Example: Classification of Formalin-Fixed Paraffin-Embedded Biological Samples In this example, highly-correlated genes were identified using a method of Section 5.2. Different classifiers were trained using standardized abundance levels of respective transcripts of differing numbers of the highly-correlated genes, using a method of Section 53. The classifiers were trained using standardized abundance levels of the transcripts (see Section 5.9). Each of the classifiers was used to classify FFPE biological samples using a method of Section 5.4.

Matched pairs (M) of FFPE and analogous frozen biological samples were used according to the disclosed methods to identify mRNA transcripts best preserved in the FFPE tissue samples. The abundance levels of these transcripts were used for training a classification model (i.e., a classifier). The matched pairs were samples derived from the same patient, whereby one section of the tumor was frozen, and the other was fixed in formalin and embedded in paraffin. The matched samples had similar expression patterns because they were derived from the same patient, and therefore most of the variation was due to differences in sample preservation procedure (freezing vs. formalin fixation). This provided the ability to identify mRNA transcripts whose expression was best preserved in FFPE biological samples.

Replicate frozen biological samples (R) of the same tissue type of malignancy, and the same species as the analogous frozen biological sample were used to determine a predetermined threshold of a measure of similarity. The measure of similarity was a Pearson correlation coefficient between abundance levels of respective transcripts. The comparison of expression profiles between the matched pairs with the expression profiles between the frozen biological samples revealed the best preserved transcripts (thus indicating the highly-correlated genes). Preferably, the transcript abundance level data are not standardized before identifying the highly correlated genes.

Subsequently, candidate classifiers were trained using abundance levels of transcripts of the highly-correlated genes in a set of frozen biological samples (F) which were not the analogous frozen biological samples or the replicate frozen biological samples. The classifiers of FIGS. 6A, 6B, and 6C were trained using abundance levels of respective transcripts of from 1000 highly-correlated genes up to 2500 highly-correlated genes. The classifiers of FIG. 6D were trained using abundance levels of respective transcripts of from 1000 highly-correlated genes up to 2000 highly-correlated genes. The classifiers of FIG. 6E were trained using abundance levels of respective transcripts of from 100 highly-correlated genes up to 1000 highly-correlated genes. The classifiers of FIG. 6F were trained using abundance levels of respective transcripts of from 100 highly-correlated genes to 500 highly-correlated genes. This increased the likelihood that the resulting classifiers would have adequate accuracy when applied to the FFPE biological samples, because the transcripts utilized in training the classifiers were known to be robust with respect to formalin-fixation (since they were transcripts of the highly-correlated genes).

The performance of the candidate classifiers was evaluated by processing validation FFPE biological samples (V) using each candidate classifiers. An optimal classifier was selected as the best performing candidate classifier.

It was demonstrated that this approach produced a clinically useful test of tissue of origin of cancer of unknown primary, using approximately 2000 frozen biological samples and approximately 110 FFPE biological samples.

6.1 Cellular Constituent Abundance Values

The following data were received:
a) A set F of gene expression profiles derived from 2032 frozen biological samples (training biological samples).
b) A set M of gene expression profiles derived from 34 matched pairs of FFPE and analogous frozen biological samples. The matched pairs were obtained by dividing a sample in two sections, and subsequently freezing one and fixing the other in formalin.
c) A set R of expression profiles derived from 60 pairs of replicate frozen biological samples. The replicate frozen biological samples were obtained by processing and hybridizing total RNA at different sites.
d) A set V of 70 additional FFPE biological samples used for model selection/validation.

All biological samples in the above sets were human tissue samples.

6.2 Identification of Highly-Correlated Genes

In the first step, for each gene in the expression profiles in set M, Pearson correlation coefficients were computed over the matching pairs. In other words, the correlation was computed over the c(M) pairs of raw (non-standardized) expression values, where c(M) was the cardinality of the matched pairs in the population of matched pairs. The distribution of the correlation coefficients was estimated.

In a second step, for each gene in the expression profiles in set R, Pearson correlation coefficients were computed over the matched pairs and the distribution of the correlation coefficients were estimated. The median of the distribution of the correlation coefficients was set as the predetermined threshold value for indicating mRNA transcripts whose expression were best preserved in the biological samples.

In a third step, the distributions computed in the two foregoing steps were compared. A set G of genes was identified whose reproducibility, based on the median of the Pearson correlation coefficient of the replicates R, was comparable between the sets M and R. The identified genes of set G were highly-correlated genes.

FIGS. 4A and 4B show results of the first and second steps. FIG. 4A shows preservation of RNA in FFPE biological samples; FIG. 4B shows the reproducibility of RNA expression in replicates of frozen biological samples, over the approximately 22,000 available genes on the Affymetrix U133A GeneChip. The histogram of FIG. 4A represents distributions of correlation of mRNA expression computed over matched pairs of FFPE/analogous frozen biological samples, limited to 7500 best-preserved genes, i.e., highly-correlated genes, where the minimum correlation was around 0.2 and the median value was 0.3. The histogram of FIG. 4B shows the distributions of correlation of mRNA expression computed over matched pairs of replicates of frozen biological samples for all available genes. The median of the distribution of values of the Pearson correlation coefficient among the replicate frozen biological samples (R) was about 0.6.

The histogram of FIG. 5A shows the values of correlation of RNA in matched FFPE/analogous frozen biological samples where the threshold correlation was around 0.45 over the total of 22,000 available genes on the Affymetrix U133A GeneChip. FIG. 5B shows the distributions of correlation of mRNA expression computed over the matched pairs of replicates of frozen biological samples for all available genes (the same as FIG. 4D). The threshold correlation over matched pairs in FIG. 5A was set at a higher value (~0.45) than FIG. 4A, and as a result fewer highly-correlated genes were identified (2000 best-preserved genes) as compared to FIG. 4A.

FIGS. 4A and 4B demonstrate that even when restricted to 7500 best preserved genes (out of the total of 22,000 available on the Affymetrix U133A GeneChip), the expression values of genes in FFPE biological samples (FIG. 4A) were relatively poorly correlated to their corresponding expression values in the matching frozen biological samples, with a median value of approximately 0.3. In contrast, replicates in frozen biological samples (FIG. 4B) showed a higher median value of correlation of around 0.6 across all measured genes (approximately 22,000 on the Affymetrix U133A GeneChip). FIGS. 4A and 4B demonstrate that restricting the set of genes to 2000 best preserved highly-correlated genes markedly improved the correlation with expression values in frozen biological samples, to a median value of the distribution of the Pearson correlation coefficient of approximately 0.5. It was expected that the use of the best preserved genes in the classifiers would improve performance of the models when applied to FFPE-derived expression profiles.

6.3 Training of Classifiers Using Highly-Correlated Genes

Figure 6A:
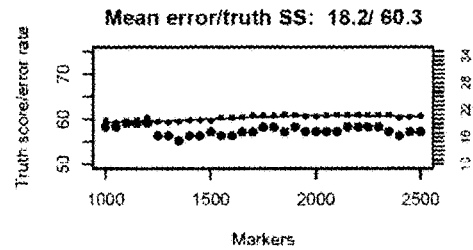

The candidate classifiers were based on an optimal Support Vector Machine model using a linear kernel function. They were trained using standardized abundance levels of respective transcripts of the differing numbers of the highly-correlated genes, identified as described in Section 6.2, above. The candidate classifiers of FIGS. 6A-6F differed in the value of threshold correlation used to identify them, the number of highly-correlated genes used to build them, and the standardization reference array applied to the transcript abundance levels used to train the candidate classifiers. In addition, each of FIGS. 6A-6F shows the performance of several candidate classifiers, where each data point of a truth score and corresponding error rate is an indicator of the performance of an individual candidate classifier built using abundance levels of respective transcripts of the indicated number of highly-correlated genes. That is, FIG. 6A shows the truth score and corresponding error rate for a candidate classifier built using transcript abundance levels of 1000 highly-correlated genes, a candidate classifier built using transcript abundance levels of 1050 highly-correlated genes, a candidate classifier built using transcript abundance levels of 1100 highly-correlated genes, and so forth up to the candidate classifier built using transcript abundance levels of 2500 highly-correlated genes. Similarly, each data point of a truth score and corresponding error rate in FIGS. 6B-6F indicate the performance of individual candidate classifiers.

Figure 6B:
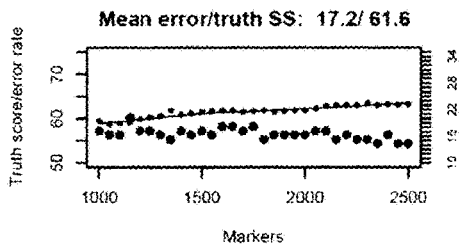
Figure 6C:
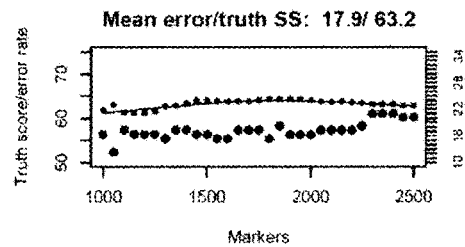

The values of the predetermined threshold used to identify highly-correlated genes used to build the classifiers of FIGS. 6A-6C also differed. The median of the distribution of values of the correlation coefficient among the replicate frozen biological samples used as a basis for determining the threshold was 0.55. The classifiers of FIG. 6A were built using abundance levels of respective transcripts of from 1000 up to 2500 of the 7500 highly-correlated protein-coding genes which were identified using a threshold correlation of 0.39 (~29% lower than the median correlation coefficient among the replicates). The classifiers of FIG. 6B were built using abundance levels of respective transcripts of from 1000 up to 2500 of the 5000 highly-correlated protein-coding genes which were identified using a threshold correlation of 0.43 (~22% lower than the median correlation coefficient among the replicates). The classifiers of FIG. 6C were built using abundance levels of respective transcripts of from 1000 up to 2500 of the 3000 highly-correlated protein-coding genes which were identified using a threshold correlation of 0.50 (~9% lower than the median correlation coefficient among the replicates). The classifiers of FIG. 6D were built using abundance levels of respective transcripts of from 1000 up to the total 2000 highly-correlated protein-coding genes which were identified using a threshold correlation of 0.57 (~4% higher than the median correlation coefficient among the replicates). The classifiers of FIG. 6E were built using abundance levels of respective transcripts of from 100 up to the total 1000 highly-correlated protein-coding genes which were identified using a threshold correlation of 0.63 (~15% higher than the median correlation coefficient among the replicates). The classifiers of FIG. 6F were built using abundance levels of respective transcripts of from 100 up to the total 500 highly-correlated protein-coding genes which were identified using a threshold correlation of 0.68 (~24% lower than the median correlation coefficient among the replicates).

In addition, the standardization reference array applied to the abundance levels of the transcripts used to train the classifiers of FIG. 6A differed from the standardization reference array applied to the abundance levels of the transcripts used to train all of the other candidate classifiers.

Each candidate classifier for classification of FFPE expression profiles was trained using the standardized abundance levels of transcripts of a set of highly-correlated genes G specified for each candidate classifier, in gene expression profiles derived from set F of Section 6.1. The gene expression profiles of set F comprise the abundance levels of respective transcripts of a set of genes in nucleic acid preparations derived from the biological samples of set F. The tumor types of the 2032 training biological samples (set F) were bladder (62), breast (444), colorectal (253), gastric (51), testicular germ cell (119), kidney (151), hepatocellular (41), non-small cell lung (221), non-Hodgkin's lymphoma (95), melanoma (69), ovarian (189), pancreatic (41), prostate (105), soft tissue sarcoma (122), and thyroid (122).

6.4 Standardization

The candidate classifiers were trained using standardized abundance levels of the transcripts of the highly-correlated genes identified as described in Section 6.2. The gene expression profiles under analysis were standardized prior to building the classifier to reduce technical variation incurred by different processing conditions. Standardization reduced technical variability among processing sites, operators, reagent lots and other non-biological sources of variation.

The abundance levels were standardized according to the kernel transformation standardization method disclosed in U.S. application Ser. No. 12/378,187 (which is described in Section 5.9 above). The standardization process itself was based on the identification of a set of stable transcripts whose expression was relatively uniform across a variety of cell types, and which exhibited the least variation over the sets of FFPE-derived expression profiles of the matched pairs M and the validation samples V described in Section 6.1. It was preferred that the reference array genes were reasonably well preserved in the FFPE biological samples to carry out the standardization of the corresponding expression profiles. A subset of reference array genes was identified, which was previously developed for frozen biological samples, and which was suitable for use in FFPE-derived expression profiles. Different standardization reference arrays were generated by varying the set of gene used for the standardization based on the consistent behavior of the abundance levels for the respective transcripts in nucleic acid preparations derived from FFPE biological samples. The different standardization reference arrays generated corresponded to one quarter, one third, one half and two thirds, respectively, of transcripts of the least variable genes of the reference array. Preferably, the standardization genes span the whole range of expression magnitudes to achieve satisfactory predictive performance. This was achieved by dividing the original reference array in five abundance bins by expression magnitude, and retaining a given fraction of the reference genes in each abundance bin (as opposed to a method not using abundance bins which involves retaining the given fraction of the reference genes overall).

The standardization data structure was applied to the abundance values of the expression profiles using the kernel transformation (described above in Section 5.9.2) prior to training the candidate classifiers. The effect of application of the standardization data structure to an expression profile using the kernel transformation was to introduce a fraction parameter as a multiplier to each of the abundance values of the expression profile, where the fraction parameter was a continuous variable having a value in the interval (0; 1). Each abundance value in the expression profile may have been multiplied by a different fraction parameter as a result of application of the standardization data structure using the kernel transformation.

6.5 Evaluation of Performance of Classifiers for Classification According to Tissue of Origin of Tumors Each of the candidate classifiers of Section 6.3 was used to classify test biological samples as to a tissue of origin.

The performance of the different candidate classifiers was evaluated by the following steps:

a) each of the candidate classifiers was applied to the standardized expression profiles of the FFPE biological samples of the set V and the FFPE biological samples of the matched pairs M.

b) the results of the application of the candidate classifiers were compared.

c) an optimal classifier for analysis of the set V of FFPE biological samples and the FFPE biological samples of the matched pairs M was identified as the candidate classifier which produced the best performance.

The classification algorithm employed for training the classifiers assigned a score between 0 and 100 to each of 15 tumor types (phenotypic characterizations). The candidate classifiers were trained using abundance levels, in the gene expression profiles derived from 2032 frozen biological samples (set F), of the respective transcripts of the highly-correlated genes used to build each candidate classifier. The 15 scores (i.e., one score for each tumor type) summed to 100 and thus had a probabilistic interpretation. The optimal classifier built produced accurate determination of tumor types in a clinical trial of an independent set of 352 FFPE biological samples.

FIGS. 6A-6F show the evaluation of the performance of the candidate classifiers applied to the FFPE biological samples of the set V and the FFPE biological samples of the matched pairs M, to allow for selection of the best performing classifier suitable for classification of FFPE biological samples. Each plot in FIGS. 6A-6F shows the truth score and error rate with application of each candidate classifier built using the indicated number of highly-correlated genes.

The candidate classifiers of FIGS. 6A, 6B, and 6C were trained using up to 2500 highly-correlated genes partly due to computational limitations (computations took less time if the classifier was built using fewer genes), and partly because the performance of candidate classifiers tended to level off when 2500 genes or greater was used.

A primary performance evaluation parameter used was the classification error rate (larger dots, corresponding to right y-axis). The mean truth similarity score assigned to the actual tumor type (smaller dots, corresponding to left y-axis) was used as a secondary performance evaluation parameter to resolve a tie if the classification error rate of two candidate classifiers was similar. Values of the mean classification error rate and the mean truth similarity score (SS) are shown in each of FIGS. 6A-6F. These performance indicators were computed over the available FFPE biological samples, i.e., over the union of the FFPE biological samples of the set V and the FFPE biological samples of the matched pairs M. The truth similarity score was the score assigned by the algorithm to the actual tumor type of the sample under analysis. Ideally, the truth similarity score should equal 100, and the remaining 14 scores should equal 0.

Figure 6D:
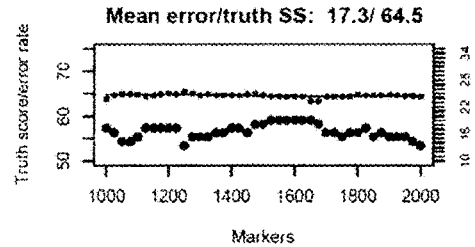
Figure 6E:
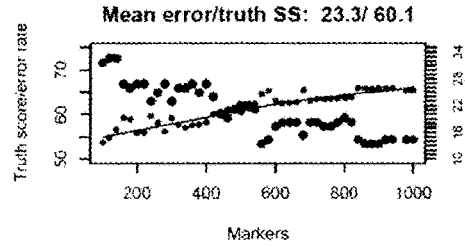
Figure 6F:
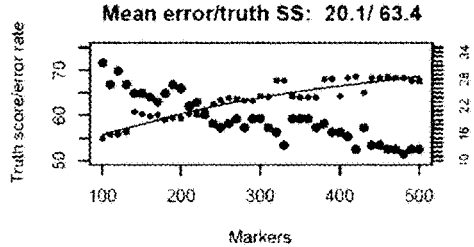

The optimal classifier was found to be the candidate classifier of FIG. 6D which was built using abundance levels of transcripts of 2000 highly-correlated genes. The optimal classifier in FIG. 6D had the lowest classification error rate (about 13). The candidate classifier of FIG. 6F which was built using abundance levels of transcripts of 500 highly-correlated genes exhibited a similar value error rate. However, the classifier of FIG. 6D was considered the optimal classifier, since a classifier built based on a higher number of genes was generally more robust (i.e., the optimal classifier of FIG. 6D was built with a higher number of genes, i.e., with 2000 genes as opposed to the 500 genes used for the candidate classifier of FIG. 6F).

7. REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8. MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the fill scope of equivalents to which such claims are entitled.

What is claimed:

1. A method of classifying a test biological sample, preserved in a fixed state, from a human as to a cancer type using a support vector machine based classifier, said method comprising, at a computer system having at least one processor and memory storing at least one program for execution by the at least one processor to perform the method:
   (A) obtaining, for each respective gene $x_i$ in a first plurality of genes $X=\{x_1, \ldots, x_N\}$, a corresponding plurality $Y_i=\{y_{i1}, \ldots, y_{iM}\}$ of pairs of expression values for gene $x_i$, each respective pair of expression values $y_{ij}=\{y_{ija}, y_{ijb}\}$ in $Y_i$ consisting of (i) a first expression value $y_{ija}$ for the respective gene $x_i$ from a first human sample $z_{ia}$, preserved in a frozen state, and (ii) a second expression value $y_{ijb}$ for the respective gene $x_i$ from a second human sample $z_{ib}$, preserved in a fixed state, in a first plurality of pairs of human samples $Z=\{z_1, \ldots, z_O\}$, wherein each sample in each respective pair of human samples $z_i=\{z_{ia}, z_{ib}\}$ is from the same tissue type and the same subject as the other sample in the respective pair of human samples, and wherein N, M, and O are each positive integers and wherein M is 5 or greater;
   (B) determining for each respective pair of expression values $y_{ij}=\{y_{ija}, y_{ijb}\}$, a corresponding plurality of correlation coefficients $W_i=\{w_{i1}, \ldots, w_{iM}\}$ by comparing the first expression value $y_{ija}$ for the respective gene $x_i$ from the first human sample $z_{ia}$, preserved in a frozen state, to the second expression value $y_{ijb}$ for the respective gene $x_i$ from the second human sample $z_{ib}$, preserved in a fixed state;
   (C) selecting a second plurality of genes consisting of a sub-plurality of genes in the first plurality of genes using the criterion that each respective gene $x_i$ in the second plurality of genes has a correlation coefficient $w_{ij}$ of 0.5 or higher for the first and second expression values $\{y_{ija}, y_{ijb}\}$ across the plurality $Y_i$ of pairs of expression values for gene $x_i$;
   (D) obtaining gene expression data from a second plurality of human samples, preserved in frozen states, each respective sample in the second plurality of human samples characterized by a cancer type selected from the group consisting of bladder, breast, colorectal, gastric, testicular germ cell, kidney, heptatocellular, non-small cell lung, non-Hodgkin's lymphoma, melanoma, ovarian, pancreatic, prostate, soft tissue sarcoma, and thyroid, wherein the gene expression data is stored in the memory;
   (E) training a support vector machine based classifier using (i) the gene expression data from the obtaining step (C), limited to a third plurality of genes, wherein at least ninety percent of the genes in the third plurality of genes are in the second plurality of genes, and (ii) the cancer type for each respective sample in the second plurality of samples, thereby constructing the support vector machine based classifier configured to determine the cancer type of the test biological human sample;
   (F) receiving abundance levels of respective transcripts of a group of genes in a nucleic acid preparation derived from said test biological sample; and
   (G) classifying said test biological sample as to said cancer type by applying said support vector machine based classifier constructed in the training step (D) to the abundance levels of the respective transcripts of the group of genes in the nucleic acid preparation derived from said test biological sample,
   wherein the obtaining step (A), the determining step (B), the selecting step (C), the obtaining step (D), the training step (E) and the processing step (F) are each performed using one or more suitably programmed computers.

2. The method of claim 1, further comprising outputting to a user, a user interface device, a computer readable storage medium, a monitor, a local computer, or a computer that is part of a network; or displaying, from said support vector machine based classifier an indication of said cancer type phenotypic characterization.

3. The method of claim 1, wherein said second plurality of genes comprises at least 100 protein-coding genes.

4. The method of claim 1, wherein M is at least 10.

5. The method of claim 1, wherein the corresponding plurality $Y_i=\{y_{i1}, \ldots, y_{iM}\}$ of pairs of expression values for gene $x_i$, comprise abundance levels of respective mRNAs translated from gene $x_i$, abundance levels of nucleic acids derived from the respective mRNAs, abundance levels of cDNAs corresponding to said respective mRNAs, or abundance levels of cRNAs corresponding to said respective mRNAs.

6. The method of claim 1, wherein the fixed state is obtained with a crosslinking agent.

7. The method of claim 6, wherein said fixed state is a formalin-fixed paraffin-embedded state.

8. A computer program product for use in conjunction with a computer having one or more memory units and one or more processor units, the computer program product comprising a computer readable storage medium having a computer program mechanism encoded thereon, wherein said computer program mechanism is loaded into the one or more memory units of said computer and cause the one or more processor units of the computer to perform the method of claim 1.

9. The computer program product of claim 8, wherein said computer program mechanism can be loaded into the one or more memory units of said computer and cause the one or more processor units of the computer to output to a user, a user interface device, a monitor, a computer readable storage medium, a computer-readable memory, or a local or remote computer system; or displaying, from said classifier an indication of said cancer type.

10. The method of claim 1, wherein the expression values obtained in steps (A) and (D) were derived from microarray experiments.

11. The computer program product of claim 8, wherein the expression values obtained in steps (A) and (D) were derived from microarray experiments.

* * * * *